US008524778B2

(12) United States Patent
Greig et al.

(10) Patent No.: US 8,524,778 B2
(45) Date of Patent: *Sep. 3, 2013

(54) BIPHENYL-4-YL-SULFONIC ACID ARYLAMIDES AND THEIR USE AS THERAPEUTIC AGENTS

(75) Inventors: Iain Robert Greig, Aberdeen (GB); Robert Jurgen Van't Hof, Edinburgh (GB); Stuart Hamilton Ralston, Edinburgh (GB)

(73) Assignee: PIMCO 2664 Limited, London (GB)

( * ) Notice: Subject to any disclaimer, the term of this patent is extended or adjusted under 35 U.S.C. 154(b) by 885 days.

This patent is subject to a terminal disclaimer.

(21) Appl. No.: 12/531,732

(22) PCT Filed: Mar. 20, 2008

(86) PCT No.: PCT/GB2008/000989
§ 371 (c)(1),
(2), (4) Date: Nov. 18, 2009

(87) PCT Pub. No.: WO2008/114022
PCT Pub. Date: Sep. 25, 2008

(65) Prior Publication Data
US 2010/0286266 A1  Nov. 11, 2010

(30) Foreign Application Priority Data

Mar. 21, 2007 (GB) .................................. 0705400.0

(51) Int. Cl.
*A61K 31/18* (2006.01)
*C07C 307/00* (2006.01)

(52) U.S. Cl.
USPC ........... 514/604; 514/602; 514/601; 514/579; 564/92; 564/90; 564/84; 564/80

(58) Field of Classification Search
None
See application file for complete search history.

(56) References Cited

U.S. PATENT DOCUMENTS

| 4,119,784 | A | 10/1978 | Conrow et al. |
| 4,948,809 | A | 8/1990 | Witte et al. |
| 5,760,028 | A | 6/1998 | Jadhav et al. |
| 6,159,995 | A | 12/2000 | Thorwart et al. |
| 6,451,824 | B1 | 9/2002 | Thorwart et al. |
| 6,849,635 | B2 * | 2/2005 | Dhanak et al. ................. 514/256 |
| 7,560,597 | B2 * | 7/2009 | Greig et al. .................... 568/327 |
| 7,572,825 | B2 * | 8/2009 | Ralston et al. ................ 514/436 |
| 7,598,289 | B2 * | 10/2009 | Ralston et al. ................ 514/436 |
| 7,745,424 | B2 * | 6/2010 | Ralston et al. ................ 514/124 |
| 7,964,643 | B2 | 6/2011 | Ralston et al. |
| 8,207,167 | B2 * | 6/2012 | Greig et al. ................ 514/239.5 |
| 2003/0144292 | A1 | 7/2003 | Natchus et al. |
| 2005/0119305 | A1 | 6/2005 | Naka et al. |
| 2005/0227987 | A1 | 10/2005 | Vicker et al. |
| 2006/0030543 | A1 | 2/2006 | Malecha et al. |
| 2007/0191370 | A1 | 8/2007 | Devasagayaraj et al. |
| 2008/0119555 | A1 | 5/2008 | Ralston et al. |
| 2008/0255240 | A1 * | 10/2008 | Christiansen et al. ........ 514/604 |
| 2010/0286266 | A1 | 11/2010 | Greig et al. |
| 2011/0172189 | A1 | 7/2011 | Greig et al. |
| 2011/0190302 | A1 | 8/2011 | Greig et al. |

FOREIGN PATENT DOCUMENTS

| DE | 10 46 220 | 12/1958 |
| DE | 3000519 A1 | 8/1980 |
| EP | 0877018 A1 | 11/1998 |
| EP | 0 960 882 | 12/1999 |
| EP | 0 877 019 | 12/2001 |
| EP | 1 431 267 | 6/2004 |
| EP | 1 491 190 | 12/2004 |
| EP | 1659113 A1 | 5/2006 |
| GB | 597810 | 2/1948 |
| JP | 11246527 | 9/1999 |
| JP | 2001-504809 | 4/2001 |
| WO | WO 96/37492 | 11/1996 |
| WO | WO 97/16433 | 5/1997 |
| WO | WO 97/33887 | 9/1997 |
| WO | WO 98/03166 | 1/1998 |
| WO | WO 98/16503 | 4/1998 |
| WO | WO 98/23608 | 6/1998 |
| WO | WO 98/43962 | 10/1998 |
| WO | WO 98/50342 | 11/1998 |

(Continued)

OTHER PUBLICATIONS

Armour K.J., et al., 2001, "Inhibition of bone resorption in vitro and prevention of ovariectomy-induced bone loss in vivo by flurbiprofen nitroxybutylester (HCT1026)," Arthritis and Rheumatism, vol. 44, No. 9, pp. 2185-2192.
Augstein, J., et al., 1965, "Some cardiovascular effects of a series of aryloxyalkylamines 1", J. Med. Chem., vol. 8, pp. 356-367.
Baud et al., 2009, "Is NfkB a good target for cancer therapy? Hopes and pitfalls", Nat. Rev. Drug Disc., vol. 8, pp. 33-40.
Corey EJ, Shibata S, Bakshi RK, 1988, "An effcicient and catalytically enantioselective route to (S)-(−)-Phenyloxirane," J. Org. Chem., vol. 53, pp. 2861-2863.

(Continued)

*Primary Examiner* — Brandon Fetterolf
*Assistant Examiner* — Theodore R West
(74) *Attorney, Agent, or Firm* — Swanson & Bratschun, L.L.C.

(57) ABSTRACT

The present invention pertains generally to the field of therapeutic compounds, and more specifically to certain aryl sulfonamides and related compounds (collectively referred to herein as 'BPSAAA compounds'), as described herein, and including, for example, biphenyl-4-sulfonic acid (hydroxyalkyl-phenyl)-amides and related compounds. The present invention also pertains to pharmaceutical compositions comprising such compounds, and the use of such compounds and compositions, both in vitro and in vivo, in treatment and/or prevention, for example, of inflammation and/or joint destruction and/or bone loss; of disorders mediated by excessive and/or inappropriate and/or prolonged activation of the immune system; of, inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activation in rheumatoid arthritis, osteoporosis, cancer associated bone disease, Paget's disease and the like.

50 Claims, 3 Drawing Sheets

(56) References Cited

FOREIGN PATENT DOCUMENTS

| | | |
|---|---|---|
| WO | WO 99/37621 | 7/1999 |
| WO | WO 99/42443 | 8/1999 |
| WO | WO 99/59992 A1 | 11/1999 |
| WO | WO 01/16137 | 3/2001 |
| WO | WO 01/90077 | 11/2001 |
| WO | WO 02/060867 | 8/2002 |
| WO | WO 02/074298 | 9/2002 |
| WO | WO 03/037321 | 5/2003 |
| WO | WO 2004/022561 | 3/2004 |
| WO | WO 2004/039784 A1 | 5/2004 |
| WO | WO 2004/073619 | 9/2004 |
| WO | WO 2004/098582 | 11/2004 |
| WO | WO 2004/106290 A1 | 12/2004 |
| WO | WO 2005/060963 A1 | 7/2005 |
| WO | WO 2005/080367 | 9/2005 |
| WO | WO 2005/085189 A2 | 9/2005 |
| WO | WO 2005/105712 A1 | 11/2005 |
| WO | WO 2005/118528 A2 | 12/2005 |
| WO | WO 2006/134467 A1 | 12/2006 |
| WO | WO 2007/008541 A2 | 1/2007 |
| WO | WO 2007/026962 A1 | 3/2007 |
| WO | WO 2008/114022 | 9/2008 |
| WO | WO 2010/032009 A1 | 3/2010 |
| WO | WO 2010/032010 A1 | 3/2010 |

OTHER PUBLICATIONS

Coxon, F.P., et al., 2000, "Protein geranylgeranylation is required for osteoclast formation, function, and survival: inhibition by bisphosphonates and GGTI-298," J.Bone Miner.Res., vol. 15, pp. 1467-1476.
Degenhardt, C.R., et al., 1986, "Synthesis of Ethenylidenebis(phosphonic acid) and its Tetraalkyl Esters," J. Org. Chem., vol. 51, pp. 3488-3490.
Eberhard, A., et al., 1965, "Hydrolysis of Phostonates," J. Amer. Chem. Soc., vol. 87, pp. 253-260.
Ha-Duong, N-T, et al, 2001, "Synthesis of sulfaphenazole derivatives and their use as inhibitors and tools for comparing the active sites of human liver cytochromes P450 of the 2C subfamily", J. Med. Chem., vol. 44, pp. 3622-3631.
Herczegh, P., et al, 2002, "Osteoadsorptive Bisphosphonate Derivatives of Fluoroquinolone Antibacterials," J. Med. Chem., vol. 45, pp. 2338-2341.
Hughes, D.E., et al., 1997, "Apoptosis in bone physiology and disease," J. Clin. Pathol.: Molecular Pathology, vol. 50, pp. 132-137.
International Preliminary Report on Patentability (IPRP) for PCT/GB2005/002043, (Dec. 2006).
International Preliminary Report on Patentability (IPRP) for PCT/GB2009/002221, (Mar. 2011).
International Preliminary Report on Patentability (IPRP) for PCT/GB2009/002223, (Mar. 2011).
International Search Report (ISR) and Written Opinion of International Searching Authority (WOISA) for PCT/GB2005/002043, (Nov. 2005).
International Search Report (ISR) and Written Opinion of International Searching Authority (WOISA) for PCT/GB2009/002221, (Jan. 2010).
International Search Report (ISR) and Written Opinion of International Searching Authority (WOISA) for PCT/GB2009/002223, (Feb. 2010).
Kong, Y.Y., et al., 1999, "OPGL is a key regulator of osteoclastogenesis, lymphocyte development and lymph-node organogenesis," Nature, vol. 397, pp. 315-323.
Li et al., 2008, "A tumor necrosis factor-[alpha]-mediated pathway promoting autosomal dominant polycystic kidney disease", Nature Medicine, vol. 14(8), pp. 863-868.
MacPherson, H; et al., 1999, "Expression and functional role of nitric oxide synthase isoforms in human osteoblast-like cells," Bone, vol. 24, pp. 179-185.
Mantovani, 2009, "Inflaming metastasis", Nature, vol. 457, pp. 36-37.

Mundy, G.R., 1996, "Chapter 1: Bone Remodeling", in Bone Remodeling and its disorders (2nd edition), London, (Ed. Martin Dunitz), pp. 1-11.
Nyormoi, O., et al., 2003, "An MMP-2/MMP-9 inhibitor, 5a, enhances apoptosis induced by ligands of the TNF receptor superfamily in cancer cells", Cell Death and Differentiation, vol. 10, pp. 558-569.
Peyman, A., et al., 2001, "$\alpha v \beta 3$ antagonists based on a central thiophene scaffold", Bio. & Med. Chem. Letters, Vo. 11, pp. 2011-2015.
Raisz, L.G., 1988, "Local and systemic factors in the pathogenesis of osteoporosis," N. Engl. J. Med., vol. 318, pp. 818-828.
Ralston, S.H., 1997, "Science, Medicine and the Future: Osteoporosis," Br. Med. J., vol. 315, pp. 469-472.
Ramachandran PV, Gong B, Brown HC, 1995, "Chiral synthesis via organoboranes", J. Org. Chem., vol. 60, pp. 41-46.
Rodan, G.A., et al., 1997, "The missing bone," Cell, vol. 89, pp. 677-680.
Takahashi, N.; et al., 1988, "Osteoblastic cells are involved in osteoclast formation," Endocrinology, vol. 123, pp. 2600-2602.
Takasuka, M., et al., 1991, "FTIR spectral study of intramolecular hydrogen bonding in thromboxane A2 receptor antagonist S-145 and related compounds. 3. Conformation and activity of S-145 analogues", J. Med. Chem., vol. 34, pp. 1885-1891.
UK Search Report for GB 0412553.0, (Sep. 2004).
UK Search Report for GB 0817207.4, (Jan. 2009).
UK Search Report for GB 0817208.2, (Jan. 2009).
Yasuda, H., et al, 1998, "Identity of osteoclastogenesis inhibitory factor (OCIF) and osteoprotegerin (OPG): a mechanism by which OPG/OCIF inhibits osteoclastogenesis in vitro", Endocrinology, vol. 139(3), pp. 1329-1337.
Argus et al. (1958) Brit. J. Cancer, 12:636-644, "Distribution studies with sulphur 35-labeled disulfonamides in tumor-bearing and tumor-free mice".
Baud et al. (1999) Genes Dev., 13:1297-1308, "Signaling by proinflammatory cytokines: oligomerization of TRAF2 and TRAF6 is sufficient for JNK and IKK activation and target gene induction via an amino-terminal effector domain".
Brennan et al. (Jul. 1989) Lancet, 2:244-247, "Inhibitory effect of TNF alpha antibodies on synovial cell interleukin-1 production in rheumatoid arthritis".
Brennan et al. (1992) Eur. J. Immunol., 22:1907-1912, "Enhanced expression of tumor necrosis factor receptor mRNA and protein in mononuclear cells isolated from rheumatoid arthritis synovial joints".
Brennan et al. (1996) Curr. Opin. Immunol., 8:872-877, "Cytokines in autoimmunity".
CHEMCATS record for Enamine Screening Library, Enamine, Kiev, Ukraine, CAS Registry No. 950020-41-4 (Jan. 2008).
CHEMCATS record for LaboTest Stock Catalog, LaboTest, Niederschoena, Germany, CAS Registry No. 331653-75-9, (Jul. 2007).
CHEMCATS records for Nanosyn Compound Library, Nanosyn Combinatorial Synthesis Inc., Menlo Park, CA, USA, CAS Registry Nos. 313495-94-2, 313521-07-2, (Apr. 2007).
CHEMCATS record for Ryan Scientific Screening Library, Ryan Scientific, Inc., Mt. Pleasant, SC, USA, CAS Registry No. 302603-86-7, (Jan. 2008).
CHEMCATS record for Scientific Exchange Product List, Scientific Exchange, Inc., Centre Ossipee, NH, USA, CAS Registry No. 312756-83-5, (Jan. 2008).
CHEMCATS records for Spectrum Info Catalog, Spectrum Info Ltd., Kiev, Ukraine, CAS Registry No. 885269-21-6, 885269-32-9, 885269-42-1, 885269-85-2, 885269-88-5, 885269-91-0, (Sep. 2007).
Elliott et al. (Oct. 1994) Lancet, 344:1105-1110, "Randomised double-blind comparison of chimeric monoclonal antibody to tumour necrosis factor alpha (cA2) versus placebo in rheumatoid arthritis".
Feldmann et al. (1994) Circ. Shock, 43:179-184, "TNF alpha as a therapeutic target in rheumatoid arthritis".
Feldmann et al. (May 1996) Cell, 85:307-310, "Rheumatoid arthritis".

Feldmann et al. (2001) Curr. Dir. Autoimmun., 3:188-199, "The role of TNF alpha and IL-1 in rheumatoid arthritis".

Firestein (Nov. 1996) Arthritis Rheum., 39:1781-1790, "Invasive fibroblast-like synoviocytes in rheumatoid arthritis. Passive responders or transformed aggressors?".

Firestein et al. (Apr. 1999) Arthritis Rheum., 42:609-621, "Signal transduction and transcription factors in rheumatic disease".

Firestein (Jun. 2005) J. Clin. Rheumatol., 11:S39-S44, "Immunologic mechanisms in the pathogenesis of rheumatoid arthritis".

Gottlieb (Jan. 2005) Nat. Rev. Drug Disc., 4:19-34, "Psoriasis: Emerging Therapeutic Strategies".

Greig et al. (2006) J. Med. Chem., 49:7487-7492, "Development and characterization of biphenylsulfonamides as novel inhibitors of bone resorption".

Jimi et al. (May 2004) Nat. Med., 10:617-624, "Selective inhibition of NF-kappa B blocks osteoclastogenesis and prevents inflammatory bone destruction in vivo".

Joosten et al. (May 1996) Arthritis Rheum., 39:797-809, "Anticytokine treatment of established type II collagen-induced arthritis in DBA/1 mice. A comparative study using anti-TNF alpha, anti-IL-1 alpha/beta, and IL-1Ra".

Klareskog et al. (Aug. 2006) Nat. Clin. Pract. Rheumatol., 2:425-433, "Mechanisms of disease: Genetic susceptibility and environmental triggers in the development of rheumatoid arthritis".

Klareskog et al. (Mar. 2006) Ann. Rheum. Dis., 65:1578-1584, "A long-term, open-label trial of the safety and efficacy of etanercept (Enbrel) in patients with rheumatoid arthritis not treated with other disease-modifying antirheumatic drugs".

Korzenik et al. (Mar. 2006) Nat. Rev. Drug Disc., 5:197-209, "Evolving knowledge and therapy of inflammatory bowel disease".

Liu (Jan. 2005) Cell Res., 15:24-27, "Molecular mechanism of TNF signaling and beyond".

Luckman et al. (1998) J. Bone Miner. Res., 13:1668-1678, "Heterocycle-containing bisphosphonates cause apoptosis and inhibit bone resorption by preventing protein prenylation: evidence from structure- activity relationships in J774 macrophages".

McInnes et al. (2005) Curr. Pain Headache Rep., 9:405-411, "Targeting cytokines beyond tumor necrosis factor-alpha and interleukin-1 in rheumatoid arthritis".

Mohan et al. (Jul. 1993) J. Med. Chem., 36:1996-2003, "Structure-Activity Relationship Studies with Symmetric Naphthalenesulfonic Acid Derivatives. Synthesis and Influence of Spacer and Naphthalenesulfonic Acid Moiety on Anti-HIV-1 Activity".

Mount et al. (Jan. 2005) Nat. Rev. Drug. Disc., 2:11-12, "Rheumatoid arthritis market".

Nociari et al. (1998) Journal of Immunological Methods, 213:157-167, "A Novel one-step, highly sensitive fluorimetric assay to evaluate cell-mediated cytotoxicity".

O'Brien et al. (Jan. 2000) J. Med. Chem., 43:156-166, "Structure-activity relationships and pharmacokinetic analysis for a series of potent, systemically available biphenylsulfonamide matrix metalloproteinase inhibitors".

Roodman (2006) Ann. N. Y. Acad. Sci., 1068:100-109, "Regulation of osteoclast differentiation".

Smolen et al. (Jun. 2003) Nat. Rev. Drug Disc., 2:473-488, "Therapeutic Strategies for Rheumatoid Arthritis".

Tanaka et al. (2003) J. Bone Miner. Metab., 21:123-133, "Signal transduction pathways regulating osteoclast differentiation and function".

Van den Berg et al. (1999) Baillieres Best Pract. Res. Clin. Rheumatol., 13:577-597, "Pathogenesis of joint damage in rheumatoid arthritis: evidence of a dominant role for interleukin-I".

Van den Berg (2002) Clin. Exp. Rheumatol., 20:S21-S25, "Is there a rationale for combined TNF and IL-1 blocking in arthritis?".

Weissmann (2006) Bull. Hosp. Jt. Dis., 64:12-15, "The pathogenesis of rheumatoid arthritis".

Ziff (1990) J. Rheumatol., 17:127-133, "Rheumatoid arthritis—it's present and future".

UK Search Report for GB 0705400.0, (Jul. 2007).

UK Search Report—Examiner's Chemical Abstracts online search results, (Jul. 2007).

International Search Report (ISR) and Written Opinion of the International Searching Authority (WOISA) for PCT/GB2008/000989, (Mar. 2008).

International Preliminary Search Report on Patentability (IPRP) for PCT/GB2008/000989, (Mar. 2008).

Annex to UK Search Report for GB 0705400.0—Jul. 9, 2007.

* cited by examiner

| TNF | - | + | + | + | + | + |
| ABD455 | - | - | 10 | 25 | - | - |
| (μM) | - | - | - | - | 10 | 25 |

| TNF | + | + | + | + | + | + |
| ABD455 | - | - | 10 | 25 | - | - |
| (μM) | - | - | - | - | 10 | 25 |

BIPHENYL-4-YL-SULFONIC ACID ARYLAMIDES AND THEIR USE AS THERAPEUTIC AGENTS

RELATED APPLICATIONS

This application is a 35 U.S.C. §371 national phase application of PCT/GB2008/000989 (WO 2008/114022), filed on Mar. 20, 2008, entitled "Biphenyl-4-yl-Sulfonic Acid Arylamides and Their Use as Therapeutic Agents," which application claims the benefit of Great Britain Application Serial No. 0705400.0, filed on Mar. 21, 2007, which is specifically incorporated herein by reference in its entirety.

TECHNICAL FIELD

The present invention pertains generally to the field of therapeutic compounds, and more specifically to certain aryl sulfonamides and related compounds (collectively referred to herein as "BPSAAA compounds"), including, for example, biphenyl-4-sulfonic acid (hydroxyalkyl-phenyl)-amides and related compounds. The present invention also pertains to pharmaceutical compositions comprising such compounds, and the use of such compounds and compositions, both in vitro and in vivo, in treatment and/or prevention, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activity in rheumatoid arthritis, osteoporosis, cancer associated bone disease, Paget's disease and the like, etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Rheumatoid Arthritis

Rheumatoid arthritis (RA) is a chronic inflammatory disease characterised by painful swelling, stiffness, loss of movement and the destruction of cartilage and bone. RA is characterised by an inflammation of the synovial lining of multiple joints and commonly affects the joints of the wrist and hands and may also affect the elbows, shoulders, hips, neck and knees; the ultimate hallmark of RA is joint destruction. RA is a common disease, estimated to affect up to 1% of adults in the developed world, with women more than twice as likely to be affected and over 30% of patients likely to become severely disabled within 20 years (see, e.g., Feldmann et al., 2006). RA is one of the most important causes of disability in the western world and is associated with a significant reduction in quality of life as well as increased mortality if left untreated. The disease can start at any age, with individuals aged between 40 and 70 most commonly affected.

The exact cause of RA remains unclear, but is highly complex and may involve the combination of a number of factors which lead to the development of autoantibodies, formation of immune complexes, production of pro-inflammatory cytokines, angiogenesis and eventual bone and cartilage loss (see, e.g., Klareskog et al, 2006; Ziff et al, 1990; Weissmann et al, 2006; Firestein et al, 2005). These factors include an abnormal immune response caused by reduced self tolerance or a biological trigger such as reaction to environmental factors, infectious agents, or hormonal stimulus (see, e.g., Klareskog et al, 2006); antibodies to the Fc fragment of IgG, known as rheumatoid factor, are present in 60-80% of adults with RA (see, e.g., Weissmann et al, 2006) but it is not known whether this factor is responsible for initiating the inflammatory cascade or is generated at a later stage and propagates the process (see, e.g., Weissmann et al, 2006); there is also a notable genetic predisposition to the disease, as shown by the presence of HLA-DR4 antibody in 70% of patients (see, e.g., Klareskog et al, 2006).

At the cellular level, development of RA usually commences with T-cells infiltrating the synovial membrane lining the affected joint; this then leads to the activation of macrophages, monocytes and synovial fibroblasts (see, e.g., Firestein, 1996) by way of cell-cell contact and release of various cytokines, including TNFα and IL-1 (see, e.g., Feldmann, 1996). Activation of these cells leads to the overproduction of a range of pro-inflammatory cytokines of which the most important are TNFα, IL-1 and IL-6 (see, e.g., Brennan et al, 1996; McInnes et al, 2005). These pro-inflammatory cytokines are then instrumental in orchestrating several complex signal transduction cascades, including the NFκB, MAPK and Jak/STAT pathways (see, e.g., Firestein et al, 1999) which lead to the induction of genes coding for various products that propagate the inflammatory response and also promote tissue destruction. These products include tissue-degrading enzymes such as collagenases, matrix metalloproteases, cathepsins, and other pro-inflammatory factors such as selectins, integrins, leukotrienes, prostaglandins, chemokines, and other cytokines. Furthermore, TNFα and IL-1 also induce RANKL expression.

RANKL is an essential factor for the generation of osteoclasts (see, e.g., Tanaka et al, 2003; Roodman, 2006), and upregulated RANKL-production leads to increased osteoclasts differentiation and ultimately bone destruction (see, e.g., Tanaka et al, 2003; Roodman, 2006). The inflammatory response leads to the accumulation of many leukocytes and immune factor populations within the affected joint and also to hyperplasia of the Type-A and Type-B synoviocytes (see, e.g., Firestein et al, 2005), leading to thickening and vascularisation of the synovium into a destructive and aggressive tissue known as a pannus. The pannus contains both osteoclasts which destroy bone, and metalloproteases which continue the destruction of cartilage.

Treatment of Rheumatoid Arthritis

Early therapies for RA focussed on controlling the symptoms of the disease, mainly by reduction of inflammation, rather than retarding disease progression. These drugs included NSAIDs such as aspirin, diclofenac and naproxen and, until recently, the COX-2 selective drugs Celebrex® and Vioxx® were also widely used. Inflammation was further controlled by glucocorticoids, and their combination with NSAIDs provided reasonably effective short-term control of the inflammation. More recently, a more aggressive approach to treating RA has been introduced starting at disease onset, using so-called disease-modifying anti-rheumatic drugs (DMARDs), which act to slow or even prevent disease progression. These include a number of older drugs, including gold salts; sulfasalazine; antimalarials such as hydroxychloroquine; D-penicillamine; immunosuppressants such as mycophenolic acid, azathioprine, cyclosporine A, tacrolimus and sirolimus; minocycline; leflunomide; and most importantly, methotrexate (see, e.g., Smolen et al, 2003).

Methotrexate is now the gold-standard therapy for clinical trial comparisons, and is generally used in combination with newer therapies. It is effective in most patients but, in common with all of the above agents, has significant gastrointestinal side effects, which lead to roughly 50% of patients eventually having to cease treatment with methotrexate (see, e.g., Mount et al, 2005). A further drawback of these older DMARDs is the length of time taken for the drug to start acting, ranging from weeks with methotrexate, to months with gold salts. Whilst full remissions only occur in about a quarter of patients, for those showing no effect it is not generally possible to stop therapy without suffering the risk of a more violent disease rebound (see, e.g., Smolen et al, 2003). In recent years, the treatment of RA has been revolutionised by the advent of biological agents which target specific inflammatory pathways. The first and most important of these are the anti-tumour necrosis factor (anti-TNF) agents (see, e.g., Elliott et al, 1994).

The Role of TNFα in RA

As discussed above, the TNF superfamily of receptors and ligands plays a key role in the causation of inflammation and associated local and systemic bone loss. TNFα production within the joint may in fact play the pivotal role in orchestrating the production of other factors which leads to the persistence of inflammation and tissue damage (see, e.g., Feldmann et al, 2001; Brennan et al, 1999; Brennan, 1992). The importance of TNFα in RA is highlighted by the finding that antibodies blocking TNF can prevent inflammation in animal models of RA, and that anti-TNF therapy is currently the most effective treatment for RA (see, e.g., Elliott et al, 1994; Feldmann et al, 1994; Joosten et al 1996, Klareskog et al, 2006). However, there is evidence that there are some TNF-independent effects of IL-1 in RA, most notably bone destruction (see, e.g., van den Berg et al, 1999; van den Berg et al, 2002).

TNF is a cytokine that effects many different functions, including the alteration of tissue remodelling, changes to the permeability of the epithelial cell barrier, activation of macrophages, up-regulation of adhesion molecules, recruitment of other immune response effectors and, most importantly in RA, it instigates the signalling cascade which leads to the activation of the transcription factors NFκB and AP-1 (see, e.g., Liu, 2005; Baud et al, 1999). Binding of TNF and IL-1 to their respective receptors leads to the recruitment of downstream signal transducers called TRAFs. Further kinases are recruited by the TRAFs, and the resulting kinase complex activates the Map-kinase pathway, ultimately leading to activation of AP-1, and the phosphorylation of IκB kinase. IκB is the inhibitor of NFκB, which acts by preventing translocation of NFκB to the nucleus. Phosphorylation of IκB by IκB kinase leads to degradation of IκB. Once IκB has been degraded, NFκB migrates to the nucleus, where it promotes transcription of anti-apoptotic genes, which promote survival of T and B-cells, thereby prolonging the immune response. This prolongation of the inflammatory response is central to the chronic nature of RA. The importance of NFκB activation is demonstrated by the fact that inhibition of NFκB activity by inhibitory peptides can prevent arthritis in animal models of RA (see, e.g., Jimi et al, 2004).

Anti-TNFα Therapy

Anti-TNFα therapy represents the market-leading therapies for RA, and is performed either with neutralising antibodies such as infliximab (Remicade® J&J and Schering Plough) and adalimumab (Humira®, Abbott) or decoy receptors such as etanercept (Enbrel® Amgen and Wyeth), both which represent validated and highly effective treatments for RA. Anti-TNF biologicals are already licensed for RA, Crohn's disease, and psoriasis. A number of other inflammatory and autoimmune disorders are also being investigated as potential targets. Other approaches to blocking the action of TNF include the pegylated anti-TNF fragment certolizumab (Cimzia®, UCB); inhibition of proximal signalling intermediates such as MAP kinase; interference with the synthesis of TNF via inhibition of TNFα converting enzyme (TACE); and inhibition of the metalloproteases responsible for cleaving TNF from the cell surface (see, e.g., Smolen et al, 2003; Mount et al, 2005).

Other Inhibitors of NFκB Activation

As described above, the binding of IL-1 and RANKL to their receptors also initiates a signalling cascade, which eventually leads to the activation of NFκB and subsequent inflammatory response. The efficacy of inhibitors of these ligands has been validated by the use of the IL-1 receptor antagonist anakinra (Kineret® Amgen) for the treatment of RA, and the progression of the monoclonal antibody against RANKL AMG-162 (Denosumab® Amgen) through to phase III clinical trials for osteoporosis (it is also in clinical trials for RA and psoriasis).

Other Common Inflammatory Diseases Mediated by TNFα

There are several other common inflammatory diseases in which TNFα has been shown to play a major role and in which TNFα inhibitors have found therapeutic use. These include inflammatory bowel disease (IBD) and psoriasis.

IBD is an inflammatory disorder of the gut affecting about 0.25% of the population in the western world, of which the two main forms are: ulcerative colitis (UC), in which the lining of the colon becomes inflamed and ulcerated; and Crohn's disease (CD), which can occur anywhere within the gastrointestinal tract, but most often the ileum, and commonly involves inflammation of the entire gut wall. Common symptoms of IBD are bloody diarrhea and abdominal pain.

Psoriasis is an inflammatory response of the skin affecting 1-3% of the population in the western world. The disease is characterised by raised, red, scaly plaques on the skin, which may be itchy and also cause significant psychological distress by their unsightly nature. A further complication of psoriasis is the development of psoriatic arthritis, an inflammatory arthritis of the joints, in up to 40% of patients, which develops on average 10 years after the first symptoms of skin disease are seen (see, e.g., Gottlieb, 2005).

As with RA, the aetiology of IBD and psoriasis are unknown and may involve a complex combination of infectious agents, environmental, and genetic factors, generating an inappropriate and prolonged inflammatory response.

Treatment of IBD and psoriasis has followed a similar pattern to that of RA, with the past use of immunoregulatory agents such as NSAIDs, methotrexate, cyclosporine, steroids, and antimetabolites such as 6-mercaptopurine for IBD (see, e.g., Korzenik et al, 2006) and methotrexate and cyclosporine for psoriasis (see, e.g., Gottlieb, 2005). The treatment of both has been revolutionised by the advent of biological agents, in particular those which block TNFα signalling. Etanercept is licensed for the treatment of psoriasis and psoriatic arthritis; both infliximab and adalimumab are licensed for psoriatic arthritis and IBD and are in late stage clinical trials for psoriasis.

Common Bone Diseases

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis may also arise in association with inflammatory diseases such as rheumatoid arthritis, endocrine diseases such as thyrotoxicosis, and with certain drug treatments such as treatment with glucocorticoids. However one of the most important factors in the pathogenesis of osteoporosis is heredity.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Bone involvement is a feature of many types of cancer. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common causes are multiple myeloma, breast carcinoma, and prostate carcinoma. The most common tumours associated with hypercalcaemia are multiple myeloma, breast carcinoma, and lung carcinoma.

RANKL signalling has been shown to play a major role in osteoclast over-activity and a consequent increase in bone loss (see, e.g., Tanaka et al, 2003; Roodman, 2006). The use of drugs which affect this pathway has been validated by the progression through to phase III/II clinical trials of the monoclonal antibody against RANKL AMG-162 (Denosumab® Amgen) for the treatment of osteoporosis/multiple myeloma.

As described previously, bone loss also plays a major role in the pathophysiology of rheumatoid arthritis and drugs which prevent activation of the signalling pathways described (e.g. TNFα blockers) are also able to prevent this bone loss.

Agents that Prevent Inflammation and/or Bone Loss

The inventors have identified a new class of compounds which, for example, prevent inflammation and/or bone loss, and thus may be used in the treatment of diseases with an inflammatory or autoimmune component, including, for example, rheumatoid arthritis, inflammatory bowel disease, psoriasis, and psoriatic arthritis; as well as diseases which involve bone loss, including, for example, bone loss associated with rheumatoid arthritis, osteoporosis, Paget's disease of bone, and multiple myeloma.

Without wishing to be bound by any particular theory, the inventors believe that this action may be via a mechanism that involves blocking TNFα and/or IL-1 and/or RANKL-signalling.

Biphenyl Sulfonamides

Greig et al., 2004 and Greig et al., 2006 describe a class of biphenyl alkyl sulfonamides, represented, for example, by 2',4'-difluoro-2-methyl-biphenyl-4-sulfonic acid (4-hydroxy-butyl)-amide (ABD295) (shown below), as anti-resorptive agents for the treatment of bone diseases.

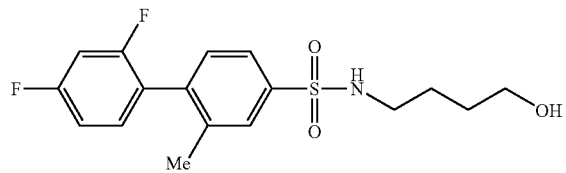

ABD295

The present inventors have identified a new a class of biphenyl-4-yl-sulfonic acid aryl amides, as defined herein, that have surprising and unexpected properties.

Specifically, the representative compounds are both orally active and prevent inflammation in the collagen-induced arthritis model.

Consequently, compounds within the new compound class have the potential to be orally active agents for the treatment of inflammatory diseases and/or for the treatment and/or prevention of bone loss.

SUMMARY OF THE INVENTION

One aspect of the invention pertains to certain aryl sulfonamides and related compounds (collectively referred to herein as "BPSAAA compounds"), as described herein.

Another aspect of the invention pertains to a composition comprising a BPSAAA compound as described herein and a pharmaceutically acceptable carrier or diluent.

Another aspect of the invention pertains to a method of inhibiting an inflammatory response, in vitro or in vivo, comprising contacting an immune system component with an effective amount of a BPSAAA compound, as described herein.

Another aspect of the invention pertains to a method of inhibiting cellular and/or molecular pathways leading to joint destruction, in vitro or in vivo, comprising contacting cells associated with an immune response with a therapeutically-effective amount of a BPSAAA compound, as described herein.

Another aspect of the invention pertains to a method of inhibiting osteoclast survival, formation, and/or activity, in vitro or in vivo, comprising contacting an osteoclast with an effective amount of a BPSAAA compound, as described herein.

Another aspect of the invention pertains to a method of inhibiting bone resorption, in vitro or in vivo, comprising contacting cells in the bone microenvironment with a therapeutically-effective amount of a BPSAAA compound, as described herein.

Another aspect of the present invention pertains to a BPSAAA compound as described herein for use in a method of treatment and/or prevention of the human or animal body by therapy.

Another aspect of the present invention pertains to use of a BPSAAA compound, as described herein, in the manufacture of a medicament for use in treatment and/or prevention.

Another aspect of the present invention pertains to a method of treatment and/or prevention comprising administering to a subject in need of treatment and/or prevention a therapeutically-effective amount of a BPSAAA compound, as described herein, preferably in the form of a pharmaceutical composition.

In one embodiment, the treatment and/or prevention is treatment and/or prevention of inflammation and/or joint destruction and/or bone loss.

In one embodiment, the treatment and/or prevention is treatment and/or prevention of disorders mediated by excessive and/or inappropriate and/or prolonged activation of the immune system.

In one embodiment, the treatment and/or prevention is treatment and/or prevention of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

In one embodiment, the treatment and/or prevention is treatment and/or prevention of disorders associated with bone loss, such as bone loss associated with excessive osteoclast activation in rheumatoid arthritis, osteoporosis, cancer associated bone disease, Paget's disease and the like.

Another aspect of the present invention pertains to a kit comprising (a) a BPSAAA compound, as described herein, preferably provided as a pharmaceutical composition and in a suitable container and/or with suitable packaging; and (b) instructions for use, for example, written instructions on how to administer the BPSAAA compound.

Another aspect of the present invention pertains to BPSAAA compounds obtainable by a method of synthesis as described herein, or a method comprising a method of synthesis as described herein.

Another aspect of the present invention pertains to BPSAAA compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
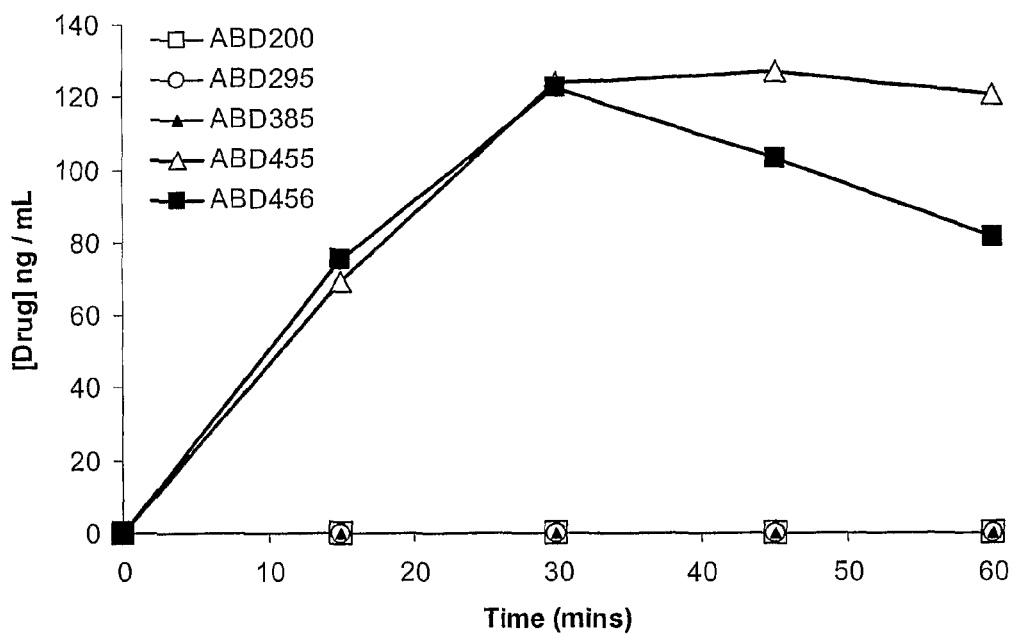
FIG. 1 is a graph showing blood serum levels (ng/mL) of the BPSAAA compounds ABD455 (Δ) and ABD456 (■) in comparison to the known biphenyl hydroxyalkyl sulfonamides ABD200 (□), ABD295 (○), ABD385 (▲) as a function of time (minutes) after oral administration (10 mg/kg). The graph shows that ABD455 and ABD456 are well absorbed whereas ABD200, ABD295 and ABD385 are not absorbed following oral dosage.

One aspect of the present invention pertains to compounds of the following formula, and pharmaceutically acceptable salts, hydrates, and solvates thereof (collectively referred to herein as "BPSAAA compounds"):

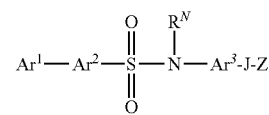

wherein:
$Ar^1$—$Ar^2$— is independently biphenyl-4-yl, and is optionally substituted;
—$R^N$ is independently —H or —$R^{NN}$;
—$R^{NN}$, if present, is independently $C_{1-6}$alkyl, phenyl-$C_{1-6}$alkyl-acyl, wherein each phenyl is optionally substituted;
—$Ar^3$— is independently 1,3-phenylene or 1,4-phenylene, and is optionally substituted;
either:
—Z is independently —OH or —O—W; and
-J- is independently —$R^{alk}$—;
or:
—Z is independently -Q; and
-J- is independently a covalent bond or —$R^{alk}$—;
wherein:
—$R^{alk}$—, if present, is independently saturated aliphatic $C_{1-5}$alkylene, and is optionally substituted;
—W, if present, is independently:
—$R^{E1}$,
—C(=O)—$R^{E2}$,
—C(=O)—O—$R^{E3}$,
—C(=O)—O—S(=O)$_2$O$R^{E4}$,
—C(=O)—(CH$_2$)$_n$—C(=O)O$R^{E5}$,
—C(=O)—(CH$_2$)$_n$—N$R^{NE1}R^{NE2}$,
—C(=O)—(CH$_2$)$_n$—N$R^{NE3}$—C(=O)$R^{E6}$,
—C(=O)—(CH$_2$)$_n$—C(=O)—N$R^{NE4}R^{NE5}$, or
—P(=O)(O$R^{E7}$)(O$R^{E8}$);
wherein:
each n is independently 1, 2, 3, or 4; and each of $R^{E1}$, $R^{E2}$, $R^{E3}$, $R^{E4}$, $R^{E5}$, $R^{E6}$, $R^{E7}$, $R^{E8}$, $R^{NE1}$, $R^{NE2}$, $R^{NE3}$, $R^{NE4}$, and $R^{NE5}$ is independently —H, $C_{1-3}$alkyl, phenyl, or —CH$_2$-phenyl;
wherein each phenyl is optionally substituted with one or more groups selected from: —F, —Cl, —Br, —I, —$R^{A3}$, —CF$_3$, —OH, —OR$^{A3}$, —OCF$_3$, —NHR$^{A3}$, —NR$^{A3}_2$, —C(=O)NH$_2$, —C(=O)NHR$^{A3}$, and —C(=O)NR$^{A3}_2$, wherein each $R^{A3}$ is independently $C_{1-4}$alkyl;

-Q, if present, is independently:
—C(=O)—OH, or
—C(=O)—OR$^{G1}$;

wherein:
$R^{G1}$ is independently —H, $C_{1-3}$alkyl, phenyl, or —CH$_2$-phenyl;
wherein each phenyl is optionally substituted with one or more groups selected from: —F, —Cl, —Br, —I, —$R^{A4}$, —CF$_3$, —OH, —OR$^{A4}$, —OCF$_3$, —NH$_2$, —NHR$^{A4}$, —NR$^{A4}_2$, —C(=O)NH$_2$, —C(=O)NHR$^{A4}$, and —C(=O)NR$^{A4}_2$, wherein each $R^{A4}$ is independently $C_{1-4}$alkyl.

Optional Provisos

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

In one embodiment, the proviso is that the compound is not a compound selected from: compounds (PP-01) through (PP-05), and salts, hydrates, and solvates thereof.

For example, a reference to a particular group of compounds "without the recited proviso regarding compounds (PP-01) through (PP-05)" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

In one or more aspects of the present invention (e.g., compounds for use in therapy, use of compounds in the manufacture of a medicament, methods of treatment, etc.), the compounds are optionally as defined herein, with the proviso regarding compounds (PP-01) through (PP-05).

The Group Ar$^1$—Ar$^2$—: Biphenyl-4-yl

In one embodiment, Ar$^1$—Ar$^2$— is independently biphenyl-4-yl, and is optionally substituted, for example, with one or more ring substituents.

In one embodiment, Ar$^1$—Ar$^2$— is independently a group of the following formula:

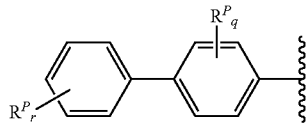

wherein:

| # | Structure | Name | Registry No. |
|---|-----------|------|--------------|
| PP-01 | ![structure] | 4-(4'-Acetylamino-biphenyl-4-sulfonylamino)-3-methyl-benzoic acid | 950020-41-4 |
| PP-02 | ![structure] | 4-(Biphenyl-4-sulfonylamino)-benzoic acid ethyl ester | 928143-63-9 |
| PP-03 | ![structure] | 4-(4'-Methoxy-biphenyl-4-sulfonylamino)-benzoic acid | 885269-91-0 |
| PP-04 | ![structure] | 4-(4'-Chloro-biphenyl-4-sulfonylamino)-benzoic acid | 885269-88-5 |
| PP-05 | ![structure] | 4-(4'-Methyl-biphenyl-4-sulfonylamino)-benzoic acid | 885269-85-2 |

In one or more aspects of the present invention (e.g., compounds for use in therapy, use of compounds in the manufacture of a medicament, methods of treatment, etc.), the compounds are optionally as defined herein; but without the proviso regarding compounds (PP-01) through (PP-05).

q is independently 0, 1, 2, 3, or 4;
r is independently 0, 1, 2, 3, 4, or 5; and
each $R^P$ is independently a ring substituent.

In one embodiment, q is independently 0, 1, or 2.
In one embodiment, q is independently 1 or 2.

In one embodiment, q is independently 0.
In one embodiment, q is independently 1.
In one embodiment, q is independently 2.
In one embodiment, r is independently 0, 1, or 2.
In one embodiment, r is independently 1 or 2.
In one embodiment, r is independently 0.
In one embodiment, r is independently 1.
In one embodiment, r is independently 2.
In one embodiment, Ar¹—Ar²— is independently a group of the following formula:

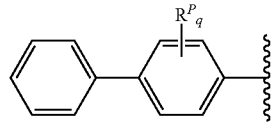

In one embodiment, Ar¹—Ar²— is independently a group of the following formula:

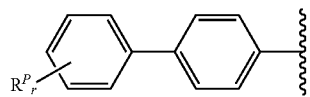

The Group Ar¹—Ar²—: 4'-Substituted Biphenyl-4-yl

In one embodiment, Ar¹—Ar²— is independently a group of the following formula:

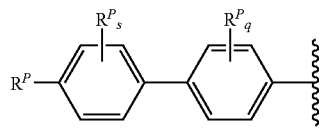

wherein:
s is independently 0, 1, 2, 3, or 4;
q is as defined above; and
each $R^P$ is independently a ring substituent.

In one embodiment, s is independently 0 or 1.
In one embodiment, s is independently 0.
In one embodiment, s is independently 1.
In one embodiment, Ar¹—Ar²— is independently a group of the following formula:

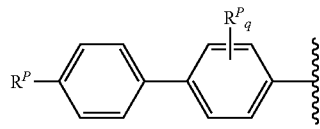

In one embodiment, Ar¹—Ar²— is independently a group of the following formula:

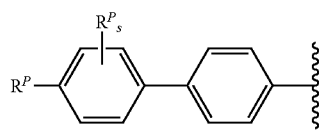

In one embodiment, Ar¹—Ar²— is independently a group of the following formula:

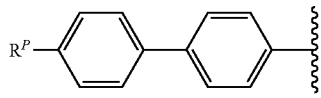

The Group Ar¹—Ar²—: 3'-Substituted Biphenyl-4-yl

In one embodiment, Ar¹—Ar²— is independently a group of the following formula:

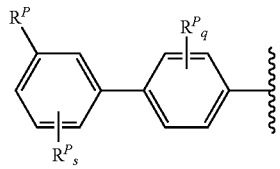

wherein:
s is as defined above;
q is as defined above; and
each $R^P$ is independently a ring substituent.

In one embodiment, Ar¹—Ar²— is independently a group of the following formula:

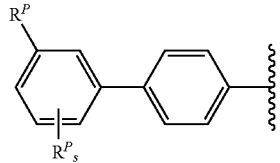

In one embodiment, Ar¹—Ar²— is independently a group of the following formula:

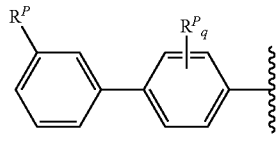

In one embodiment, Ar¹—Ar²— is independently a group of the following formula:

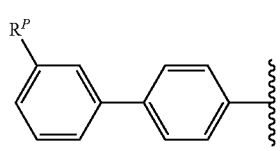

The Group Ar¹—Ar²—: 3',4'-Disubstituted Biphenyl-4-yl

In one embodiment, Ar¹—Ar²— is independently a group of the following formula:

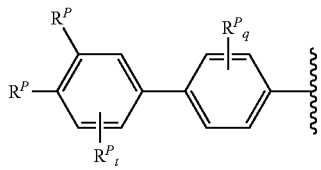

wherein:
q is as defined above;
t is independently 0, 1, 2, or 3; and
each $R^P$ is independently a ring substituent.

In one embodiment, t is independently 0 or 1.
In one embodiment, t is independently 0.
In one embodiment, t is independently 1.

In one embodiment, Ar¹—Ar²— is independently a group of the following formula:

In one embodiment, Ar¹—Ar²— is independently a group of the following formula:

The Group Ar¹—Ar²—: 2'-Substituted Biphenyl-4-yl

In one embodiment, Ar¹—Ar²— is independently a group of the following formula:

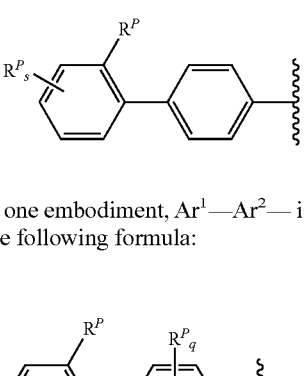

wherein:
q is as defined above;
s is as defined above; and
each $R^P$ is independently a ring substituent.

In one embodiment, Ar¹—Ar²— is independently a group of the following formula:

In one embodiment, Ar¹—Ar²— is independently a group of the following formula:

In one embodiment, Ar¹—Ar²— is independently a group of the following formula:

The Group Ar¹—Ar²—: 2',4'-Disubstituted Biphenyl-4-yl

In one embodiment, Ar¹—Ar²— is independently a group of the following formula:

wherein:
q is as defined above;
t is as defined above; and
each $R^P$ is independently a ring substituent.

In one embodiment, Ar¹—Ar²— is independently a group of the following formula:

In one embodiment, Ar$^1$—Ar$^2$— is independently a group of the following formula:

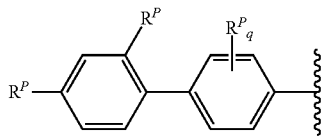

In one embodiment, Ar$^1$—Ar$^2$— is independently a group of the following formula:

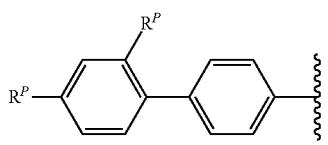

The Group Ar$^1$—Ar$^2$—: 2,2',4'-Trisubstituted Biphenyl-4-yl

In one embodiment, Ar$^1$—Ar$^2$— is independently a group of the following formula:

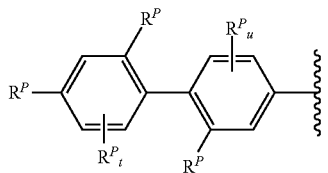

wherein:
t is as defined above;
u is independently 0, 1, 2, or 3; and
each R$^P$ is independently a ring substituent.

In one embodiment, Ar$^1$—Ar$^2$— is independently a group of the following formula:

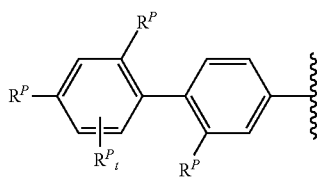

In one embodiment, Ar$^1$—Ar$^2$— is independently a group of the following formula:

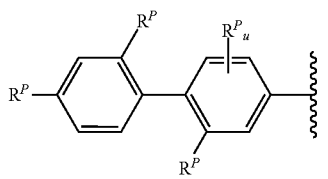

In one embodiment, Ar$^1$—Ar$^2$— is independently a group of the following formula:

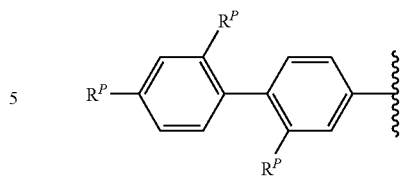

The Group Ar$^1$—Ar$^2$—: Unsubstituted Biphenyl-4-yl

In one embodiment, Ar$^1$—Ar$^2$— is independently a group of the following formula:

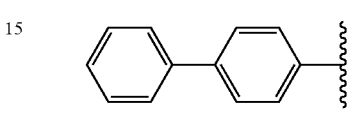

The Group R$^N$

The sulfonamide nitrogen substituent, —R$^N$, is independently —H or —R$^{NN}$.

In one embodiment, —R$^{NN}$, if present, is independently C$_{1-6}$alkyl, phenyl-C$_{1-6}$alkyl, C$_{1-6}$alkyl-acyl, phenyl-C$_{1-6}$alkyl-acyl, wherein each phenyl is optionally substituted.

In one embodiment, —R$^{NN}$, if present, is independently C$_{1-6}$alkyl, phenyl-C$_{1-6}$alkyl, C$_{1-6}$alkyl-acyl, phenyl-C$_{1-6}$alkyl-acyl, wherein each phenyl is optionally substituted with one or more groups selected from: —F, —Cl, —Br, —I, —R$^{A1}$, —CF$_3$, —OH, —OR$^{A1}$, —OCF$_3$, —NH$_2$, —NHR$^{A1}$, —NR$^{A1}_2$, —C(=O)NH$_2$, —C(=O)NHR$^{A1}$, and —C(=O)NR$^{A1}_2$, wherein each R$^{A1}$ is independently C$_{1-4}$alkyl.

In one embodiment, —R$^N$ is independently —H or C$_{1-6}$alkyl.

In one embodiment, —R$^N$ is independently —H, -Me, or -Et.

In one embodiment, —R$^N$ is independently —H.

The Group —Ar$^3$—

The group —Ar$^3$— is independently 1,3-phenylene or 1,4-phenylene, and is optionally substituted, for example, with one or more ring substituents.

In one embodiment, —Ar$^3$— is independently 1,3-phenylene, and is optionally substituted, for example, with one or more ring substituents.

In one embodiment, —Ar$^3$— is independently 1,4-phenylene, and is optionally substituted, for example, with one or more ring substituents.

In the following formulae, the asterisk (*) denotes the connection to the —N(R$^N$)— group and the pound sign (#) denotes the connection to the -J- group:

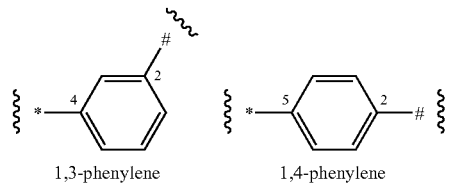

1,3-phenylene    1,4-phenylene

Substituents on —Ar$^3$—

In one embodiment, —Ar$^3$— is independently unsubstituted.

(For the avoidance of doubt, "unsubstituted" in this context means unsubstituted other than by —NR$^N$—S(=O)$_2$—Ar$^2$—Ar$^1$ and -J-Z.)

In one embodiment, —Ar³— is independently unsubstituted or substituted with one or more ring substituents, for example, unsubstituted or substituted with one or more substituents, —$R^{AR3}$, wherein each —$R^{AR3}$ is independently a ring substituent.

The Group -J-Z

In one embodiment:
either:
—Z is independently —OH or —O—W; and
-J- is independently —$R^{alk}$—;
or:
—Z is independently -Q; and
-J- is independently a covalent bond or —$R^{alk}$—.

In one embodiment:
—Z is independently —OH or —O—W; and
-J- is independently —$R^{alk}$—.

In one embodiment:
—Z is independently —OH; and
-J- is independently —$R^{alk}$—.

In one embodiment:
—Z is independently -Q; and
-J- is independently a covalent bond or —$R^{alk}$—.

In one embodiment:
—Z is independently -Q; and
-J- is independently a covalent bond.

In one embodiment:
—Z is independently -Q; and
-J- is independently —$R^{alk}$—.

The Group —$R^{alk}$—

The group, —$R^{alk}$—, if present, is independently saturated aliphatic $C_{1-5}$alkylene, and is optionally substituted.

In one embodiment, —$R^{alk}$—, if present, is independently saturated aliphatic $C_{1-4}$alkylene, and is optionally substituted.

In one embodiment, —$R^{alk}$—, if present, is independently saturated aliphatic $C_{1-3}$alkylene, and is optionally substituted.

In one embodiment, —$R^{alk}$—, if present, is independently —$(CH_2)_z$—, wherein z is independently 1, 2, 3, 4, or 5.

In one embodiment, —$R^{alk}$—, if present, is independently —$(CH_2)_z$—, wherein z is independently 1, 2, 3, or 4.

In one embodiment, —$R^{alk}$—, if present, is independently —$CH_2$—, —$(CH_2)_2$—, or —$(CH_2)_3$—.

In one embodiment, —$R^{alk}$—, if present, is independently —$CH_2$— or —$(CH_2)_2$—.

In one embodiment, —$R^{alk}$—, if present, is independently —$CH_2$—.

In one embodiment, —$R^{alk}$—, if present, is independently —$(CH_2)_2$—.

Substituents on —$R^{alk}$—

In one embodiment, —$R^{alk}$—, if present, is independently unsubstituted.

(For the avoidance of doubt, "unsubstituted" in this context means unsubstituted other than by —$Ar^3$—$NR^N$—$S(=O)_2$—$Ar^2$—$Ar^1$ and —Z.)

In one embodiment, —$R^{alk}$—, if present, is independently unsubstituted or substituted with one or more substituents.

In one embodiment, —$R^{alk}$—, if present, is independently unsubstituted or substituted with one or more substituents, —$R^{AA}$.

(For the avoidance of doubt, if —$R^{alk}$— includes a —$CF_3$ group, the carbon atom of the —$CF_3$ group is part of the saturated aliphatic alkylene group, and each of the three fluorine groups is a substituent on it. For example, the group —$CH_2CH(CF_3)$— is a $C_{1-3}$alkylene group bearing three substituents, each of which is —F.)

In one embodiment, each substituent —$R^{AA}$, if present, is independently: —F, —Cl, —Br, —I, —OH, —$OR^{A2}$, —$OCF_3$, —$NH_2$, —$NHR^{A2}$, —$NR^{A2}_2$, —$C(=O)NH_2$, —$C(=O)NHR^{A2}$, or —$C(=O)NR^{A2}_2$; wherein each $R^{A2}$ is independently $C_{1-4}$alkyl.

In one embodiment, each substituent —$R^{AA}$, if present, is independently: —F, —Cl, —Br, —I, —OH, —OMe, —OEt, —$OCF_3$, —$NH_2$, —NHMe, —NHEt, —$NMe_2$, —$NEt_2$, —$C(=O)NH_2$, —C(=O)NHMe, —C(=O)NHEt, —$C(=O)NMe_2$, or —$C(=O)NEt_2$.

In one embodiment, each substituent —$R^{AA}$, if present, is independently: —F, —Cl, —Br, —I, —OH, —OMe, —$OCF_3$, —$NH_2$, —NHMe, —$NMe_2$, —$C(=O)NH_2$, —C(=O)NHMe, or —$C(=O)NMe_2$.

In one embodiment, each substituent —$R^{AA}$, if present, is independently: —F, —Cl, —Br, —I, —OH, or —OMe.

In one embodiment, each substituent —$R^{AA}$, if present, is independently: —F, —Cl, —$CF_3$, or —$OCF_3$.

In one embodiment, each substituent —$R^{AA}$, if present, is independently: —F.

The Group W

The group W, if present, is independently:
—$R^{E1}$,
—$C(=O)$—$R^{E2}$,
—$C(=O)$—O—$R^{E3}$,
—$C(=O)$—O—$S(=O)_2OR^{E4}$,
—$C(=O)$—$(CH_2)_n$—$C(=O)OR^{E5}$,
—$C(=O)$—$(CH_2)_n$—$NR^{NE1}R^{NE2}$,
—$C(=O)$—$(CH_2)_n$—$NR^{NE3}$—$C(=O)R^{E6}$,
—$C(=O)$—$(CH_2)_n$—$C(=O)$—$NR^{NE4}R^{NE5}$, or
—$P(=O)(OR^{E7})(OR^{E8})$;

wherein:
each n is independently 1, 2, 3, or 4; and each or $R^{E1}$, $R^{E2}$, $R^{E3}$, $R^{E4}$, $R^{E5}$, $R^{E6}$, $R^{E7}$, $R^{E8}$, $R^{NE1}$, $R^{NE2}$, $R^{NE3}$, $R^{NE4}$, and $R^{NE5}$ is independently —H, $C_{1-3}$alkyl, phenyl, or —$CH_2$-phenyl;

wherein each phenyl is optionally substituted with one or more groups selected from: —F, —Cl, —Br, —I, —$R^{43}$, —$CF_3$, —OH, —$OR^{43}$, —$NH_2$, —$NHR^{43}$, —$NR^{43}_2$, —$C(=O)NH_2$, —$C(=O)NHR^{43}$, and —$C(=O)NR^{43}_2$ wherein each $R^{43}$ is independently $C_{1-4}$alkyl.

In one embodiment, W, if present, is independently —H, —$R^{E1}$, or —$C(=O)$—$R^{E2}$.

In one embodiment, each of $R^{E1}$, $R^{E2}$, $R^{E3}$, $R^{E4}$, $R^{E5}$, $R^{E6}$, $R^{E7}$, and $R^{E8}$, if present, is independently: —H, $C_{1-3}$alkyl, phenyl, or —$CH_2$-phenyl.

In one embodiment, each of $R^{E1}$, $R^{E2}$, $R^{E3}$, $R^{E4}$, $R^{E5}$, $R^{E6}$, $R^{E7}$, and $R^{E8}$, if present, is independently —H or $C_{1-3}$alkyl.

In one embodiment, each of $R^{E1}$, $R^{E2}$, $R^{E3}$, $R^{E4}$, $R^{E5}$, $R^{E6}$, $R^{E7}$, and $R^{E8}$, if present, is independently —H, -Me, or -Et.

The Group Q

In one embodiment, Q, if present, is independently:
—C(=O)—OH, or
—$C(=O)$—$OR^{G1}$;
wherein $R^{G1}$ is independently —H, $C_{1-3}$alkyl, phenyl, or —$CH_2$-phenyl;
wherein each phenyl is optionally substituted with one or more groups selected from: —F, —Cl, —Br, —I, —$R^{44}$, —$CF_3$, —OH, —$OR^{44}$, —$OCF_3$, —$NH_2$, —$NHR^{44}$, —$NR^{44}_2$, —$C(=O)NH_2$, —$C(=O)NHR^{44}$, and —$C(=O)NR^{44}_2$, wherein each $R^{44}$ is independently $C_{1-4}$alkyl.

In one embodiment, $R^{G1}$, if present, is independently —H, $C_{1-3}$alkyl, phenyl, or —$CH_2$-phenyl.

In one embodiment, $R^{G1}$, if present, is independently —H or $C_{1-3}$alkyl.

In one embodiment, $R^{G1}$, if present, is independently —H, -Me, or -Et.

Ring Substituents

In one embodiment, each ring substituent (e.g., $R^P$), if present, is independently:
- —F, —Cl, —Br, —I,
- —$R^{D1}$,
- —$CF_3$,
- —OH,
- —$OR^{D1}$,
- —$OCF_3$,
- —SH,
- —$SR^{D1}$,
- —CN,
- —$NO_2$,
- —$NH_2$, —$NHR^{D1}$, —$NR^{D1}{}_2$, —$NR^{N1}R^{N2}$,
- —C(=O)OH,
- —C(=O)$OR^{D1}$,
- —C(=O)$NH_2$, —C(=O)$NHR^{D1}$, —C(=O)$NR^{D1}{}_2$, —C(=O)$NR^{N1}R^{N2}$,
- —NHC(=O)$R^{D1}$, —$NR^{D1}$C(=O)$R^{D1}$,
- —NHC(=O)$OR^{D1}$, —$NR^{D1}$C(=O)$OR^{D1}$,
- —OC(=O)$R^{D1}$,
- —C(=O)$R^D$,
- —NHC(=O)$NH_2$, —NHC(=O)$NHR^{D1}$, —NHC(=O)$NR^{D1}{}_2$, —NHC(=O)$NR^{N1}R^{N2}$,
- —$NR^{D1}$C(=O)$NH_2$, —$NR^{D1}$C(=O)$NHR^{D1}$, —$NR^{D1}$C(=O)$NR^{D1}{}_2$, —$NR^{D1}$C(=O)$NR^{N1}R^{N2}$,
- —$NHSO_2R^{D1}$, —$NR^{D1}SO_2R^{D1}$,
- —$SO_2NH_2$, —$SO_2NHR^{D1}$, —$SO_2NR^{D1}{}_2$, —$SO_2NR^{N1}R^{N2}$,
- —$SO_2R^{D1}$,
- —$OSO_2R^{D1}$,
- —P(=O)(OH)$_2$, —P(=O)(OH)($OR^{D1}$), —P(=O)($OR^{D1}$)$_2$,
- —OP(=O)(OH)$_2$, —OP(=O)(OH)($OR^{D1}$), —OP(=O)($OR^{D1}$)$_2$,
- =O,
- =$NR^{D1}$,
- =NOH, or
- =$NOR^{D1}$;

and additionally, two ring adjacent ring substituents, if present, may together form a group —O-$L^1$-O—;

wherein:
- $L^1$ is independently saturated aliphatic $C_{1-3}$alkylene;
- in each group —$NR^{N1}R^{N2}$, $R^{N1}$ and $R^{N2}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O; and
- each —$R^{D1}$ is independently —$R^{D2}$, —$R^{D3}$, —$R^{D4}$, $R^{D5}$, —$R^{D6}$, -$L^2$-$R^{D3}$, -$L^2$-$R^{D4}$, -$L^2$-$R^{D5}$, or -$L^2$-$R^{D6}$;

wherein:
- each —$R^{D2}$ is independently saturated aliphatic $C_{1-6}$alkyl;
- each —$R^{D3}$ is independently phenyl;
- each —$R^{D4}$ is independently $C_{5-6}$heteroaryl;
- each —$R^{D5}$ is independently $C_{3-6}$cycloalkyl or $C_{3-6}$cycloalkenyl;
- each —$R^{D6}$ is independently non-aromatic $C_{3-6}$heterocyclyl; and
- each -$L^2$- is independently saturated aliphatic $C_{1-3}$alkylene;

and wherein:
- each $C_{1-6}$alkyl, phenyl, $C_{5-6}$heteroaryl, $C_{3-6}$cycloalkyl, $C_{3-6}$cycloalkenyl, $C_{3-6}$heterocyclyl, and $C_{1-3}$alkylene is optionally substituted with one or more substituents selected from:
  - —F, —Cl, —Br, —I;
  - —$R^{F1}$;
  - —$CF_3$;
  - —OH;
  - —$OR^{F1}$;
  - —$OCF_3$;
  - —SH;
  - —$SR^{F1}$;
  - —CN;
  - —$NO_2$;
  - —$NH_2$, —$NHR^{F1}$, —$NR^{F1}{}_2$, —$NR^{N3}R^{N4}$;
  - —C(=O)OH;
  - —C(=O)$OR^{F1}$;
  - —C(=O)$NH_2$, —C(=O)$NHR^{F1}$, —C(=O)$NR^{F1}{}_2$, —C(=O)$NR^{N4}$
  - -$L^3$-OH, -$L^3$-$OR^{F1}$,
  - -$L^3$-$NH_2$, -$L^3$-$NHR^{F1}$, -$L^3$-$NR^{F1}{}_2$, or -$L^3$-$NR^{N3}R^{N4}$;

wherein:
- each —$R^{F1}$ is independently saturated aliphatic $C_{1-4}$alkyl;
- each -$L^3$- is independently saturated aliphatic $C_{2-5}$alkylene; and
- in each group —$NR^{N3}R^{N4}$, $R^{N3}$ and $R^{N4}$, taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each —$R^{D1}$, if present, is independently —$R^{D2}$, —$R^{D3}$, or -$L^2$-$R^{D3}$.

In one embodiment, each -$L^1$-, if present, is independently —$CH_2$—.

In one embodiment, each —$R^{D1}$, if present, is independently —$R^{D8}$.

Each —$R^{D8}$, if present, is independently —$R^{D2}$, —$R^{D3}$, or —$CH_2$-$R^{D3}$.

In one embodiment, each —$R^{D1}$, if present, is independently —$R^{D9}$.

Each —$R^{D9}$, if present, is independently saturated aliphatic $C_{1-3}$alkyl.

In one embodiment, each —$NR^{N1}R^{N2}$, if present, is independently —$NR^{NA}R^{NB}$.

In one embodiment, each —$NR^{N3}R^{N4}$, if present, is independently —$NR^{NA}R^{NB}$.

Each —$NR^{NA}R^{NB}$, if present, is independently pyrrolidino, imidazolidino, N—($C_{1-3}$alkyl)-imidazolidino, pyrazolidino, N—($C_{1-3}$alkyl)-pyrazolidino, piperidino, N—($C_{1-3}$alkyl)-piperidino, piperizino, morpholino, azepino, diazepino, or N—($C_{1-3}$alkyl)-diazepino.

In one embodiment, each ring substituent, if present, is independently:
- —F, —Cl, —Br, —I, —$R^{D8}$, —$R^{D8}$, —$CF_3$, —OH, —$OR^{D8}$, —$OCF_3$, —$SR^{D8}$, —CN, —$NO_2$, —$NH_2$, —$NHR^{D8}$, —$NR^{D8}{}_2$, —$NR^{N3}R^{N4}$, —C(=O)OH, —C(=O)$OR^{D8}$, —C(=O)$NH_2$, —C(=O)$NHR^{D8}$, —C(=O)$NR^{D8}{}_2$, —C(=O)$NR^{N3}R^{N4}$, —NHC(=O)$R^{D8}$, —$NR^{D8}$C(=O)$R^{D8}$, —OC(=O)$R^{D8}$, —$SO_2NH_2$, —$SO_2R^{D8}$, —P(=O)($OR^{D8}$)$_2$.

In one embodiment, each ring substituent, if present, is independently:
- —F, —Cl, —Br, —I, —$R^{D8}$, —$R^{D8}$, —$CF_3$, —OH, —$OR^{D8}$, —$OCF_3$, —$SR^{D8}$, —$NO_2$, —$NH_2$, —$NHR^{D8}$, —$NR^{D8}{}_2$, —NR$^{N3}$R$^{N4}$, —C(=O)OH, —C(=O)OR$^{D8}$, —C(=O)NH$_2$, —C(=O)NHR$^{D8}$, —C(=O)NR$^{D8}_2$, —C(=O)NR$^{N3}$R$^{N4}$, —NHC(=O)R$^{D8}$, —NR$^{D8}$C(=O)R$^{D8}$, —OC(=O)R$^{D8}$, —SO$_2$NH$_2$, —SO$_2$R$^{D8}$, —P(=O)(OR$^{D8}$)$_2$.

In one embodiment, each ring substituent, if present, is independently:
—F, —Cl, —Br, —I, —R$^{D8}$, —R$^{D8}$, —CF$_3$, —OH, —OR$^{D8}$, —OCF$_3$, —SR$^{D8}$, —CN, —NO$_2$, —NH$_2$, —NHR$^{D8}$, —NR$^{D8}_2$, —C(=O)OH, or —C(=O)OR$^{D8}$.

In one embodiment, each ring substituent, if present, is independently:
—F, —Cl, —Br, —I, —R$^{D8}$, —R$^{D8}$, —CF$_3$, —OH, —OR$^{D8}$, —OCF$_3$, —SR$^{D8}$, —NO$_2$, —NH$_2$, —NHR$^{D8}$, —NR$^{D8}_2$, —C(=O)OH, or —C(=O)OR$^{D8}$.

In one embodiment, each ring substituent, if present, is independently:
—F, —Cl, —Br, —I, —R$^{D9}$, —CF$_3$, —OH, —OR$^{D9}$, —OCF$_3$, —CN, —NO$_2$, —NH$_2$, —NHR$^{D9}$, or —NR$^{D9}_2$.

In one embodiment, each ring substituent, if present, is independently:
—F, —Cl, —Br, —I, —R$^{D9}$, —CF$_3$, —OH, —OR$^{D9}$, —OCF$_3$, —NO$_2$, —NH$_2$, —NHR$^{D9}$, or —NR$^{D9}_2$.

In one embodiment, each ring substituent, if present, is independently:
—F, —Cl, —Br, —I, -Me, —CF$_3$, —OH, —OMe, —OCF$_3$, —CN, —NO$_2$, —NH$_2$, —NHMe, or —NMe$_2$.

In one embodiment, each ring substituent, if present, is independently:
—F, —Cl, —Br, —I, -Me, —CF$_3$, —OH, —OMe, —OCF$_3$, —NO$_2$, —NH$_2$, —NHMe, or —NMe$_2$.

In one embodiment, each ring substituent, if present, is independently:
—F, —Cl, —Br, -Me, —CF$_3$, —OMe, —OCF$_3$, —CN, or —NO$_2$.

In one embodiment, each ring substituent, if present, is independently:
—F, —Cl, —Br, -Me, —CF$_3$, —OMe, —OCF$_3$, or —NO$_2$.

In one embodiment, each ring substituent, if present, is independently:
—F, —Cl, —Br, -Me, —CF$_3$, —OMe, or —OCF$_3$.

In one embodiment, each ring substituent, if present, is independently —F, —Cl, —Br, or —I.

In one embodiment, each ring substituent, if present, is independently —F, —Cl, or —Br.

In one embodiment, each ring substituent, if present, is independently —F or —Cl.

In one embodiment, each ring substituent, if present, is independently —F or —Br.

In one embodiment, each ring substituent, if present, is independently —F.

Combinations

All plausible and compatible combinations of the embodiments described above are explicitly disclosed herein, as if each plausible and compatible combination was individually and explicitly recited.

For example, in one preferred embodiment:
Ar$^1$—Ar$^2$— is independently a group of the following formula:

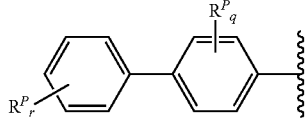

wherein:
q is independently 0, 1, or 2;
r is independently 0, 1, or 2; and
each R$^P$ is independently a ring substituent.
—Ar$^3$— is independently 1,3-phenylene or 1,4-phenylene, and is optionally substituted;
—Z is independently —OH or —O—W; and
-J- is independently —R$^{alk}$—.

For example, in one preferred embodiment:
Ar$^1$—Ar$^2$— is independently a group of the following formula:

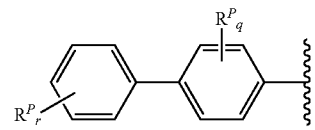

wherein:
q is independently 0, 1, or 2;
r is independently 0, 1, or 2; and
each R$^P$ is independently a ring substituent.
—Ar$^3$— is independently 1,3-phenylene or 1,4-phenylene, and is optionally substituted;
—Z is independently —OH; and
-J- is independently —CH$_2$— or —(CH$_2$)$_2$—.

For example, in one preferred embodiment:
Ar$^1$—Ar$^2$— is independently a group of the following formula:

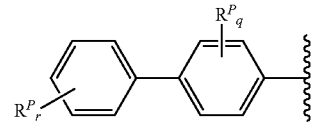

wherein:
q is independently 0, 1, or 2;
r is independently 0, 1, or 2; and
each R$^P$ is independently a ring substituent.
—Ar$^3$— is independently 1,3-phenylene or 1,4-phenylene, and is optionally substituted;
—Z is independently -Q;
-J- is independently a covalent bond; and
-Q is independently —C(=O)—OH or —C(=O)—OR$^{G1}$.

For example, in one preferred embodiment:
Ar$^1$—Ar$^2$— is independently a group of the following formula:

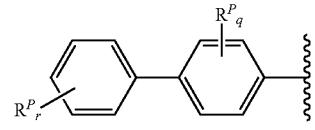

wherein:
q is independently 0, 1, or 2;
r is independently 0, 1, or 2; and
each R$^P$ is independently a ring substituent.
—Ar$^3$— is independently 1,3-phenylene or 1,4-phenylene, and is optionally substituted;
—Z is independently -Q;

-J- is independently —R$^{alk}$—; and
-Q is independently —C(=O)—OH or —C(=O)—OR$^{G1}$.
Specific Embodiments
In one embodiment, the compounds are selected from compounds of the following formulae and pharmaceutically acceptable salts, hydrates, and solvates thereof:
ABD445
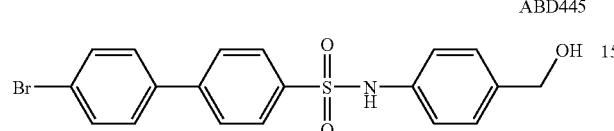
ABD446
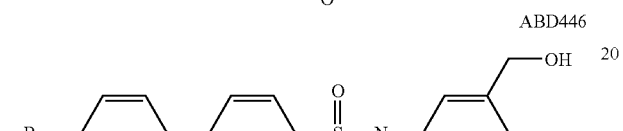
ABD451
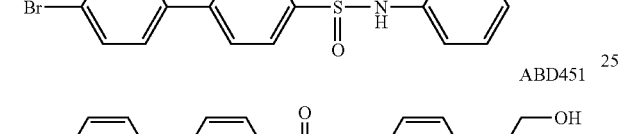
ABD455
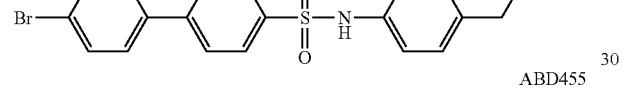
ABD456
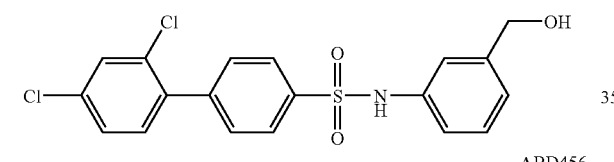
ABD465
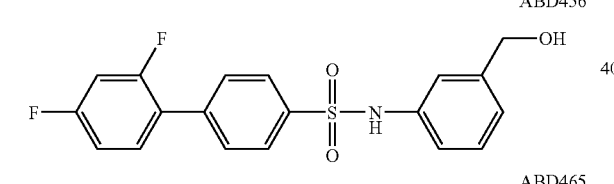
ABD466
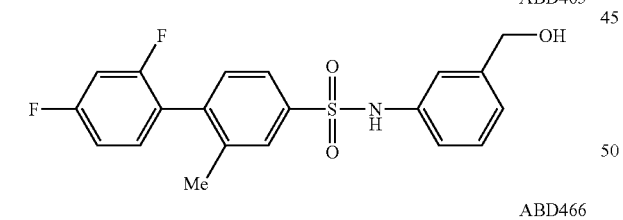
ABD499
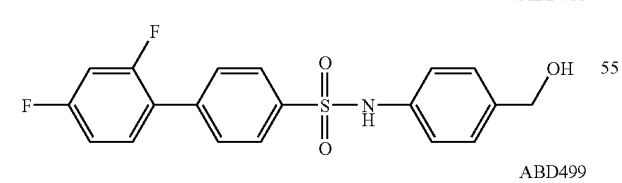
ABD500
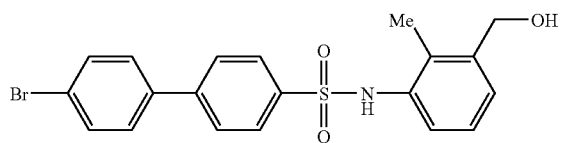
ABD510
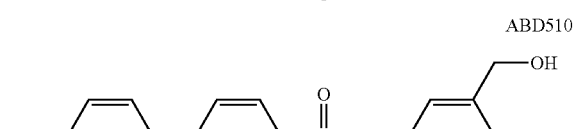
ABD512
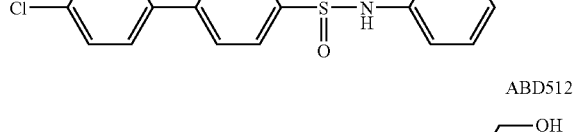
ABD514
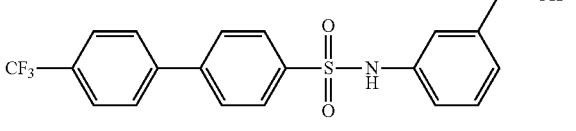
ABD515
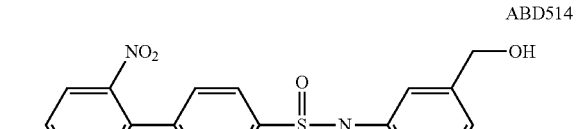
ABD520
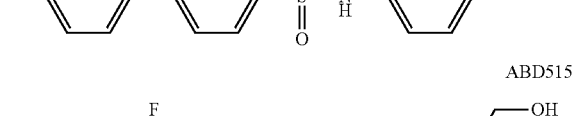
ABD523
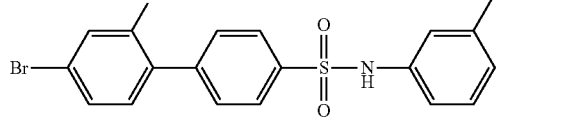
ABD525
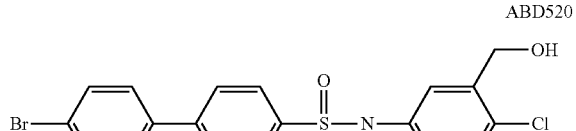
ABD527
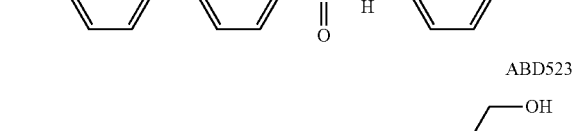

-continued
ABD528
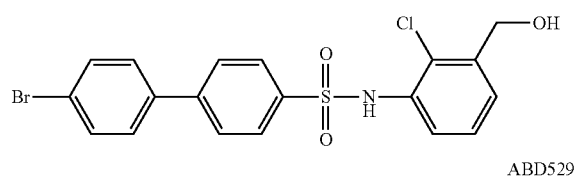
ABD529
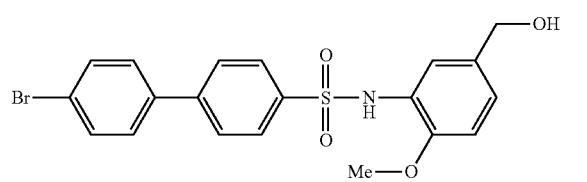
ABD530
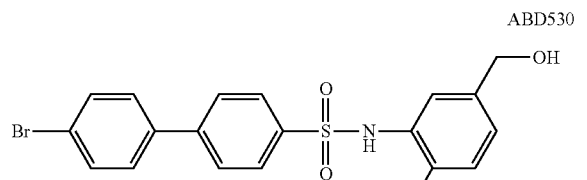
ABD545
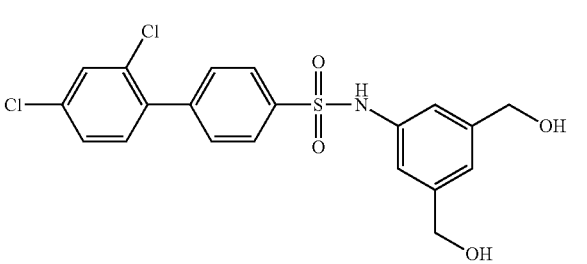
ABD547
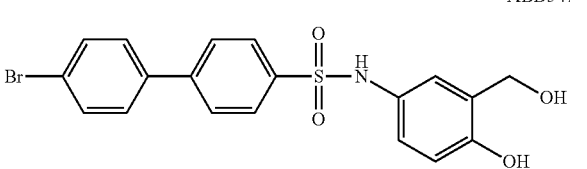
ABD550
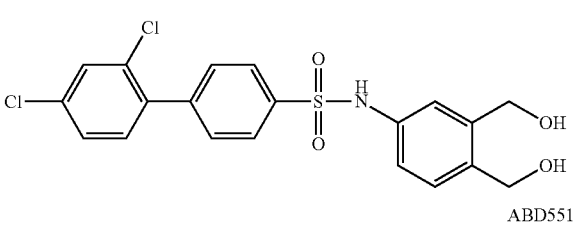
ABD551
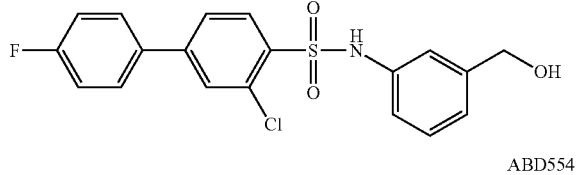
ABD554
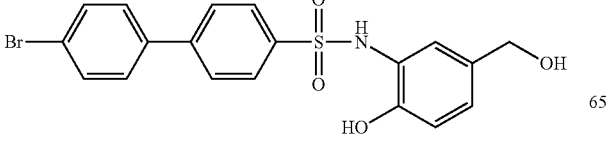
-continued
ABD559
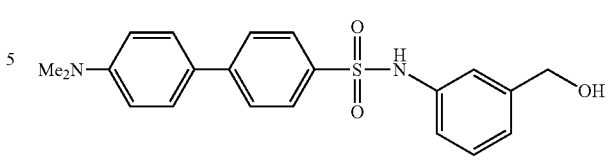
ABD565
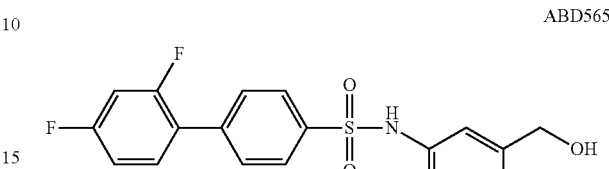
ABD568
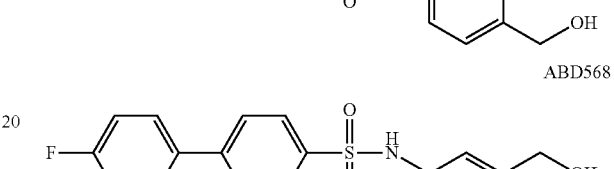
ABD575
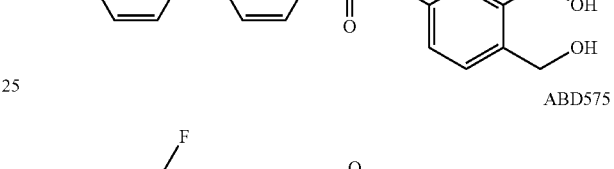
ABD576
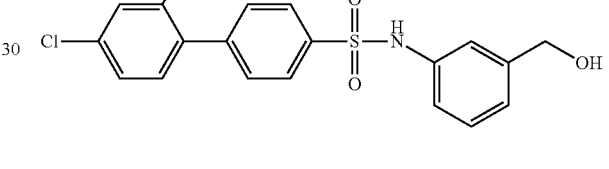
ABD577
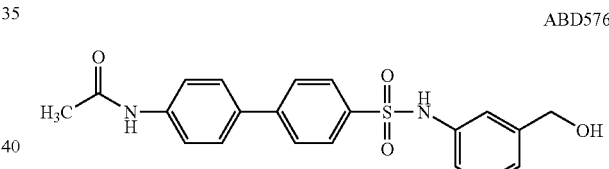
ABD578
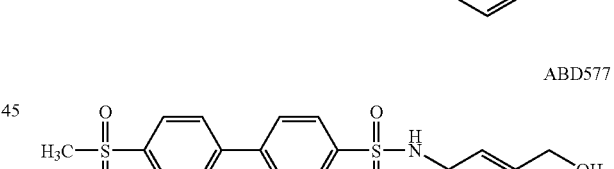
ABD579
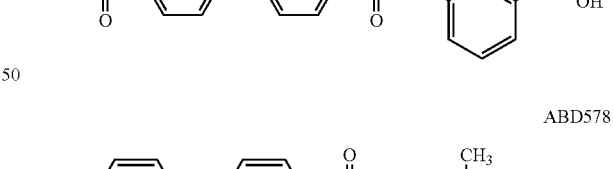

-continued
ABD585
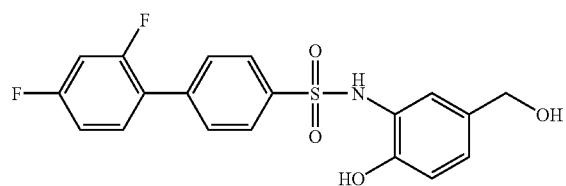
ABD587
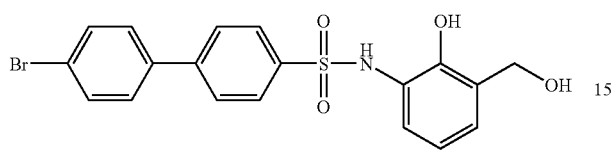
ABD588
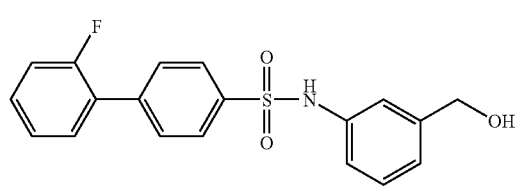
ABD589
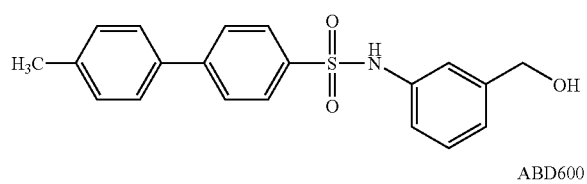
ABD600
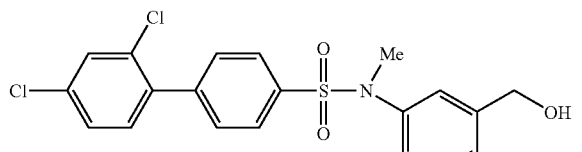
ABD601
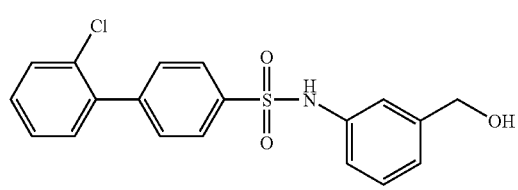
ABD625
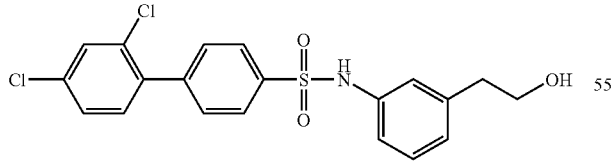
ABD628
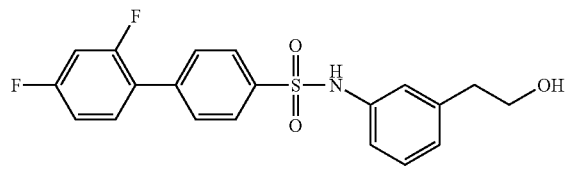
-continued
ABD630
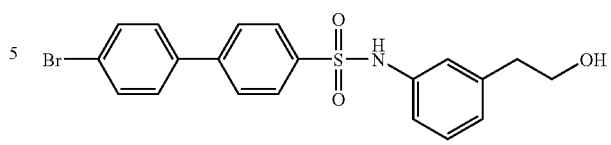
In one embodiment, the compounds are selected from compounds of the following formulae and pharmaceutically acceptable salts, hydrates, and solvates thereof:
ABD543
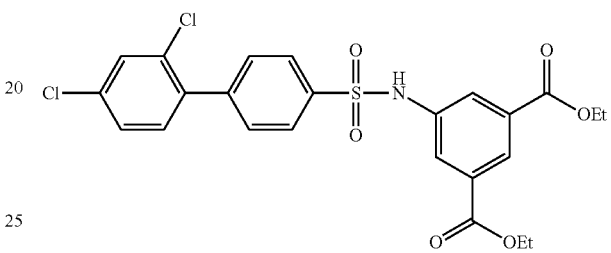
ABD544
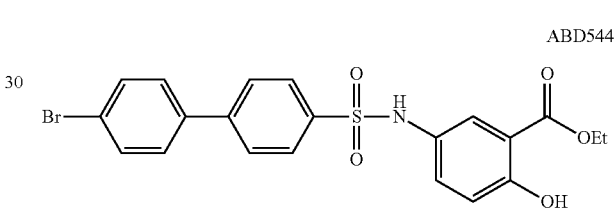
ABD549
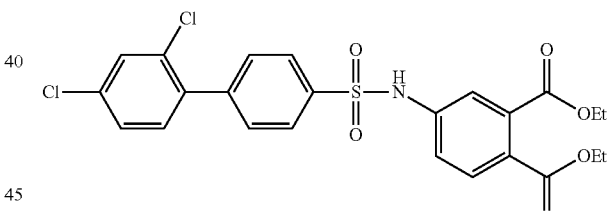
ABD553
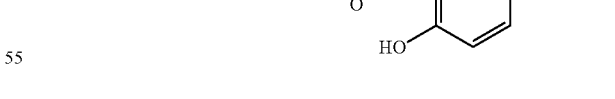
ABD562
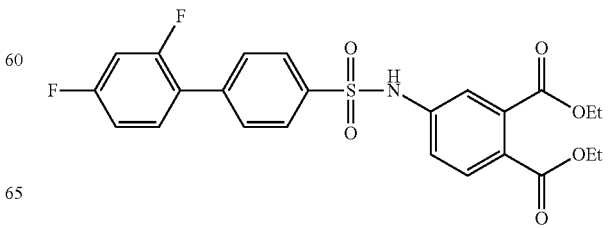

ABD566
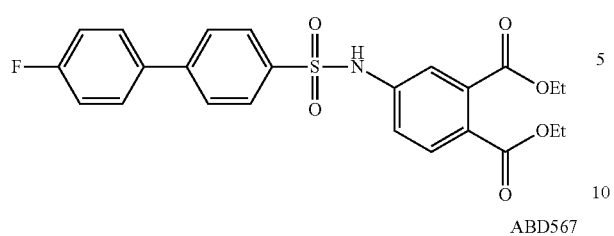

ABD567
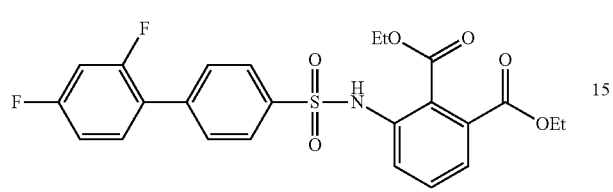

ABD583
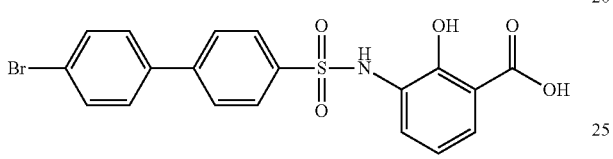

ABD584
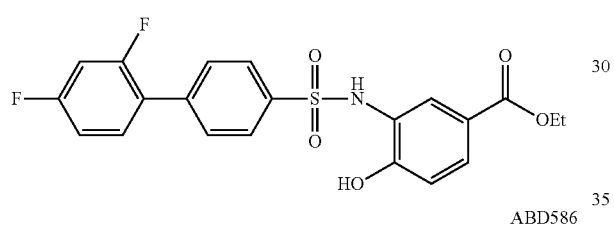

ABD586
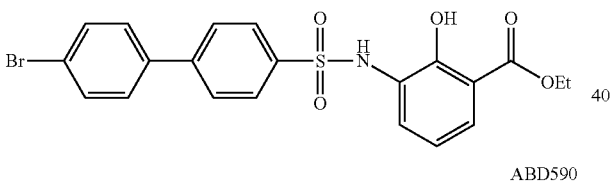

ABD590
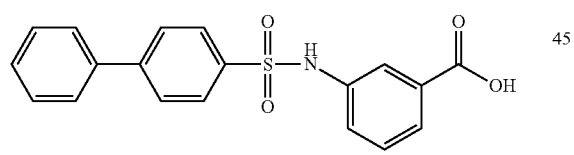

ABD612
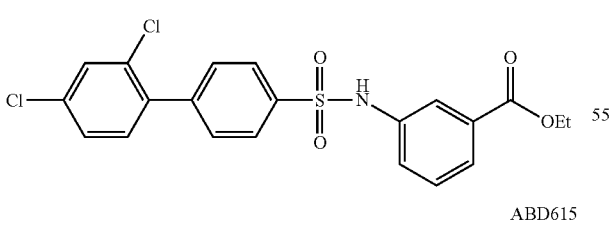

ABD615
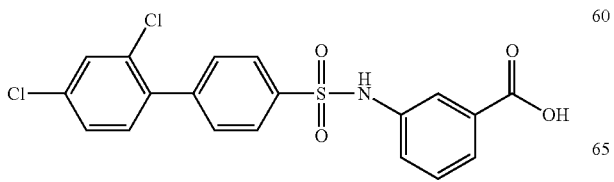

ABD617
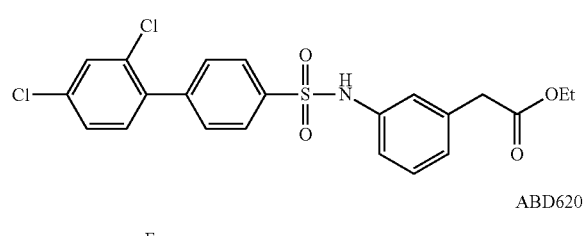

ABD620
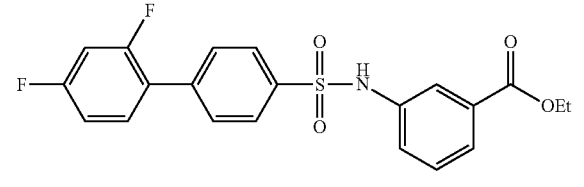

ABD623
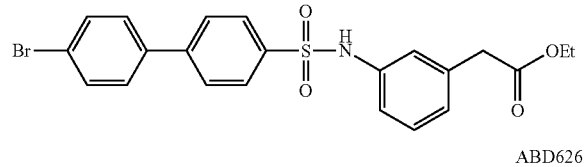

ABD626
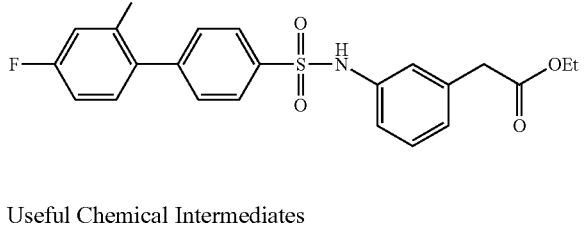

Useful Chemical Intermediates

Another aspect of the present invention pertains to the compounds described below, which are not encompassed by the above definitions, but which are chemical intermediates that are useful in the synthesis of the compounds described above.

Thus, another aspect of the present invention pertains to compounds selected from compounds of the following formulae and pharmaceutically acceptable salts, hydrates, and solvates thereof:

ABD447
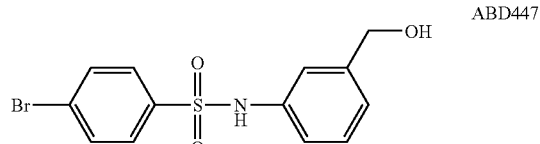

ABD460
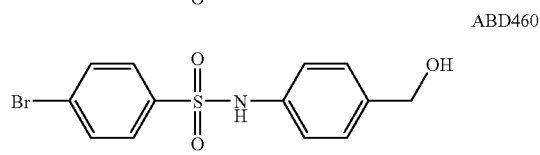

ABD461
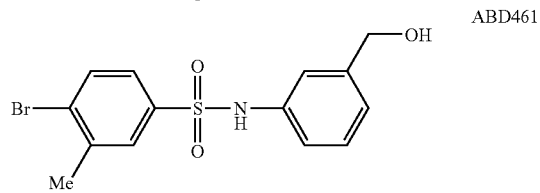

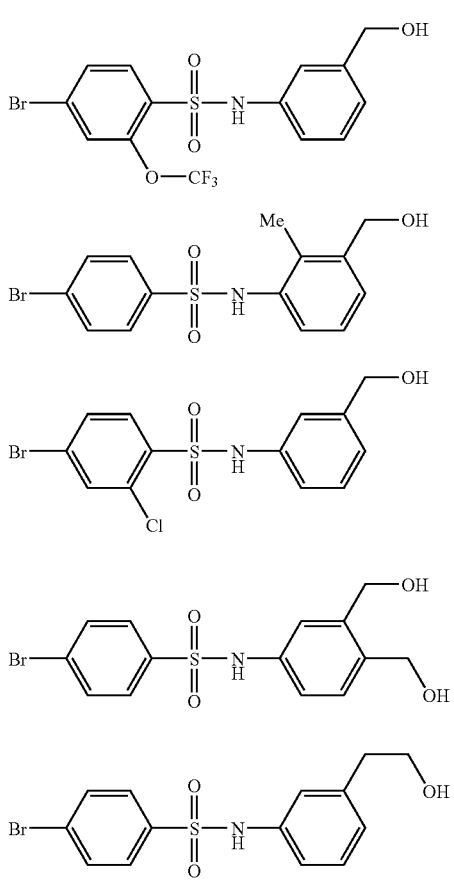

ABD516
ABD524
ABD538
ABD569
ABD624

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

Methods for the chemical synthesis of BPSAAA compounds of the present invention are described herein. These and/or other well-known methods may be modified and/or adapted in known ways in order to facilitate the synthesis of additional BPSAAA compounds of the present invention.

In one approach, an appropriate aromatic compound is sulfonylated using chlorosulfonic acid to give the corresponding sulfonic acid. The acid is then reacted with thionyl chloride to give the corresponding aryl sulfonyl chloride. Finally the sulfonyl chloride is coupled with an amine to give the corresponding sulfonamide.

An example of such a method is shown in the following scheme.

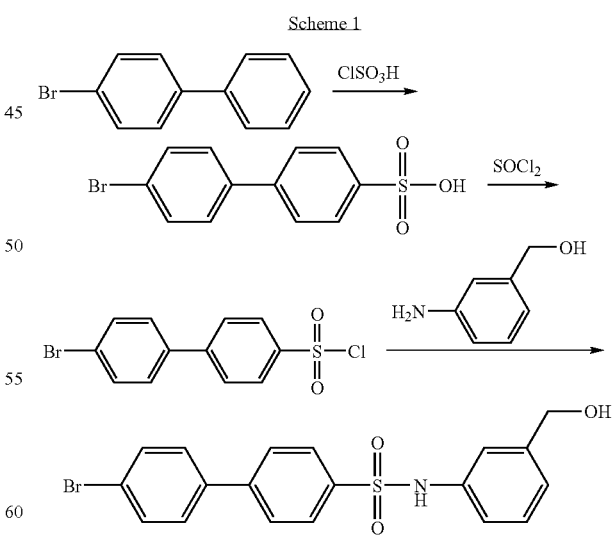

Scheme 1

In another approach, the biphenyl compound can be prepared following the formation of the sulfonamide by a Suzuki-type coupling using a suitable boronic acid and a suitable bromide, for example, as described by O'Brien et al., 2000.

An example of such a method is shown in the following scheme.

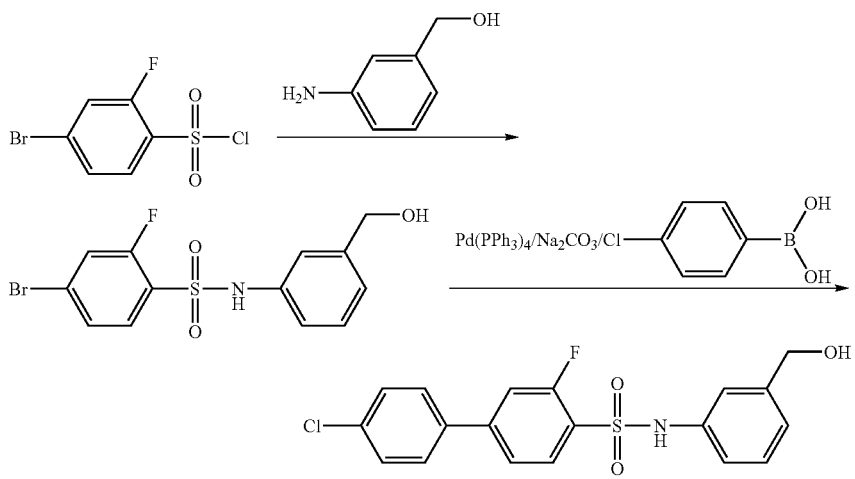

In another approach, the hydroxyalkyl-amino-phenyl group is prepared by catalytic hydrogenation of the corresponding nitro derivative, for example, with 10% palladium on carbon under an atmosphere of hydrogen gas in a solvent such as ethanol.

An example of such a method is shown in the following scheme.

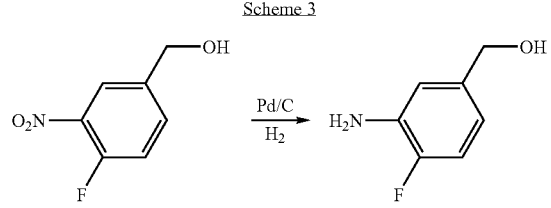 [SMILES: O=[N+]([O-])c1cc(CO)ccc1F ; "H2" ; Nc1cc(CO)ccc1F]

In another approach, the hydroxyalkyl-amino-phenyl group is prepared by reduction of the corresponding benzoic acid or benzoyl ester derivative, for example, with a reducing agent such as lithium aluminium hydride in a solvent such as tetrahydrofuran.

An example of such a method is shown in the following scheme.

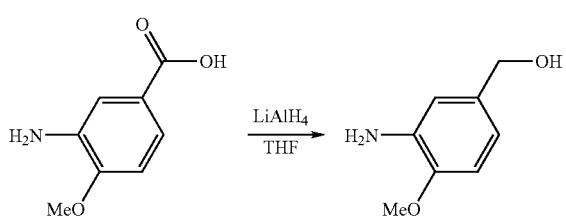

In another approach, the hydroxyalkyl-amino-phenyl group is prepared by both catalytic hydrogenation of the nitro group and reduction of a benzoic acid derivative, for example, with a catalyst such as 10% palladium on carbon under an atmosphere of hydrogen gas in a solvent such as ethanol followed by reduction with agent such as lithium aluminium hydride in a solvent such as tetrahydrofuran.

An example of such a method is shown in the following scheme.

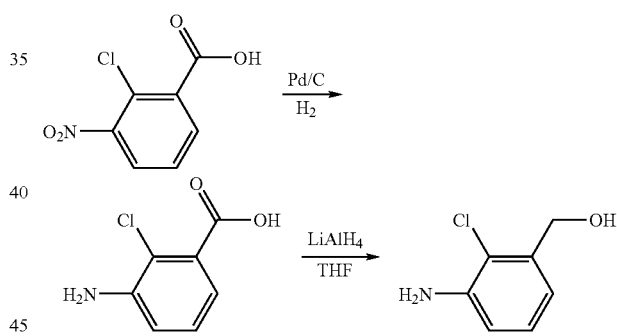

In another approach, the nitrogen atom of the sulfonamide may be further reacted, for example, with an alkylating agent.

An example of such a method is shown in the following scheme.

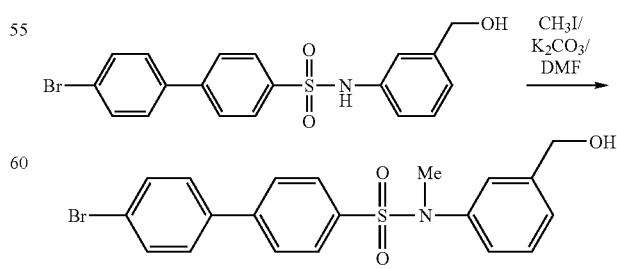

In another approach, the alcohol group can be further reacted, for example, with an acylating agent.

An example of such a method is shown in the following scheme.

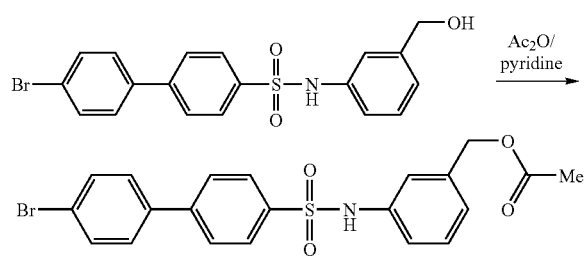

Scheme 7

The products may be purified, for example, by column chromatography, trituration with ether, or by crystallisation.

Uses

The BPSAAA compounds described herein are believed to be anti-inflammatory agents which may act by blockade or modification of pro-inflammatory signalling pathways (for example those mediated by TNFα signalling and NFκB or AP-1 activation) and thus may prevent inflammation or suppress autoimmune responses or offer protection against joint destruction and other effects of chronic inflammatory disease.

The BPSAAA compounds described herein are also believed to be anti-resorptive agents which may act by blockade or modification of pathways which lead to excessive osteoclast activity (for example those mediated by RANKL, TNFα, and IL-1 signalling and NFκB activation) and thereby protect against the bone loss seen in osteoporosis and many chronic inflammatory conditions.

Thus, the BPSAAA compounds described herein are believed to be useful in the treatment and/or prevention of inflammation and/or joint destruction and/or bone loss.

Thus, the BPSAAA compounds described herein are believed to be useful in the treatment and/or prevention of disorders mediated by excessive and/or inappropriate and/or prolonged activation of the immune system.

Thus, the BPSAAA compounds described herein are believed to be useful in the treatment and/or prevention of, inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

Thus, the BPSAAA compounds described herein are believed to be useful in the treatment and/or prevention of disorders associated with bone loss, such as bone loss associated with excessive osteoclast activation in rheumatoid arthritis, osteoporosis, cancer associated bone disease, Paget's disease and the like.

Use in Methods of Inhibition

One aspect of the invention pertains to a method of inhibiting an inflammatory response, in vitro or in vivo, comprising contacting an immune system component with an effective amount of a BPSAAA compound, as described herein.

One aspect of the invention pertains to a method of inhibiting cellular and/or molecular pathways leading to joint destruction, in vitro or in vivo, comprising contacting cells associated with an immune response with a therapeutically-effective amount of a BPSAAA compound, as described herein.

One aspect of the invention pertains to a method of inhibiting osteoclast survival, formation, and/or activity, in vitro or in vivo, comprising contacting an osteoclast with an effective amount of a BPSAAA compound, as described herein.

One aspect of the invention pertains to a method of inhibiting bone resorption, in vitro or in vivo, comprising contacting cells in the bone microenvironment with a therapeutically-effective amount of a BPSAAA compound, as described herein.

The term "immune system component," as used herein, relates to, but is not restricted to, cells such as macrophages, T-cells, B-cells, NK-cells, monocytes, neutrophils, dendritic cells, lymphocytes, leukocytes, granulocytes, antigen-presenting cells, and other cells of the haematopoietic lineage including osteoclasts.

The term "cells in the bone microenvironment," as used herein, pertains to cells such as osteoblasts, osteoclasts, osteocytes, and bone marrow stromal cells, which are located in close proximity to bone (e.g., within one hundred micrometers of the bone surface).

Use in Methods of Therapy

One aspect of the present invention pertains to a BPSAAA compound as described herein for use in a method of treatment of the human or animal body by therapy, for example, for use in a method of treatment and/or prevention.

Use in the Manufacture of Medicaments

One aspect of the present invention pertains to use of a BPSAAA compound, as described herein, in the manufacture of a medicament for use in treatment and/or prevention.

In one embodiment, the medicament comprises said BPSAAA compound.

Methods of Treatment

One aspect of the present invention pertains to a method of treatment and/or prevention comprising administering to a patient in need of treatment and/or prevention a therapeutically effective amount of a BPSAAA compound as described herein, preferably in the form of a pharmaceutical composition.

Diseases and Disorders

In one embodiment, the treatment and/or prevention is treatment and/or prevention of an inflammatory disorder or an autoimmune disorder.

In one embodiment, the treatment and/or prevention is treatment and/or prevention of a disorder associated with inflammation and/or activation of the immune system.

In one embodiment, the treatment and/or prevention is treatment and/or prevention of a disorder mediated by excessive and/or inappropriate and/or prolonged activation of the immune system.

In one embodiment, the treatment and/or prevention is treatment and/or prevention of inflammation.

In one embodiment, the treatment and/or prevention is treatment and/or prevention of a disorder associated with inflammation or activation of the immune system.

In one embodiment, the treatment and/or prevention is treatment and/or prevention of rheumatoid arthritis.

In one embodiment, the treatment and/or prevention is treatment and/or prevention of psoriasis.

In one embodiment, the treatment and/or prevention is treatment and/or prevention of psoriatic arthritis.

In one embodiment, the treatment and/or prevention is treatment and/or prevention of chronic obstructive pulmonary disease (COPD).

In one embodiment, the treatment and/or prevention is treatment and/or prevention of atherosclerosis.

In one embodiment, the treatment and/or prevention is treatment and/or prevention of ankylosing spondylitis.

In one embodiment, the treatment and/or prevention is treatment and/or prevention of inflammatory bowel disease.

In one embodiment, the treatment and/or prevention is prevention of an immune response leading to organ or graft rejection following transplant.

In one embodiment, the treatment and/or prevention is treatment of a tumour which over expresses TNFα, IL-1, or RANKL or in which inhibition of TNFα, IL-1, or RANKL facilitates or improves the action of cytotoxic tumouricidal agents.

In one embodiment, the treatment and/or prevention is treatment and/or prevention of a disease or disorder selected from: diseases having an inflammatory or autoimmune component, including asthma, allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes, multiple sclerosis, arthritis, systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumours, types of type 1 hypersensitivity reactions (anaphylaxis, skin allergy, hives, gout, allergic rhinitis, and allergic gastroenteritis); ulcerative colitis or Crohn's disease; or Muckle-Wells Syndrome.

In one embodiment, the treatment and/or prevention is treatment and/or prevention of a disorder mediated by osteoclasts.

In one embodiment, the treatment and/or prevention is treatment and/or prevention of a disorder characterised by excessive bone resorption.

In one embodiment, the treatment and/or prevention is treatment and/or prevention of bone loss.

In one embodiment, the treatment and/or prevention is treatment and/or prevention of bone loss associated with inflammation.

In one embodiment, the treatment and/or prevention is treatment and/or prevention of bone loss not associated with inflammation.

In one embodiment, the treatment and/or prevention is treatment and/or prevention of bone loss associated with excessive osteoclast activation.

In one embodiment, the treatment and/or prevention is treatment and/or prevention of joint destruction.

In one embodiment, the treatment and/or prevention is treatment and/or prevention of joint destruction associated with inflammation.

In one embodiment, the treatment and/or prevention is treatment and/or prevention of joint destruction associated with excessive osteoclast activation.

In one embodiment, the treatment and/or prevention is treatment and/or prevention of bone loss associated with rheumatoid arthritis, osteoporosis, cancer associated bone disease, or Paget's disease of bone.

In one embodiment, the treatment and/or prevention is treatment and/or prevention of rheumatoid arthritis, osteoporosis, cancer associated bone disease, or Paget's disease of bone.

In one embodiment, the treatment and/or prevention is treatment and/or prevention of neoplasia of bones, whether as a primary tumour or as metastases, including but not limited to, osteosarcoma and osteoma (Zheng et al., 1998, *J. Cell Biochem.*, Vol. 70, p. 121) and cancer associated bone disease (e.g., hypercalcaemia of malignancy, bone metastases, osteolytic bone metastases, multiple myeloma, breast carcinoma).

In one embodiment, the treatment and/or prevention is treatment and/or prevention of hypercalcaemia caused by conditions associated with increased bone resorption, including, but not limited to: vitamin D intoxication, primary or tertiary hyperparathyroidism, immobilisation, and sarcoidosis.

In one embodiment, the treatment and/or prevention is treatment and/or prevention of aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the treatment and/or prevention is treatment and/or prevention of osteopetrosis, osteoarthritis, or ectopic bone formation.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included. For example, use with perimenopausal women who may not yet have osteoporosis, but who are at risk of osteoporosis, is encompassed by the term "treatment."

The term "therapeutically-effective amount," as used herein, pertains to that amount of a BPSAAA compound, or a material, composition or dosage from comprising a BPSAAA compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously.

Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

BPSAAA compounds, as described herein, may also be used as cell culture additives to inhibit immune cell function, for example, to inhibit the survival, formation, and/or activity of macrophages, T-cells, or other cells involved in the immune response.

The BPSAAA compounds, as described herein, may also be used as cell culture additives, for example, to inhibit osteoclasts, for example, to inhibit the survival, formation, and/or activity of osteoclasts.

The BPSAAA compounds, as described herein, may also be used as part of an in vitro assay, for example, in order to determine whether a candidate host is likely to benefit from treatment with the compound in question.

The BPSAAA compounds, as described herein, may also be used as a standard, for example, in an assay, in order to identify other active compounds, other osteoclast inhibitors, etc.

Kits

One aspect of the invention pertains to a kit comprising (a) a BPSAAA compound as described herein, or a composition comprising a BPSAAA compound as described herein, e.g., preferably provided in a suitable container and/or with suitable packaging; and (b) instructions for use, e.g., written instructions on how to administer the BPSAAA compound or composition.

The written instructions may also include a list of indications for which the BPSAAA compound is a suitable treatment.

Routes of Administration

The BPSAAA compound or pharmaceutical composition comprising the BPSAAA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one embodiment, the route of administration is oral (e.g., by ingestion).

The Subject/Patient

The subject/patient may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject/patient may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the BPSAAA compound to be administered alone, it is preferable to present it as a pharmaceutical formulation (e.g., composition, preparation, medicament) comprising at least one BPSAAA compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one BPSAAA compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the BPSAAA compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

The formulations may be prepared by any methods well known in the art of pharmacy. Such methods include the step of bringing into association the BPSAAA compound with a carrier which constitutes one or more accessory ingredients. In general, the formulations are prepared by uniformly and intimately bringing into association the BPSAAA compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more BPSAAA compounds and optionally one or more other pharmaceutically acceptable ingredients, including, for example, penetration, permeation, and absorption enhancers. Formulations may also suitably be provided in the form of a depot or reservoir.

The BPSAAA compound may be dissolved in, suspended in, or admixed with one or more other pharmaceutically acceptable ingredients. The BPSAAA compound may be presented in a liposome or other microparticulate which is designed to target the BPSAAA compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the BPSAAA compound in a flavored basis, usually sucrose and acacia or tragacanth. Pastilles typically comprise the BPSAAA compound in an inert matrix, such as gelatin and glycerin, or sucrose and acacia. Mouthwashes typically comprise the BPSAAA compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotion, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the BPSAAA compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the BPSAAA compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the BPSAAA compound and a paraffinic or a water-miscible ointment base.

Creams are typically prepared from the BPSAAA compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the BPSAAA compound through the skin or other affected areas. Examples of such dermal penetration enhancers include dimethylsulfoxide and related analogues.

Emulsions are typically prepared from the BPSAAA compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the BPSAAA compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the BPSAAA compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the BPSAAA compound is dissolved or suspended in a suitable carrier, especially an aqueous solvent for the BPSAAA compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the BPSAAA compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the BPSAAA compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the BPSAAA compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the BPSAAA compounds, and compositions comprising the BPSAAA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the BPSAAA compound is in the range of about 100 μg to about 250 mg (more typically about 100 μg to about 25 mg) per kilogram body weight of the subject per day. Where the BPSAAA compound is a salt, a hydrate, or a solvate, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Synthesis 1

4'-Bromo-biphenyl-4-sulfonic acid (4-hydroxymethyl-phenyl)-amide (ABD445)

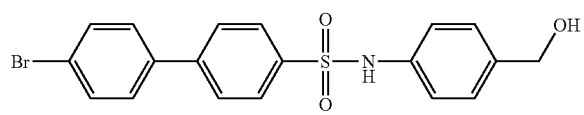

Method A:

4'-Bromo-biphenyl sulfonyl chloride (0.4 g) and (4-aminophenyl)-methanol (1 g) were dissolved in dichloromethane containing pyridine (1 mL). The mixture was stirred for 2 hours at room temperature and diluted with dichloromethane (100 mL). After washing with 1M HCl (100 mL) and water (100 mL), the solvent was evaporated and the title compound was obtained as a white solid following recrystallisation from ethyl acetate/petroleum spirit. $^{13}$C NMR (DMSO-$d_6$): δ 62.4, 117.9, 122.3, 127.2, 127.4, 128.8, 129.3, 131.9, 137.5, 137.6, 138.8, 143.0 and 143.9.

Synthesis 2

4'-Bromo-biphenyl-4-sulfonic acid (3-hydroxymethyl-phenyl)-amide (ABD446)

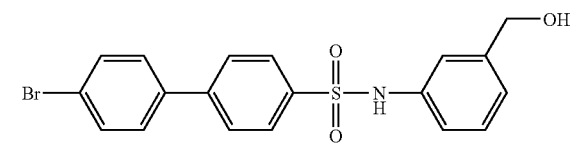

Using a method analogous to Method A, with 4'-bromo-biphenyl sulfonyl chloride and (3-amino-phenyl)-methanol, the title compound was obtained as a white powder. $^{13}$C NMR (DMSO-d$_6$): δ 62.4, 120.1, 122.3, 127.2, 127.4, 129.3, 131.9, 136.1, 137.5, 138.5, 138.7 and 142.9.

Synthesis 3

4'-Bromo-biphenyl-4-sulfonic acid [4-(2-hydroxy-ethyl)-phenyl]-amide (ABD451)

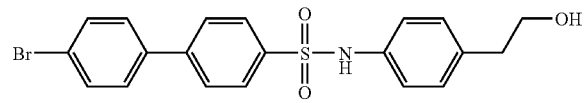

Using a method analogous to Method A, with 4'-bromo-biphenyl sulfonyl chloride and 2-(4-amino-phenyl)-ethanol, the title compound was obtained as a white powder. $^{13}$C NMR (DMSO-d$_6$): δ 38.3, 61.2, 120.1, 122.2, 127.2, 127.4, 129.0, 129.7, 132.0, 135.4, 135.5, 137.5, 138.9 and 142.9.

Synthesis 4

4'-Bromo-biphenyl-4-sulfonic acid (5-hydroxymethyl-2-methyl-phenyl)-amide (ABD499)

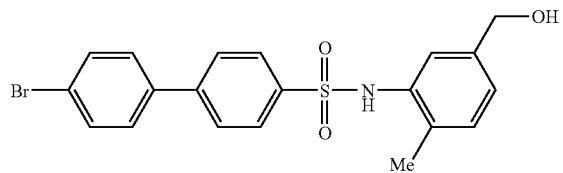 [SMILES: Cc1ccc(CO)cc1NS(=O)(=O)c1ccc(-c2ccc(Br)cc2)cc1]

Using a method analogous to Method A, with 4'-bromo-biphenyl sulfonyl chloride and (3-amino-4-methyl-phenyl)-methanol, the title compound was obtained as a white powder. $^{13}$C NMR (DMSO-d$_6$): δ 17.4, 62.3, 122.2, 124.5, 124.9, 127.3, 127.4, 129.1, 130.5, 132.0, 132.2, 134.5, 137.5, 139.8, 140.9 and 142.7. $^1$H NMR (CDCl$_3$): δ 1.97 (3H, s), 4.38 (2H, d, J=4.9 Hz), 7.05 (3H, m), 7.67 (4H, m), 7.74 (2H, d, J=8.2 Hz), 7.85 (2H, d, J=8.2 Hz) and 9.65 (1H, s).

Synthesis 5

4'-Bromo-biphenyl-4-sulfonic acid (3-hydroxymethyl-2-methyl-phenyl)-amide (ABD500)

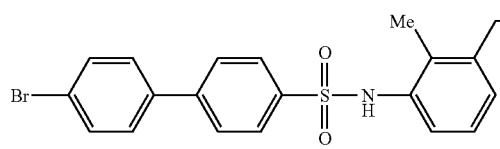

Using a method analogous to Method A, with 4'-bromo-biphenyl sulfonyl chloride and (3-amino-2-methyl-phenyl)-methanol, the title compound was obtained as a white powder. $^{13}$C NMR (DMSO-d$_6$): δ 12.8, 61.3, 122.2, 125.3, 125.4, 127.2, 127.3, 129.1, 131.9, 132.6, 134.5, 137.5, 139.7, 141.7 and 142.7. $^1$H NMR (DMSO-d$_6$): δ 1.99 (3H, s), 4.40 (2H, d, J=4.9 Hz), 5.12 (1H, t, J=5.4 Hz), 6.81 (1H, d, J=7.6 Hz), 7.06 (1H, t, J=7.6 Hz), 7.23 (1H, s), 7.69 (6H, m), 7.86 (2H, d, J=8.2 Hz) and 9.66 (1H, s).

Synthesis 6

2'-Nitro-biphenyl-4-sulfonic acid (3-hydroxymethyl-phenyl)-amide (ABD514)

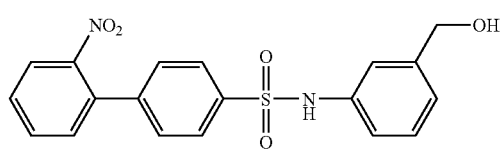

Using a method analogous to Method A, with 2'-nitro-biphenyl sulfonyl chloride and (3-amino-phenyl)-methanol, the title compound was obtained as a clear oil.

Synthesis 7

4'-Bromo-2'-fluoro-biphenyl-4-sulfonic acid (3-hydroxymethyl-phenyl)-amide (ABD515)

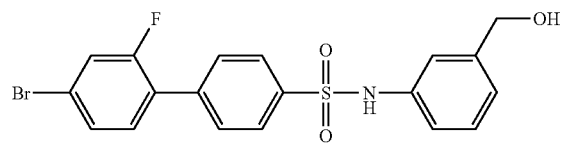

Using a method analogous to Method A, with 4'-bromo-2'-fluoro-biphenyl sulfonyl chloride and (3-amino-phenyl)-methanol, the title compound was obtained as a white powder. $^{13}$C NMR (DMSO-d$_6$): δ 62.5, 117.8, 118.0, 119.6, 122.2 (d, J=9.8 Hz), 126.0 (d, J=12.7 Hz), 127.2, 127.9, 128.3, 129.3, 129.9, 132.2, 137.5, 138.3, 139.3, 143.9 and 158.9 (d, J=252.0 Hz). $^1$H NMR (DMSO-d$_6$): δ 4.41 (2H, s), 5.21 (1H, s), 6.96 (1H, d, J=8.5 Hz), 7.04 (1H, d, J=8.5 Hz), 7.18 (2H, m), 7.51 (2H, m), 7.64 (1H, s), 7.71 (2H, d, J=8.8 Hz), 7.89 (2H, d, J=8.2 Hz) and 10.43 (1H, s).

Synthesis 8

4'-Bromo-biphenyl-4-sulfonic acid (4-chloro-3-hydroxymethyl-phenyl)-amide (ABD520)

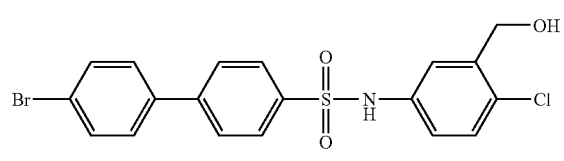 [SMILES: O=S(=O)(Nc1ccc(Cl)c(CO)c1)c1ccc(-c2ccc(Br)cc2)cc1]

Using a method analogous to Method A, with 4'-bromo-biphenyl sulfonyl chloride and (5-amino-2-chloro-phenyl)-methanol, the title compound was obtained as a white powder. $^{13}$C NMR (DMSO-d$_6$): δ 60.0, 118.9, 119.2, 122.3, 127.4, 127.6, 129.2, 129.6, 132.0, 132.2, 136.8, 137.4, 138.5, 140.7 and 143.1. $^1$H NMR (DMSO-d$_6$): δ 4.44 (2H, d, J=5.2 Hz), 5.47 (1H, m), 7.04 (1H, d, J=8.8 Hz), 7.26 (1H, d, J=8.2 Hz), 7.39 (1H, s), 7.65 (4H, m), 8.84 (4H, m) and 10.54 (1H, s).

Synthesis 9

(3-Amino-4-methoxy-phenyl)-methanol (ABD526)

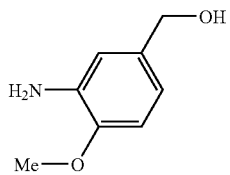 [SMILES: COc1ccc(CO)cc1N]

Method B:

3-Amino-4-methoxy-benzoic acid (5 g) was dissolved in THF (100 mL) and added dropwise to a suspension of LiAlH$_4$ (5 g) in THF (200 mL). The mixture was stirred at room temperature for 2 hours followed by 50° C. for 2 hours. Further THF (100 mL) and water (100 mL) were added and the mixture was allowed to settle and the liquid decanted from the top level, leaving behind a thick residue. The liquid was evaporated until all the THF was removed and residue was extracted with ethyl acetate, washed repeatedly, dried (Na$_2$SO$_4$), and evaporated to give a white powder which was recrystallised from ethyl acetate/petrol to give the title compound. $^{13}$C NMR (CDCl$_3$): δ 55.3, 63.0, 110.2, 112.9, 115.0, 134.5, 136.9 and 145.5.

Synthesis 10

(3-Amino-2-chlorophenyl)methanol (ABD519)

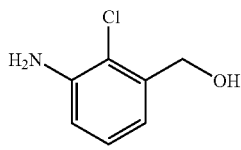

Using a method analogous to Method B, with 3-amino-4-chlorobenzoic acid, the title compound was obtained as a white powder.

Synthesis 11

4'-Bromo-biphenyl-4-sulfonic acid (3-hydroxymethyl-2-chloro-phenyl)-amide (ABD528)

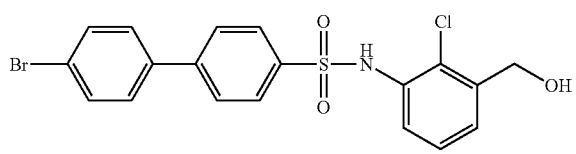 [SMILES: O=S(=O)(Nc1cccc(CO)c1Cl)c1ccc(-c2ccc(Br)cc2)cc1]

Using a method analogous to Method A, with 4'-bromo-biphenyl sulfonyl chloride and (3-amino-2-chlorophenyl)methanol (ABD519), the title compound was obtained as a white powder. $^{13}$C NMR (DMSO-d$_6$): δ 60.5, 122.3, 125.0, 125.4, 126.8, 127.1, 127.3, 127.5, 129.3, 132.1, 133.4, 137.5, 139.7, 141.1 and 142.9. $^1$H NMR (DMSO-d$_6$): δ 4.45 (2H, s), 7.15 (1H, d, J=8.2 Hz), 7.26 (1H, t, J=8.2 Hz), 7.35 (1H, t, J=8.2 Hz), 7.65-7.85 (8H, m) and 10.96 (1H, s).

Synthesis 12

4'-Bromo-biphenyl-4-sulfonic acid (5-hydroxymethyl-2-methoxy-phenyl)-amide (ABD529)

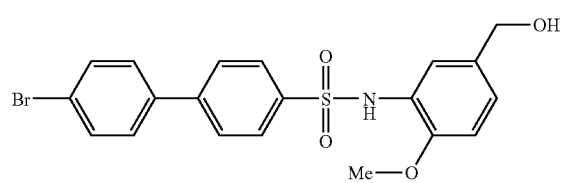 [SMILES: COc1ccc(CO)cc1NS(=O)(=O)c1ccc(-c2ccc(Br)cc2)cc1]

Using a method analogous to Method A, with 4'-bromo-biphenyl sulfonyl chloride and (3-amino-4-methoxy-phenyl)-methanol (ABD526), the title compound was obtained as a white powder. $^{13}$C NMR (DMSO-d$_6$): δ 55.4, 62.3, 122.1, 126.8, 127.3, 127.4, 129.0, 132.0, 124.8, 131.9, 132.2, 134.7, 137.7, 139.7, 142.7 and 151.3.

Synthesis 13

(3-Amino-4-chlorophenyl)methanol (ABD532)

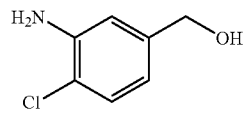

Using a method analogous to Method B, with 3-amino-4-chlorobenzoic acid, the title compound was obtained as a white powder.

Synthesis 14

4'-Bromo-biphenyl-4-sulfonic acid (5-hydroxymethyl-2-chloro-phenyl)-amide (ABD530)

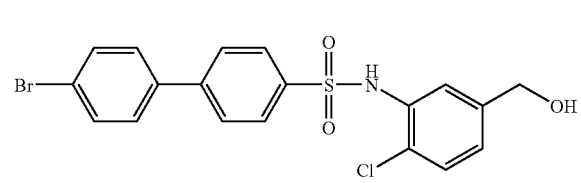 [SMILES: O=S(=O)(Nc1cc(CO)ccc1Cl)c1ccc(-c2ccc(Br)cc2)cc1]

Using a method analogous to Method A, with 4'-bromo-biphenyl sulfonyl chloride and (3-chloro-4-methoxy-phenyl)-methanol (ABD532), the title compound was obtained as a white powder. $^{13}$C NMR (DMSO-d$_6$): δ 61.8, 122.2, 125.3, 127.0, 127.2, 127.8, 128.9, 129.2, 129.6, 132.0, 133.2, 137.5, 139.6, 142.6 and 142.9.

Synthesis 15

4-Bromo-N-(3-hydroxymethyl-phenyl)-benzenesulfonamide (ABD447)

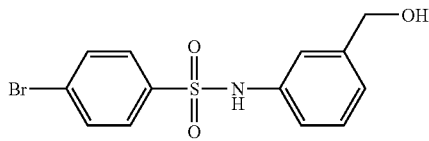 [SMILES: O=S(=O)(Nc1cccc(CO)c1)c1ccc(Br)cc1]

Using a method analogous to Method A, with 4-bromophenyl sulfonyl chloride and (3-amino-phenyl)-methanol, the title compound was obtained as a white powder. $^{13}$C NMR (DMSO-d$_6$): δ 62.4, 118.1, 118.4, 122.4, 126.8, 128.5, 128.8, 132.2, 137.2, 138.7 and 143.8.

Synthesis 16

4-Bromo-N-(4-hydroxymethyl-phenyl)-benzenesulfonamide (ABD460)

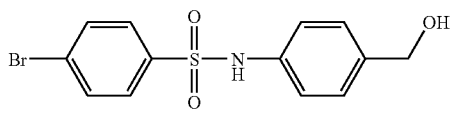

Using a method analogous to Method A, with 4-bromophenyl sulfonyl chloride and (4-amino-phenyl)-methanol, the title compound was obtained as a white powder.

Synthesis 17

4-Bromo-N-(3-hydroxymethyl-phenyl)-3-methyl-benzenesulfonamide (ABD461)

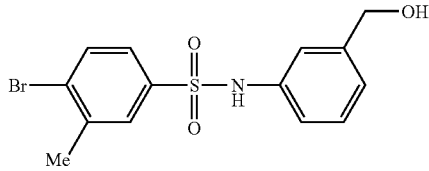 [SMILES: Cc1cc(S(=O)(=O)Nc2cccc(CO)c2)ccc1Br]

Using a method analogous to Method A, with 4'-bromo-3-methyl-phenyl sulfonyl chloride and (3-amino-phenyl)-methanol, the title compound was obtained as a white powder. $^{13}$C NMR (CDCl$_3$): δ 23.0, 64.5, 119.7, 120.1, 123.8, 125.9, 129.1, 130.5, 133.1, 136.6, 138.1, 139.5 and 142.5. $^1$H NMR (CDCl$_3$): δ 2.31 (3H, s), 4.56 (2H, s), 6.98 (1H, d, J=8.2 Hz), 7.07 (1H, d, J=7.0 Hz), 7.15 (1H, d, J=7.6 Hz), 7.18 (1H, d, J=7.6 Hz), 7.37 (1H, d, J=8.5 Hz) and 7.61 (1H, d, J=8.2 Hz).

Synthesis 18

4-Bromo-N-(3-hydroxymethyl-phenyl)-2-trifluoromethoxy-benzenesulfonamide (ABD516)

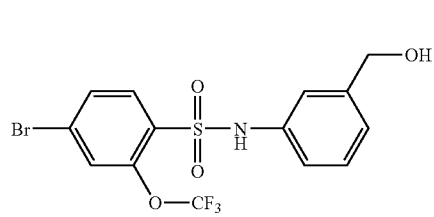 [SMILES: O=S(=O)(Nc1cccc(CO)c1)c1ccc(Br)cc1OC(F)(F)F]

Using a method analogous to Method A, with 4-bromo-2-trifluoromethoxy-phenyl sulfonyl chloride and (3-amino-phenyl)-methanol, the title compound was obtained as a white powder.

Synthesis 19

4-Bromo-N-(3-hydroxymethyl-2-methyl-phenyl)benzenesulfonamide (ABD524)

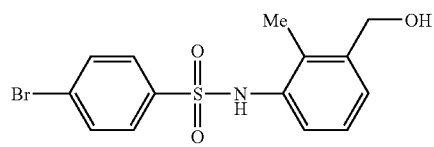 [SMILES: Cc1c(CO)cccc1NS(=O)(=O)c1ccc(Br)cc1]

Using a method analogous to Method A, with 4-bromophenyl sulfonyl chloride and (3-amino-2-methyl-phenyl)-methanol, the title compound was obtained as a white powder.

Synthesis 20

4-Bromo, 2-chloro-N-(3-hydroxymethyl-phenyl)benzenesulfonamide (ABD538)

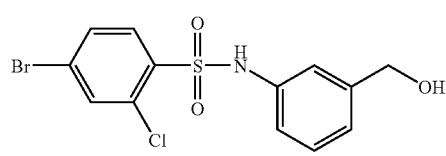 [SMILES: O=S(=O)(Nc1cccc(CO)c1)c1ccc(Br)cc1Cl]

Using a method analogous to Method A, with 4-bromo-2-chloro-phenyl sulfonyl chloride and (3-amino-phenyl)-methanol, the title compound was obtained as a white powder.

Synthesis 21

2',4'-Dichloro-biphenyl-4-sulfonic acid (3-hydroxymethyl-phenyl)-amide (ABD455)

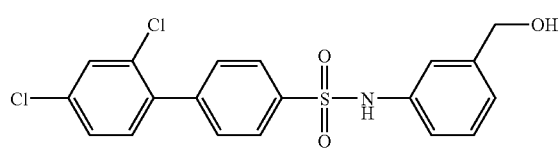

Method C:

4-Bromo-N-(3-hydroxymethyl-phenyl)-benzenesulfonamide (ABD447) (1 g) was dissolved in a mixture of toluene (15 mL) and ethanol (15 mL). 2,4-Dichloro-phenyl boronic acid (1 g) was added followed by 2 M $Na_2CO_3$ (15 mL). The mixture was stirred vigorously under $N_2$ and $(PPh_3)_4Pd$ (0.15 g) was added. The mixture was refluxed with stirring for 3 hours under an atmosphere of $N_2$. The solvent was removed under vacuum, the residue was dissolved in ethyl acetate and washed with water and saturated NaCl solution. After drying ($Na_2SO_4$), the solvent was evaporated and the resultant oil purified by column chromatography and recrystallised from ethyl acetate and petroleum spirit to give the title compound. $^{13}C$ NMR (DMSO-$d_6$): δ 64.7, 120.0, 120.6, 123.9, 127.1, 127.5, 129.6, 130.0, 130.1, 131.9, 133.0, 134.9, 136.6, 137.1, 138.5, 142.5 and 143.0. $^1H$ NMR (DMSO-$d_6$): δ 4.39 (2H, s), 5.20 (1H, s), 6.96 (1H, d, J=7.6 Hz), 7.03 (1H, d, J=8.2 Hz), 7.14 (1H, s), 7.20 (1H, d, J=8.2 Hz), 7.44 (1H, d, J=8.8 Hz), 7.50 (1H, d, J=8.8 Hz), 7.60 (2H, d, J=7.9 Hz), 7.75 (1H, s), 7.86 (2H, d, J=7.9 Hz) and 10.40 (1H, s).

Synthesis 22

2',4'-Difluoro-biphenyl-4-sulfonic acid (3-hydroxymethyl-phenyl)-amide (ABD456)

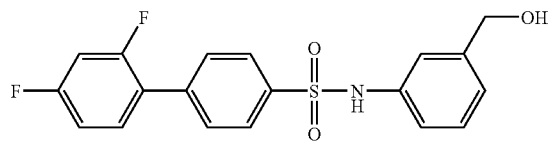

Using a method analogous to Method C, with 4-bromo-N-(3-hydroxymethyl-phenyl)-benzenesulfonamide (ABD447) and 2,4-difluoro-phenyl boronic acid, the title compound was obtained as a crystalline white solid. $^{13}C$ NMR (CDCl$_3$): δ 64.7, 104.6 (t, J=25.4 Hz), 112.0 (d, J=19.5 Hz), 119.9, 120.4, 123.7 (m), 123.8, 127.5, 129.5, 129.6, 131.5 (dd, J=25.2, 3.9 Hz), 136.7, 138.2, 139.8, 142.5, 159.7 (dd, J=249.0, 11.7 Hz) and 162.9 (dd, J=249.0, 11.7 Hz). $^1H$ NMR (CDCl$_3$): δ 4.60 (2H, s), 6.94 (2H, m), 7.09 (2H, m), 7.20 (1H, d, J=7.3 Hz), 7.27 (1H, m), 7.34 (1H, d, J=7.0 Hz), 7.53 (2H, d, J=8.2 Hz) and 7.83 (2H, d, J=7.6 Hz).

Synthesis 23

2',4'-Difluoro-2-methyl-biphenyl-4-sulfonic acid (3-hydroxymethyl-phenyl)-amide (ABD465)

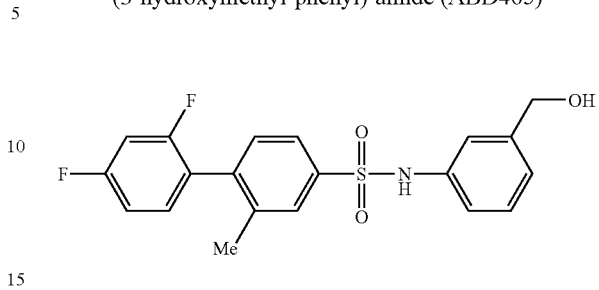

Using a method analogous to Method C, with 4-bromo-N-(3-hydroxymethyl-phenyl)-3-methyl-benzenesulfonamide (ABD461) and 2,4-difluoro-phenyl boronic acid, the title compound was obtained as a clear oil. $^{13}C$ NMR (CDCl$_3$): δ 23.0, 64.6, 104.2 (t, J=26.5 Hz), 111.6 (dd, J=21.5, 2.9 Hz), 119.8, 120.1, 123.6, 123.8, 124.4, 128.6, 129.5, 130.9, 131.8 (m), 136.6, 138.4, 138.6, 139.8, 142.4, 159.4 (dd, J=250.0, 12.7 Hz) and 162.9 (1H, dd, J=250.0, 12.7 Hz). $^1H$ NMR (CDCl$_3$): δ 2.11 (3H, s), 4.56 (2H, s), 6.90 (2H, m), 7.09 (2H, m), 7.18 (2H, m), 7.31 (1H, dd, J=25.0, 8.5 Hz), 7.61 (1H, d, J=7.3 Hz) and 7.70 (2H, m).

Synthesis 24

2',4'-Difluoro-biphenyl-4-sulfonic acid (4-hydroxymethyl-phenyl)-amide (ABD466)

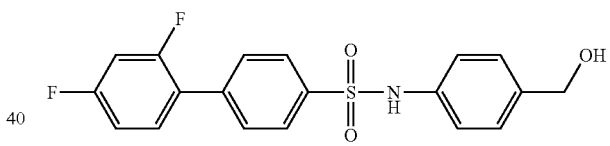

Using a method analogous to Method C, with 4-bromo-N-(4-hydroxymethyl-phenyl)-benzenesulfonamide (ABD460) and 2,4-difluoro-phenyl boronic acid, the title compound was obtained as a crystalline white solid. $^1H$ NMR (CDCl$_3$): δ 4.63 (2H, s), 6.52 (1H, s), 7.08 (2H, d, J=7.3 Hz), 7.26 (1H, m), 7.43 (2H, d, J=7.6 Hz), 7.56 (1H, d, J=7.3 Hz), 7.63 (2H, d, J=7.6 Hz) and 7.81 (2H, d, J=7.3 Hz).

Synthesis 25

4'-Chloro-biphenyl-4-sulfonic acid (3-hydroxymethyl-phenyl)-amide (ABD510)

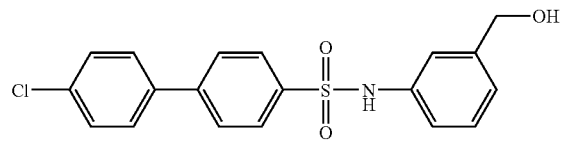

Using a method analogous to Method C, with 4-bromo-N-(3-hydroxymethyl-phenyl)-benzenesulfonamide (ABD447)

Synthesis 26

4'-Trifluoromethyl-biphenyl-4-sulfonic acid (3-hydroxymethyl-phenyl)-amide (ABD512)

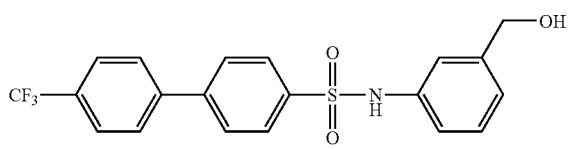 [SMILES: O=S(=O)(Nc1cccc(CO)c1)c1ccc(-c2ccc(C(F)(F)F)cc2)cc1]

Using a method analogous to Method C, with 4-bromo-N-(3-hydroxymethyl-phenyl)-benzenesulfonamide (ABD447) and 4-trifluoromethyl-phenyl boronic acid, the title compound was obtained as a crystalline white solid. $^{13}$C NMR (DMSO-d$_6$): δ 62.5, 117.8, 118.0, 122.0, 125.8, 127.4, 127.6, 128.0, 128.6, 129.1, 137.6, 139.4, 142.3, 142.7 and 143.9. $^1$H NMR (DMSO-d$_6$): δ 4.39 (2H, d, J=4.6 Hz), 5.22 (1H, m), 6.96 (1H, d, J=7.6 Hz), 7.02 (1H, d, J=7.6 Hz), 7.16 (2H, m), 7.83 (2H, d, J=8.5 Hz), 7.89 (6H, m), 10.42 (1H, br s).

Synthesis 27

4'-Fluoro-3-trifluoromethoxy-biphenyl-4-sulfonic acid (3-hydroxymethyl-phenyl)-amide (ABD523)

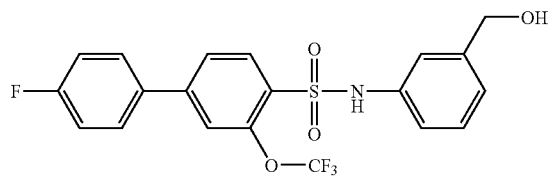

Using a method analogous to Method C, with 4-bromo-N-(3-hydroxymethyl-phenyl)-2-trifluoromethoxy-benzenesulfonamide (ABD516) and 4-fluoro-phenyl boronic acid, the title compound was obtained as a crystalline white solid. $^{13}$C NMR (DMSO-d$_6$): δ 62.6, 115.9, 117.7, 119.3, 122.1, 125.5, 128.9, 129.5, 129.9, 130.6, 131.5, 133.4, 137.1, 143.9, 145.6, 145.7 and 162.9 (1H, d, J=247.1 Hz). $^1$H NMR (DMSO-d$_6$): δ 4.39 (2H, d, J=5.2 Hz), 5.22 (1H, t, J=6.1 Hz), 6.98 (2H, t, J=7.6 Hz), 7.12 (2H, m), 7.33 (2H, d, J=8.2 Hz), 7.71 (1H, s), 7.80 (2H, m), 8.02 (2H, d, J=8.2 Hz) and 10.64 (1H, br s).

Synthesis 28

4'-Fluoro-biphenyl-4-sulfonic acid (3-hydroxymethyl-phenyl)-amide (ABD525)

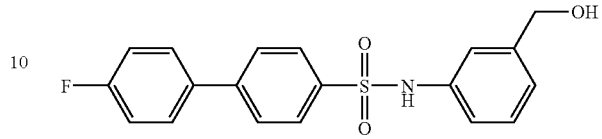

Using a method analogous to Method C, with 4-bromo-N-(3-hydroxymethyl-phenyl)-benzenesulfonamide (ABD447) and 4-fluoro-phenyl boronic acid, the title compound was obtained as a crystalline white solid. $^1$H NMR (DMSO-d$_6$): δ 4.39 (2H, d, J=5.2 Hz), 5.22 (1H, t, J=5.8 Hz), 6.95 (1H, d, J=7.6 Hz), 7.01 (1H, d, J=8.5 Hz), 7.16 (2H, d, J=8.2 Hz), 7.31 (2H, t, J=8.5 Hz), 7.75 (2H, d, J=8.2 Hz), 7.83 (4H, m) and 10.38 (1H, br s).

Synthesis 29

2',4'-Difluoro-biphenyl-4-sulfonic acid (3-hydroxymethyl-2-methyl-phenyl)-amide (ABD527)

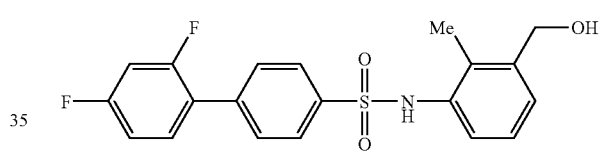

Using a method analogous to Method C, with 4-bromo-N-(3-hydroxymethyl-2-methyl-phenyl)-benzenesulfonamide (ABD524) and 2,4-difluoro-phenyl boronic acid, the title compound was obtained as a crystalline white solid. $^{13}$C NMR (DMSO-d$_6$): δ 12.7, 61.3, 104.5 (t, J=25.4 Hz), 112.4 (d, J=19.5 Hz), 121.7, 125.3, 125.5, 127.0, 129.4, 129.7, 131.5 (dd, J=25.2, 3.9 Hz), 132.5, 134.4, 138.3, 139.9 141.7, 159.7 (dd, J=249.0, 11.7 Hz) and 162.9 (dd, J=249.0, 11.7 Hz). $^1$H NMR (DMSO-d$_6$): δ 1.96 (3H, s), 4.38 (2H, s), 5.16 (1H, s), 6.81 (1H, d, J=7.9 Hz), 7.05 (1H, t, J=7.6 Hz), 7.22 (2H, m), 7.42 (1H, t, J=7.9 Hz), 7.71 (5H, m) and 9.65 (1H, s).

Synthesis 30

4'-Difluoro, 3-chlorobiphenyl-4-sulfonic acid-(3-hydroxymethyl-phenyl)-amide (ABD551)

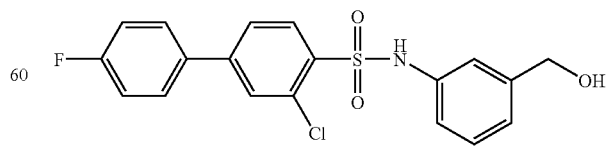

Using a method analogous to Method C, with 4-bromo, 2-chloro-N-(3-hydroxymethyl-phenyl)-benzenesulfonamide (ABD538) and 4-fluoro-phenyl boronic acid, the title compound was obtained as a crystalline white solid. $^1$H NMR (DMSO-$d_6$): δ 4.39 (2H, d, J=5.2 Hz), 5.21 (1H, t, J=5.2 Hz), 6.94 (1H, d, J=7.6 Hz), 7.01 (1H, d, J=8.2 Hz), 7.15 (2H, m), 7.31 (2H, t, J=8.8 Hz), 7.79 (3H, m), 7.91 (1H, s), 8.09 (1H, d, J=8.2 Hz) and 10.67 (1H, s).

Synthesis 31

4'-Dimethylaminobiphenyl-4-sulfonic acid-(3-hydroxymethyl-phenyl)-amide (ABD559)

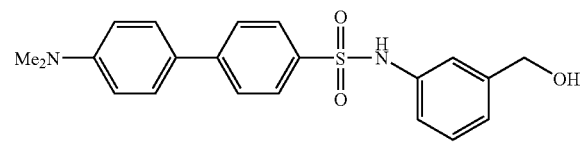 [SMILES: CN(C)c1ccc(-c2ccc(S(=O)(=O)Nc3cccc(CO)c3)cc2)cc1]

Using a method analogous to Method C, with 4-bromo-N-(3-hydroxymethyl-phenyl)-benzenesulfonamide (ABD447) and 4-dimethylamino-phenyl boronic acid, the title compound was obtained as a crystalline white solid. $^1$H NMR (DMSO-$d_6$): δ 2.93 (6H, s), 4.39 (2H, s), 5.20 (1H, s), 6.77 (2H, d, J=8.5 Hz), 6.95 (1H, d, J=7.6 Hz), 7.01 (1H, d, J=8.8 Hz), 7.14 (1H, s), 7.17 (1H, t, J=7.6 Hz), 7.57 (2H, d, J=8.5 Hz), 7.76 (4H, m) and 10.26 (1H, s).

Synthesis 32

4-Chloro-2-fluorophenylboronic acid

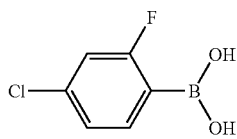 [SMILES: OB(O)c1ccc(Cl)cc1F]

1-Bromo, 4-chloro, 2-fluorobenzene (5 g) was dissolved in anhydrous THF (50 ml). Excess Mg turnings (freshly oven dried) were added and the mixture gently heated under an atmosphere of nitrogen, until a self-sustaining reaction commenced. The reaction remained at reflux for a further 10 mins, and was then gently boiled with external heating for a further 10 min. The mixture was allowed to cool to room temp, giving a Grignard of about 0.5 M solution.

The solution was transferred to a separate vessel, a further 20 ml THF added and placed under an atmosphere of nitrogen. The solution was cooled in an ethanol/CO$_2$ bath to below −40° C. and triisopropyl borate (14 ml) added via a syringe. The mixture was allowed to slowly warm to 0° C. and then stirred in an ice bath for a further hour. The reaction was quenched with sat. NH$_4$Cl, extracted with ether and the organic washed with 10% HCl and dried (Na$_2$SO$_4$). Evaporation gave a waxy yellow solid. Purification by column chromatography gave the title compound as a waxy solid. The solid was dissolved in ether and recrystallised with addition of petrol and slow evaporation of the ether. Further recrystallisation by this method gave the pure product as a fluffy white powder.

Synthesis 33

4'-Chloro, 2'-fluoro-biphenyl-4-sulfonic acid (3-hydroxymethyl-phenyl)-amide (ABD575)

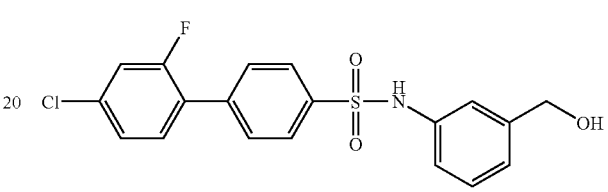

Using a method analogous to Method C, with 4-bromo-N-(3-hydroxymethyl-phenyl)-benzenesulfonamide (ABD447) and 4-chloro, 2-fluoro-phenyl boronic acid, the title compound was obtained as a crystalline white solid. $^{13}$C NMR (DMSO-$d_6$): δ 62.5, 116.9, 117.7, 118.0, 122.1, 125.3, 125.7 (d, J=12.7 Hz), 127.0, 128.8, 129.6, 132.1, 134.1 (d, J=10.8 Hz), 137.5, 138.3, 139.3, 143.9 and 158.9 (d, J=250.1 Hz). $^1$H NMR (DMSO-$d_6$): δ 4.39 (2H, d, J=5.5 Hz), 5.20 (1H, t, J=5.5 Hz), 6.97 (1H, d, J=7.6 Hz), 7.02 (1H, d, J=8.8 Hz), 7.15 (1H, s), 7.18 (1H, t, J=7.6 Hz), 7.40 (1H, m), 7.58 (2H, d, J=8.8 Hz), 7.72 (2H, d, J=7.9 Hz), 7.88 (2H, d, J=8.2 Hz) and 10.40 (1H, br s).

Synthesis 34

4'-Acetamidobiphenyl-4-sulfonic acid-(3-hydroxymethyl-phenyl)-amide (ABD576)

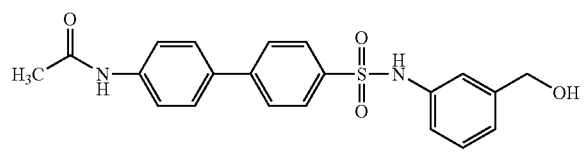 [SMILES: CC(=O)Nc1ccc(-c2ccc(S(=O)(=O)Nc3cccc(CO)c3)cc2)cc1]

Using a method analogous to Method C, with 4-bromo-N-(3-hydroxymethyl-phenyl)-benzenesulfonamide (ABD447) and 4-acetamido-phenyl boronic acid, the title compound was obtained as a crystalline white solid. $^{13}$C NMR (DMSO-$d_6$): δ 24.1, 62.5, 117.8, 119.4, 122.0, 126.9, 127.4, 127.5, 127.7, 128.8, 132.5, 137.7, 137.8, 139.9, 143.8, 143.8 and 168.6. $^1$H NMR (DMSO-$d_6$): δ 2.06 (3H, s), 4.38 (2H, m), 5.18 (1H, m), 6.95 (2H, m), 7.13 (1H, s), 7.14 (1H, m), 7.67 (4H, m), 7.81 (4H, m), 10.09 (1H, s) and 10.35 (1H, s).

Synthesis 35

4'-Methanesulfonylbiphenyl-4-sulfonic acid-(3-hydroxymethyl-phenyl)-amide (ABD577)

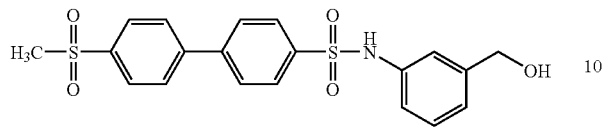

Using a method analogous to Method C, with 4-bromo-N-(3-hydroxymethyl-phenyl)-benzenesulfonamide (ABD447) and 4-methanesulfonyl-phenyl boronic acid, the title compound was obtained as a crystalline white solid. $^{13}$C NMR (DMSO-$d_6$): δ 43.5, 62.5, 117.9, 118.2, 122.1, 127.5, 127.9, 128.3, 128.8, 129.2, 137.5, 139.6, 140.6, 142.5, 143.2 and 143.9. $^1$H NMR (DMSO-$d_6$): δ 3.27 (3H, s), 4.39 (2H, s), 5.21 (1H, s), 6.97 (1H, d, J=7.3 Hz), 7.02 (1H, d, J=8.5 Hz), 7.15 (1H, s), 7.18 (1H, t, J=7.3 Hz), 7.90-8.04 (8H, m) and 10.42 (1H, s).

Synthesis 36

4'-Fluorobiphenyl-4-sulfonic acid-(3-hydroxymethyl-2-methylphenyl)-amide (ABD578)

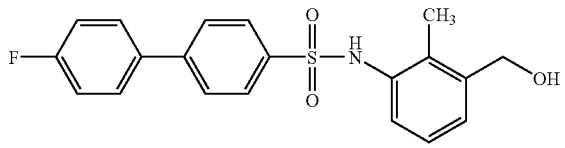

Using a method analogous to Method C, with 4-bromo-N-(3-hydroxymethyl-2-methyl-phenyl)-benzenesulfonamide (ABD524) and 4-fluoro-phenyl boronic acid, the title compound was obtained as a crystalline white solid. $^{13}$C NMR (DMSO-$d_6$): δ 12.8, 61.3, 116.0, 116.4, 125.4, 125.5, 127.3, 127.5, 129.2, 132.6, 134.5, 134.8 (d, J=2.9 Hz), 139.3, 141.7, 142.9 and 162.4 (d, J=246.1 Hz). $^1$H NMR (DMSO-$d_6$): δ 1.99 (3H, s), 4.41 (2H, d, J=5.2 Hz), 5.10 (1H, t, J=5.2 Hz), 6.82 (1H, d, J=7.9 Hz), 7.06 (1H, t, J=7.6 Hz), 7.24 (1H, d, J=7.3 Hz), 7.33 (2H, t, J=8.8 Hz), 7.72 (2H, t, J=8.2 Hz), 7.78 (2H, m), 7.83 (2H, d, J=8.2 Hz) and 9.63 (1H, s).

Synthesis 37

Biphenyl-4-sulfonic acid-(3-hydroxymethyl-phenyl)-amide (ABD579)

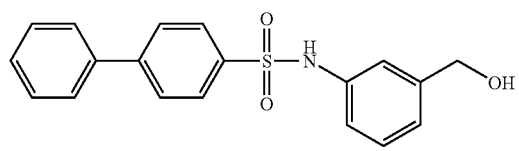 [SMILES: O=S(=O)(Nc1cccc(CO)c1)c1ccc(-c2ccccc2)cc1]

Using a method analogous to Method A, With biphenyl-sulfonyl chloride and (3-amino-phenyl)-methanol, the title compound was obtained as a white powder. $^1$H NMR (DMSO-$d_6$): δ 4.40 (2H, s), 5.20 (1H, br s), 6.96 (1H, d, J=7.6 Hz), 7.02 (1H, s, J=8.2 Hz), 7.15 (1H, s), 7.18 (1H, t, J=7.3 Hz), 7.46 (3H, m), 7.69 (2H, d, J=7.0 Hz), 7.85 (4H, s) and 10.36 (1H, s).

Synthesis 38

2'-Fluoro-biphenyl-4-sulfonic acid (3-hydroxymethyl-phenyl)-amide (ABD588)

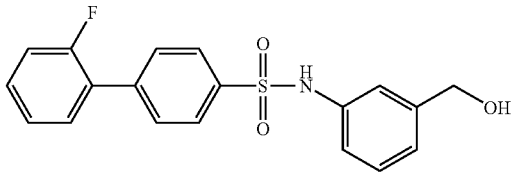 [SMILES: O=S(=O)(Nc1cccc(CO)c1)c1ccc(-c2ccccc2F)cc1]

Using a method analogous to Method C, with 4-bromo-N-(3-hydroxymethyl-phenyl)-benzenesulfonamide (ABD447) and 2-fluoro-phenyl boronic acid, the title compound was obtained as a crystalline white solid. $^{13}$C NMR (DMSO-$d_6$): δ 62.6, 116.3, 117.6, 117.9, 122.1, 125.3, 126.6 (d, J=12.7 Hz), 127.2, 129.0, 129.6, 129.8, 130.7, 137.6, 139.0, 139.4, 143.9 and 159.0 (d, J=247.1 Hz). $^1$H NMR (DMSO-$d_6$): δ 4.40 (1H, s), 5.21 (1H, m), 6.97 (1H, d, J=7.3 Hz), 7.03 (1H, d, J=8.5 Hz), 7.15 (1H, s), 7.18 (1H, t, J=7.9 Hz), 7.30 (1H, m), 7.35 (1H, d, J=7.9 Hz), 7.44 (1H, m), 7.54 (1H, t, J=7.6 Hz), 7.73 (2H, d, J=7.6 Hz), 7.88 (2H, d, J=8.5 Hz), and 10.40 (1H, br s).

Synthesis 39

4'-Methyl-biphenyl-4-sulfonic acid (3-hydroxymethyl-phenyl)-amide (ABD589)

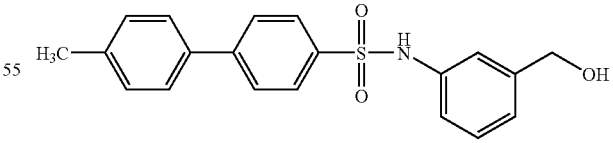

Using a method analogous to Method C, with 4-bromo-N-(3-hydroxymethyl-phenyl)-benzenesulfonamide (ABD447) and 4-methyl-phenyl boronic acid, the title compound was obtained as a crystalline white solid. $^1$H NMR (DMSO-$d_6$): δ 2.33 (3H, s), 4.39 (2H, d, J=5.2 Hz), 5.22 (1H, t, J=5.2 Hz), 6.96 (1H, d, J=7.6 Hz), 7.02 (1H, d, J=8.8 Hz), 7.17 (2H, m), 7.28 (2H, d, J=7.9 Hz), 7.60 (2H, d, J=7.9 Hz), 7.82 (4H, m) and 10.36 (1H, s)

Synthesis 40

2'-Chloro-biphenyl-4-sulfonic acid (3-hydroxymethyl-phenyl)-amide (ABD601)

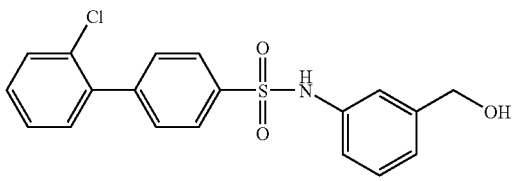

Using a method analogous to Method C, with 4-bromo-N-(3-hydroxymethyl-phenyl)-benzenesulfonamide (ABD447) and 2-chloro-phenyl boronic acid, the title compound was obtained as a clear oil. $^{13}$C NMR (CDCl$_3$): δ 64.6, 120.0, 120.5, 123.8, 127.0, 127.1, 129.5, 130.2, 131.2, 132.2, 136.8, 138.1, 138.6, 142.4 and 144.1

Synthesis 41

Diethyl 5-aminoisophthalate (ABD539)

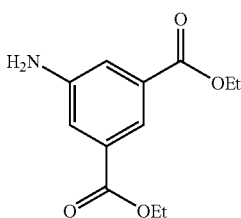 [SMILES: CCOC(=O)c1cc(N)cc(C(=O)OCC)c1]

Method D:

5-Aminoisophthalic acid (5 g) was suspended in ethanol (100 mL) and conc H$_2$SO$_4$ (20 mL) added. The mixture was refluxed for 12 hours and the ethanol evaporated under vacuum. Water was added to the residue and the solution neutralised with NaHCO$_3$ solution. The precipitate was collected, washed with water and extracted with ethyl acetate. The organic was dried, partially evaporated and addition of petrol gave the title compound as pale yellow crystals.

Synthesis 42

Ethyl 5-amino-2-hydroxybenzoate (ABD541)

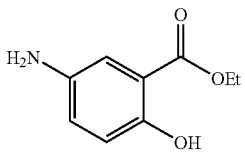 [SMILES: CCOC(=O)c1cc(N)ccc1O]

Using a method analogous to Method D, with 5-amino-2-hydroxybenzoic acid, the title compound was obtained as a pale brown solid.

Synthesis 43

Diethyl 4-aminophthalate (ABD546)

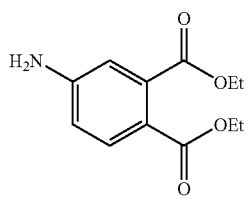 [SMILES: CCOC(=O)c1ccc(N)cc1C(=O)OCC]

Using a method analogous to Method D, with 4-aminophthalic acid, the title compound was obtained as a pale brown solid after purification by column chromatography

Synthesis 44

Ethyl 5-amino-4-hydroxybenzoate (ABD552)

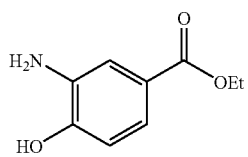 [SMILES: CCOC(=O)c1ccc(O)c(N)c1]

Using a method analogous to Method D, with 5-amino-4-hydroxybenzoic acid, the title compound was obtained as a brown oil which solidified on standing.

Synthesis 45

Diethyl 2-aminoterephthalate (ABD557)

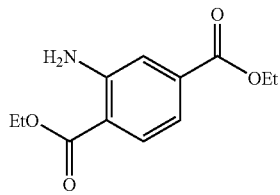 [SMILES: CCOC(=O)c1ccc(C(=O)OCC)c(N)c1]

Using a method analogous to Method D, with 4-aminophthalic acid, the title compound was obtained following purification by column chromatography, as a yellow oil which solidified on standing. $^{13}$C NMR (DMSO-d$_6$): δ 14.1, 60.3, 60.9, 112.0, 114.4, 117.6, 131.1, 134.4, 151.1, 165.4 and 166.9.

Synthesis 46

Ethyl 3-amino-4-hydroxybenzoate (ABD558)

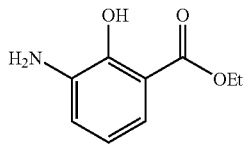

Using a method analogous to Method D, with 3-amino-2-hydroxybenzoic acid, the title compound was obtained as a brown oil which solidified on standing

Synthesis 47

Diethyl 3-aminophthalate (ABD560)

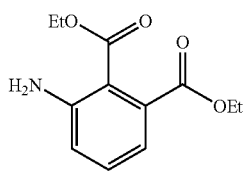 [SMILES: CCOC(=O)c1cccc(N)c1C(=O)OCC]

Using a method analogous to Method D, with 4-aminophthalic acid, the title compound was obtained as a yellow oil which solidified on standing

Synthesis 48

Ethyl 3-aminobenzoate (ABD608)

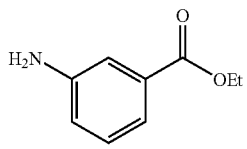 [SMILES: CCOC(=O)c1cccc(N)c1]

Using a method analogous to Method D, with 3-aminobenzoic acid, the title compound was obtained as a pale brown oil

Synthesis 49

Ethyl 3-aminobenzoate (ABD614)

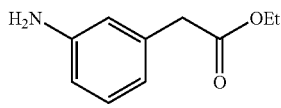

Using a method analogous to Method D, with 3-aminophenyl acetic acid, the title compound was obtained as a pale brown oil

Synthesis 50

Diethyl 5-(4-bromophenylsulfonamido)isophthalate (ABD542)

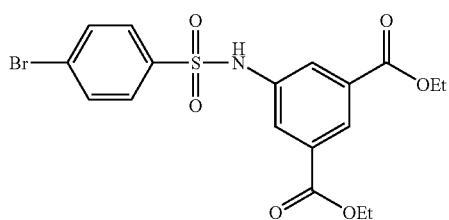 [SMILES: CCOC(=O)c1cc(NS(=O)(=O)c2ccc(Br)cc2)cc(C(=O)OCC)c1]

Using a method analogous to Method A, with 4-bromophenyl sulfonylchloride and diethyl 5-aminoisophthalate (ABD539), the title compound was obtained as a white crystalline solid.

Synthesis 51

Diethyl 5-(2',4'-dichlororobiphenyl-4-yl sulfonamido)isophthalate (ABD543)

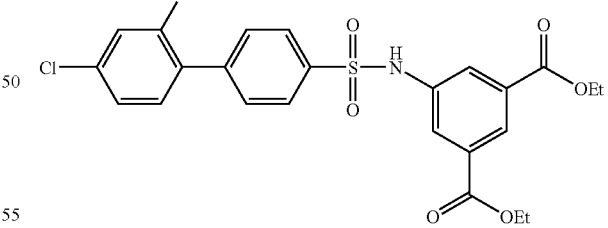

Using a method analogous to Method C, with diethyl 5-(4-bromophenylsulfonamido) isophthalate (ABD542) and 2,4-dichlorophenylboronic acid, the title compound was obtained as a crystalline white solid. $^{13}$C NMR (DMSO-$d_6$): δ14.3, 61.9, 125.8, 127.0, 127.2, 127.5, 130.0, 130.3, 131.8, 132.2, 133.0, 135.0, 137.0, 137.5, 138.2, 143.4 and 165.3. $^1$H NMR (DMSO-$d_6$): δ 1.39 (6H, t, J=7.0 Hz), 4.41 (4H, q, J=7.0 Hz), 7.18 (1H, d, J=8.2 Hz), 7.28 (1H, t, J=8.2 Hz), 7.47 (3H, m), 7.55 (1H, s), 7.86 (2H, d, J=8.2 Hz), 8.06 (2H, s) and 8.41 (1H, s).

Synthesis 52

Ethyl-5-(4'-bromobiphenyl-4-yl-sulfonamido)-2-hydroxybenzoate (ABD544)

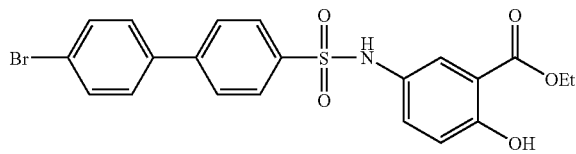 [SMILES: CCOC(=O)c1cc(NS(=O)(=O)c2ccc(-c3ccc(Br)cc3)cc2)ccc1O]

Using a method analogous to Method A, with 4-bromobiphenyl sulfonylchloride and ethyl 5-amino-2-hydroxybenzoate (ABD541), the title compound was obtained as deep pink needles. $^{13}$C NMR (DMSO-$d_6$): δ 13.8, 61.6, 113.2, 118.3, 122.2, 123.3, 126.8, 127.3, 128.6, 129.0, 130.2, 132.0, 137.2, 138.1, 143.0, 157.4 and 168.1. $^1$H NMR (CDCl$_3$): δ 1.35 (3H, t, J=7.0 Hz), 4.35 (2H, q, J=7.0 Hz), 6.33 (1H, s), 6.86 (1H, d, J=8.8 Hz), 7.13 (1H, dd, J=8.8, 2.8 Hz), 7.43 (2H, d, J=8.5 Hz), 7.45 (1H, m), 7.59 (2H, d, J=8.2 Hz), 7.62 (2H, d, J=8.2 Hz), 7.76 (2H, d, J=8.5 Hz) and 10.80 (1H, s)

Synthesis 53

Diethyl 4-(4-bromophenylsulfonamido)phthalate (ABD548)

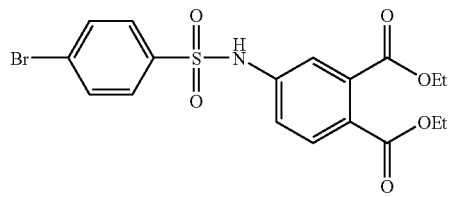 [SMILES: CCOC(=O)c1ccc(NS(=O)(=O)c2ccc(Br)cc2)cc1C(=O)OCC]

Using a method analogous to Method A, with 4-bromophenyl sulfonylchloride and diethyl 4-aminoisophthalate (ABD546), the title compound was obtained as a white crystalline solid. $^{13}$C NMR (DMSO-$d_6$): δ 14.0, 14.1, 61.8, 62.2, 119.7, 121.1, 127.3, 128.7, 130.9, 132.6, 134.6, 137.7, 139.5, 166.5 and 167.7. $^1$H NMR (CDCl$_3$): δ 1.32 (6H, t, J=7.0 Hz), 4.31 (4H, q, J=7.0 Hz), 7.31 (2H, m), 7.54 (2H, d, J=8.5 Hz), 7.66 (2H, d, J=8.5 Hz), 7.67 (1H, d, J=8.5 Hz) and 8.02 (1H, s)

Synthesis 54

Diethyl 4-(2',4'-dichlororobiphenyl-4-yl-sulfonamido)phthalate (ABD549)

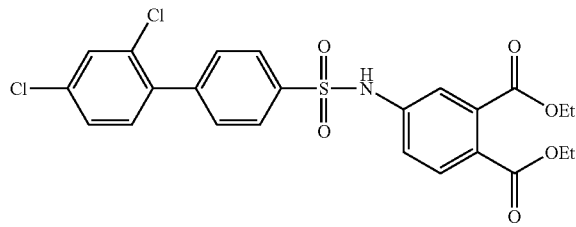 [SMILES: CCOC(=O)c1ccc(NS(=O)(=O)c2ccc(-c3ccc(Cl)cc3Cl)cc2)cc1C(=O)OCC]

Using a method analogous to Method C, with diethyl 4-(4-bromophenylsulfonamido) phthalate (ABD548) and 2,4-dichlorophenylboronic acid, the title compound was obtained as a crystalline white solid. $^{13}$C NMR (DMSO-$d_6$): δ 14.0, 14.1, 61.7, 62.0, 119.5, 120.9, 127.0, 127.1, 127.5, 130.0, 130.4, 130.9, 131.9, 133.0, 134.7, 134.9, 137.0, 138.2, 139.9, 143.4, 166.5 and 167.6.

Synthesis 55

Ethyl-5-(4'-bromobiphenyl-4-yl-sulfonamido)-4-hydroxybenzoate (ABD553)

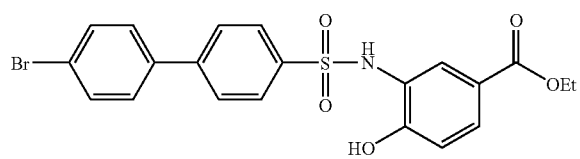 [SMILES: CCOC(=O)c1ccc(O)c(NS(=O)(=O)c2ccc(-c3ccc(Br)cc3)cc2)c1]

Using a method analogous to Method A, with 4-bromobiphenyl sulfonylchloride and ethyl 5-amino-4-hydroxybenzoate (ABD552), the title compound was obtained as deep pink needles. $^{13}$C NMR (DMSO-$d_6$): δ 14.2, 60.3, 115.8, 116.1, 120.6, 122.2, 124.1, 127.0, 127.3, 127.6, 129.3, 132.0, 137.5, 139.7, 142.7, 155.2 and 165.2. $^1$H NMR (CDCl$_3$): δ 1.25 (3H, t, J=7.0 Hz), 4.21 (2H, q, J=7.0 Hz), 6.82 (1H, d, J=8.5 Hz), 7.60 (1H, d, J=8.2 Hz), 7.67-7.82 (9H, m) and 10.15 (1H, s).

Synthesis 56

Diethyl 4-(4-bromophenylsulfonamido)phthalate (ABD561)

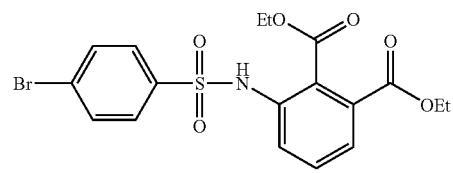 [SMILES: CCOC(=O)c1cccc(NS(=O)(=O)c2ccc(Br)cc2)c1C(=O)OCC]

Using a method analogous to Method A, with 4-bromophenyl sulfonylchloride and diethyl 4-aminophthalate (ABD560), the title compound was obtained as an orange crystalline solid.

Synthesis 57

Diethyl 4-(2',4'-difluororobiphenyl-4-yl-sulfonamido)phthalate (ABD562)

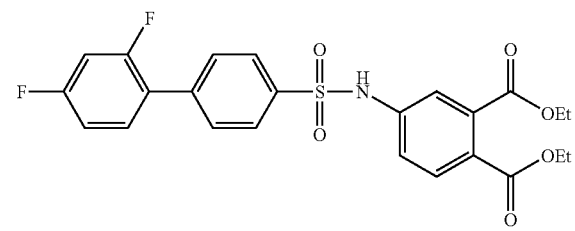 [SMILES: CCOC(=O)c1ccc(NS(=O)(=O)c2ccc(-c3ccc(F)cc3F)cc2)cc1C(=O)OCC]

Using a method analogous to Method C, with diethyl 4-(4-bromophenylsulfonamido) phthalate (ABD548) and 2,4-difluorophenylboronic acid, the title compound was obtained as a brown oil.

Synthesis 58

Diethyl 4-(4'-fluororobiphenyl-4-yl-sulfonamido) phthalate (ABD566)

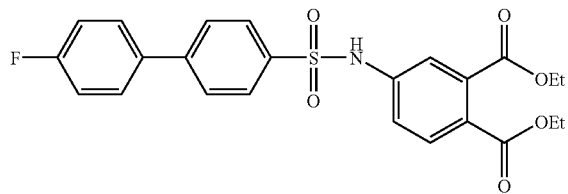 [SMILES: CCOC(=O)c1ccc(NS(=O)(=O)c2ccc(-c3ccc(F)cc3)cc2)cc1C(=O)OCC]

Using a method analogous to Method C, with diethyl 4-(4-bromophenylsulfonamido) phthalate (ABD548) and 4-fluorophenylboronic acid, the title compound was obtained as a brown oil.

Synthesis 59

Diethyl 4-(4'-fluororobiphenyl-4-yl-sulfonamido) phthalate (ABD567)

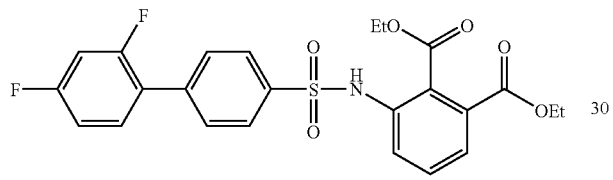

Using a method analogous to Method C, with diethyl 3-(4-bromophenylsulfonamido) phthalate (ABD561) and 2,4-difluorophenylboronic acid, the title compound was obtained as white crystals.

Synthesis 60

Ethyl-5-(4'-bromophenyl-4-yl-sulfonamido)-2-hydroxybenzoate (ABD572)

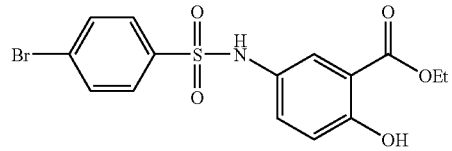 [SMILES: CCOC(=O)c1cc(NS(=O)(=O)c2ccc(Br)cc2)ccc1O]

Using a method analogous to Method A, with 4-bromobiphenyl sulfonylchloride and ethyl 5-amino-2-hydroxybenzoate (ABD541), the title compound was obtained as a lilac powder.

Synthesis 61

Ethyl-5-(4'-bromophenyl-4-yl-sulfonamido)-2-hydroxybenzoate (ABD573)

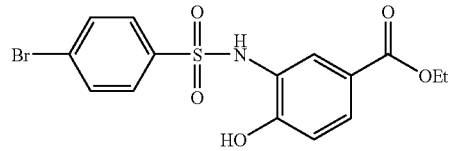 [SMILES: CCOC(=O)c1ccc(O)c(NS(=O)(=O)c2ccc(Br)cc2)c1]

Using a method analogous to Method A, with 4-bromobiphenyl sulfonylchloride and ethyl 5-amino-4-hydroxybenzoate (ABD552), the title compound was obtained as a pale pink powder.

Synthesis 62

3-(4'-bromobiphenyl-4-ylsulfonamido)-2-hydroxybenzoate (ABD583)

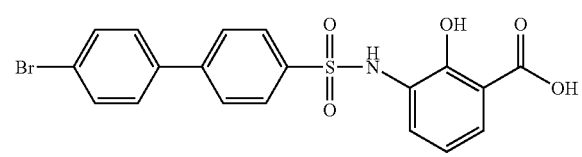 [SMILES: O=C(O)c1cccc(NS(=O)(=O)c2ccc(-c3ccc(Br)cc3)cc2)c1O]

Using a method analogous to Method A, with 4-bromobiphenyl sulfonylchloride and 3-amino-2-hydroxybenzoic acid, the title compound was obtained as an impure grey powder Synthesis 63

Ethyl 3-(2',4'-difluorobiphenyl-4-ylsulfonamido)-4-hydroxybenzoate (ABD584)

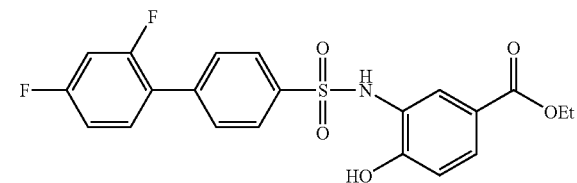 [SMILES: CCOC(=O)c1ccc(O)c(NS(=O)(=O)c2ccc(-c3ccc(F)cc3F)cc2)c1]

Using a method analogous to Method C, with ethyl-5-(4-bromophenyl-4-ylsulfonamido)-4-hydroxybenzoate (ABD573) and 2,4-difluorophenylboronic acid, the title compound was obtained as a pale brown powder Synthesis 64

Ethyl 3-(2',4'-difluorobiphenyl-4-ylsulfonamido)-4-hydroxybenzoate (ABD586)

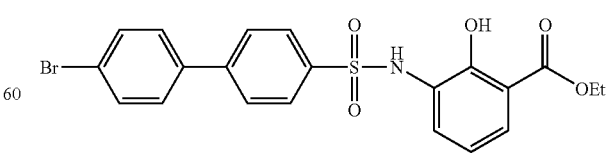

Using a method analogous to Method D, with 3-(4'-bromobiphenyl-4-ylsulfonamido)-2-hydroxybenzoate

Synthesis 65

3-(Biphenyl-4-ylsulfonamido)benzoic acid (ABD590)

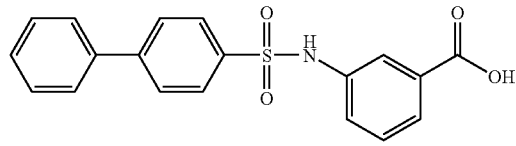

Using a method analogous to Method A, with biphenyl sulfonylchloride and 3-aminobenzoic, the title compound was obtained as a white crystalline solid.

Synthesis 66

Ethyl 3-(4-bromophenyl-4-ylsulfonamido)benzoate (ABD611)

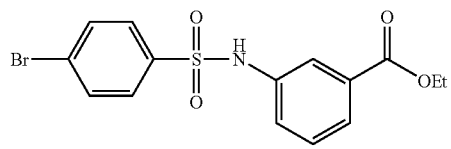 [SMILES: CCOC(=O)c1cccc(NS(=O)(=O)c2ccc(Br)cc2)c1]

Using a method analogous to Method A, with 4-bromobiphenyl sulfonylchloride and ethyl 3-amino-benzoate (ABD608), the title compound was obtained as a white powder.

Synthesis 67

Ethyl 3-(2',4'-dichlorobiphenyl-4-yl sulfonamido)benzoate (ABD612)

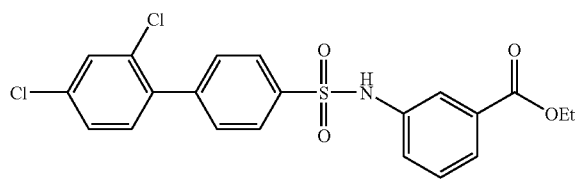 [SMILES: CCOC(=O)c1cccc(NS(=O)(=O)c2ccc(-c3ccc(Cl)cc3Cl)cc2)c1]

Using a method analogous to Method C, with ethyl-5-(4-bromophenyl-4-ylsulfonamido)benzoate (ABD611) and 2,4-dichlorophenylboronic acid, the title compound was obtained as white crystals. $^{13}$C NMR (DMSO-d$_6$): δ 14.1, 61.0, 120.3, 124.5, 125.2, 126.5, 126.9, 127.8, 129.9, 130.2, 130.8, 132.2, 133.1, 133.8, 137.1, 138.1, 138.9, 142.0 and 165.1. $^1$H NMR (DMSO-d$_6$): δ 1.27 (3H, t, J=7.3 Hz), 4.26 (2H, q, J=7.0 Hz), 7.39 (1H, d; J=7.9 Hz), 7.42 (1H, d, J=7.3 Hz), 7.43 (1H, s), 7.50 (1H, dd, J=8.2, 1.9 Hz), 7.60 (1H, m), 7.62 (2H, d, J=8.2 Hz), 7.74 (1H, s), 7.86 (2H, d, J=8.5 Hz) and 10.70 (1H, s).

Synthesis 68

3-(4-bromophenyl-4-ylsulfonamido)benzoic acid (ABD613)

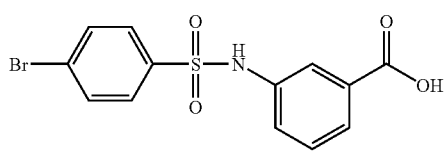 [SMILES: O=C(O)c1cccc(NS(=O)(=O)c2ccc(Br)cc2)c1]

Using a method analogous to Method A, with 4-bromobiphenyl sulfonylchloride and 3-amino-benzoic acid, the title compound was obtained as a pale pink powder. $^{13}$C NMR (DMSO-d$_6$): δ 120.8, 124.3, 125.4, 127.1, 128.7, 129.6, 131.8, 132.5, 137.7, 138.4 and 166.7. $^1$H NMR (DMSO-d$_6$): δ 7.32 (1H, d, J=8.5 Hz), 7.37 (1H, d, J=7.6 Hz), 7.62 (2H, d, J=7.0 Hz), 7.68 (2H, m), 7.78 (2H, d, J=8.5 Hz), 10.64 (1H, s) and 13.02 (1H, br s).

Synthesis 69

3-(2',4'-Dichlorobiphenyl-4-ylsulfonamido)benzoic acid (ABD615)

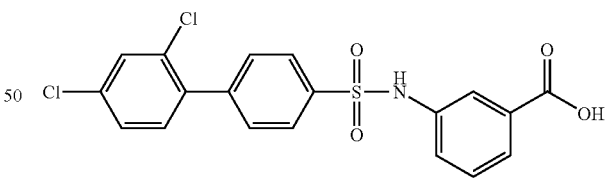

Ethyl 3-(2',4'-dichlorobiphenyl-4-ylsulfonamido)benzoate (ABD612) (0.4 g) was dissolved in a mixture of THF (5 ml) and methanol (5 ml). 1M NaOH (10 ml) was added and the mixture stirred for 3 hrs at room temperature followed by 1 h at 50° C., by which stage clear solution had formed. Conc. HCl was added and the precipitate collected as a white solid. The solid was dissolved in ethyl acetate and dried with Na$_2$SO$_4$. Evaporation gave the title compound as a white solid, recrystallised from ethyl acetate/petrol. $^{13}$C NMR (DMSO-d$_6$): δ 122.4, 124.1, 125.0, 126.3, 126.5, 127.7, 129.6, 130.4, 131.9, 132.2, 132.5, 133.8, 137.1, 137.9, 138.9, 142.0 and 166.8.

Synthesis 70

Ethyl 2-(3-(4-bromophenylsulfonamido)phenyl)acetate (ABD616)

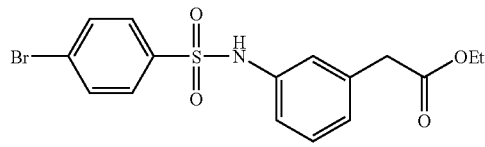 [SMILES: CCOC(=O)Cc1cccc(NS(=O)(=O)c2ccc(Br)cc2)c1]

Using a method analogous to Method A, with 4-bromophenyl sulfonylchloride and ethyl 2-(3-aminophenyl)acetate (ABD614), the title compound was obtained as a white powder.

Synthesis 71

Ethyl 3-(2',4'-dichlorobiphenyl-4-yl sulfonamido)benzoate (ABD617)

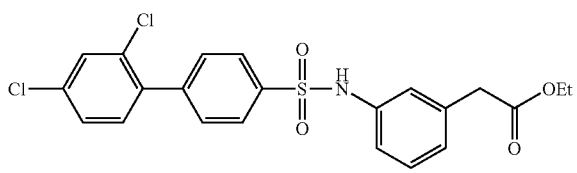 [SMILES: CCOC(=O)Cc1cccc(NS(=O)(=O)c2ccc(-c3ccc(Cl)cc3Cl)cc2)c1]

Using a method analogous to Method C, with ethyl 2-(3-(4-bromophenylsulfonamido) phenyl)acetate (ABD616) and 2,4-dichlorophenylboronic acid, the title compound was obtained as a clear oil. $^{13}$C NMR (CDCl$_3$): δ 14.2, 41.1, 61.1, 120.2, 122.5, 126.4, 127.1, 127.5, 129.5, 130.0, 130.1, 131.9, 133.0, 134.8, 135.5, 136.7, 137.2, 138.5, 142.9 and 171.4.

Synthesis 72

Ethyl 3-(2',4'-difluorobiphenyl-4-yl sulfonamido)benzoate (ABD620)

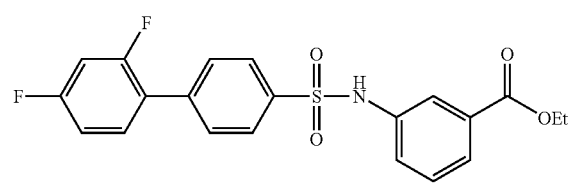 [SMILES: CCOC(=O)c1cccc(NS(=O)(=O)c2ccc(-c3ccc(F)cc3F)cc2)c1]

Using a method analogous to Method C, with ethyl-5-(4-bromophenyl-4-ylsulfonamido)benzoate (ABD611) and 2,4-difluorophenylboronic acid, the title compound was obtained as white crystals. $^{13}$C NMR (DMSO-d$_6$): δ 14.1, 61.0, 104.9 (m), 112.5 (m), 120.1, 123.0, 124.6, 126.8, 127.2, 129.6, 129.8, 130.9, 132.0, 138.1, 138.6, 138.8, 159.0 (dd, J=259.0, 12.7 Hz), 162.2 (dd, J=259.0, 12.7 Hz) and 165.2. $^1$H NMR (DMSO-d$_6$): δ 1.26 (3H, t, J=7.0 Hz), 4.25 (2H, q, J=7.0 Hz), 7.19 (1H, t, J=7.0 Hz), 7.41 (3H, m), 7.43 (1H, s), 7.59 (2H, m), 7.70 (2H, d, J=8.8 Hz), 7.73 (1H, m), 7.86 (2H, d, J=8.2 Hz) and 10.67 (1H, s).

Synthesis 73

Ethyl 2-(3-(4'-bromobiphenylsulfonamido)phenyl) acetate (ABD623)

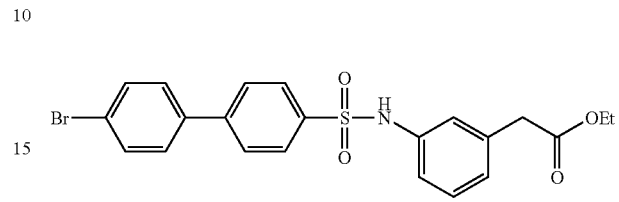

Using a method analogous to Method A, with 4-bromobiphenyl sulfonylchloride and ethyl 2-(3-aminophenyl)acetate (ABD614), the title compound was obtained as a clear oil. $^1$H NMR (DMSO-d$_6$): δ 1.12 (3H, t, J=7.0 Hz), 3.54 (2H, s), 4.00 (2H, q, J=7.0 Hz), 6.90 (1H, d, J=7.3 Hz), 6.99 (1H, m), 7.03 (1H, s), 7.17 (1H, t, J=7.6 Hz), 7.65 (4H, m), 7.83 (4H, m) and 10.37 (1H, br s).

Synthesis 74

Ethyl 3-(2',4'-difluorobiphenyl-4-ylsulfonamido) benzoate (ABD626)

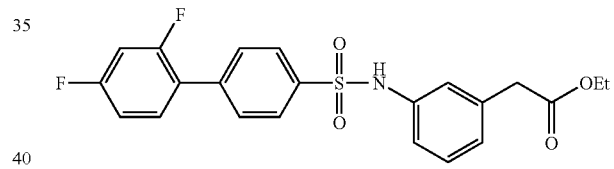

Using a method analogous to Method C, with ethyl 2-(3-(4-bromophenylsulfonamido) phenyl)acetate (ABD616) and 2,4-difluorophenylboronic acid, the title compound was obtained as a clear oil.

Synthesis 75

N-(3,5-Bis(hydroxymethyl)phenyl)-2',4'-dichlorobiphenyl-4-sulfonamide (ABD545)

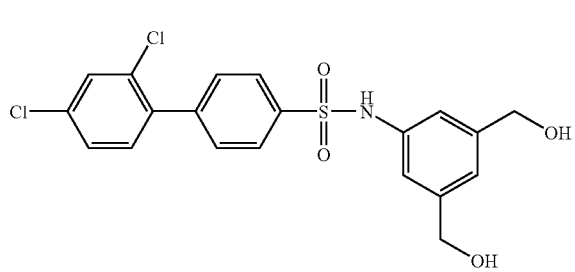 [SMILES: O=S(=O)(Nc1cc(CO)cc(CO)c1)c1ccc(-c2ccc(Cl)cc2Cl)cc1]

Using a method analogous to Method B, with diethyl 5-(2',4'-dichlorobiphenyl-4-ylsulfonamido)isophthalate (ABD543), the title compound was obtained as a white powder. $^{13}$C NMR (DMSO-$d_6$): δ 62.5, 116.2, 120.3, 127.1, 127.7, 128.6, 129.2, 133.6, 137.0, 138.1, 138.2, 138.6, 143.0, 143.3 and 144.3. $^1$H NMR (CDCl$_3$): δ 4.37 (2H, s), 4.39 (2H, s), 5.17 (2H, t, J=5.5 Hz), 6.91 (1H, s), 7.02 (2H, s), 7.50 (2H, d, J=8.5 Hz), 7.72 (2H, t, J=8.5 Hz), 7.85 (4H, s) and 10.32 (1H, s).

Synthesis 76

4'-Bromo-N-(4-hydroxy-3-(hydroxymethyl)biphenyl)-4-sulfonamide (ABD547)

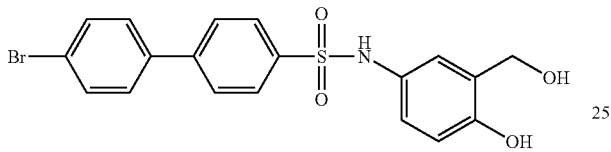

Using a method analogous to Method B, with ethyl-5-(4'-bromobiphenyl-4-ylsulfonamido)-2-hydroxybenzoate (ABD544), the title compound was obtained as a pale brown powder. $^{13}$C NMR (DMSO-$d_6$): δ 57.9, 114.6, 121.2, 121.6, 126.8, 127.2, 127.6, 128.5, 128.8, 129.1, 129.4, 138.4, 138.6, 143.9 and 151.4.

Synthesis 77

N-(3,4-Bis(hydroxymethyl)phenyl)-2',4'-dichlorobiphenyl-4-sulfonamide (ABD550)

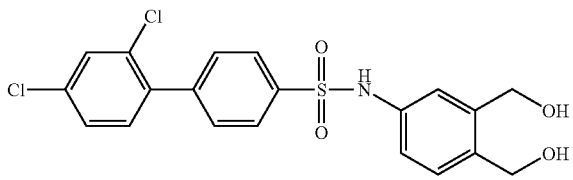 [SMILES: O=S(=O)(Nc1ccc(CO)c(CO)c1)c1ccc(-c2ccc(Cl)cc2Cl)cc1]

Using a method analogous to Method B, with diethyl 4-(2', 4'-dichlororobiphenyl-4-ylsulfonamido)phthalate (ABD549), the title compound was obtained as a white powder. $^{13}$C NMR (DMSO-$d_6$): δ 59.9, 60.0, 117.6, 118.2, 126.9, 127.3, 127.6, 127.8, 129.0, 129.3, 134.8, 136.3, 137.1, 138.3, 138.6, 140.8, 142.8 and 144.2. $^1$H NMR (CDCl$_3$): δ 4.38 (2H, d, J=5.6 Hz), 4.43 (2H, d, J=4.6 Hz), 4.96 (1H, t, J=5.8 Hz), 5.10 (1H, t, J=5.8 Hz) 7.01 (1H, d, J=7.6 Hz), 7.20 (1H, d, J=8.2 Hz), 7.47 (2H, m), 7.71 (1H, t, J=7.6 Hz), 7.83 (5H, m) and 10.31 (1H, s).

Synthesis 78

4'-Bromo-N-(2-hydroxy-5-(hydroxymethyl)biphenyl)-4-sulfonamide (ABD554)

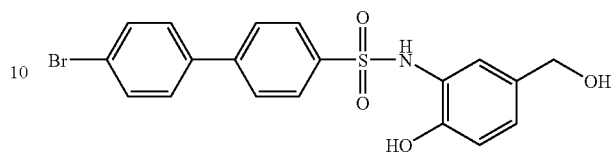

Using a method analogous to Method B, with ethyl-5-(4'-bromobiphenyl-4-yl-sulfonamido)-4-hydroxybenzoate (ABD553), the title compound was obtained as a pale brown powder. $^{13}$C NMR (DMSO-$d_6$): δ 63.2, 115.7, 115.8, 124.0, 124.3, 125.4, 127.6, 128.1, 129.1, 129.8, 133.8, 139.1, 140.2, 144.5 and 149.7.

Synthesis 79

N-(3,4-Bis(hydroxymethyl)phenyl)-2',4'-difluorobiphenyl-4-sulfonamide (ABD565)

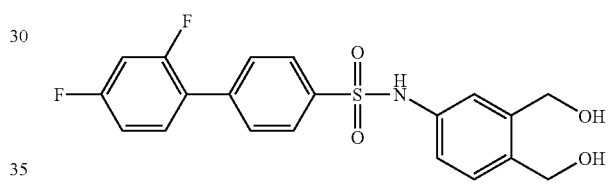

Using a method analogous to Method B, with diethyl 4-(2', 4'-difluororobiphenyl-4-ylsulfonamido)phthalate (ABD562), the title compound was obtained as a white powder. $^{13}$C NMR (DMSO-$d_6$): δ 60.5, 60.6, 105.4 (t, J=25.0 Hz), 112.9 (d, J=18 Hz), 116.6, 118.2, 119.0, 127.7, 128.4, 130.2, 132.7 (m), 135.5, 136.9, 139.2, 139.8, 141.5, 159.9 (dd, J=248.5, 12.2 Hz) and 163.0 (dd, J=247.0, 12.2 Hz). $^1$H NMR (CDCl$_3$): δ 4.40 (2H, d, J=4.7 Hz), 4.46 (2H, d, J=4.9 Hz), 5.00 (1H, t, J=5.5 Hz), 5.14 (1H, t, J=5.5 Hz), 7.03 (1H, d, J=8.2 Hz), 7.22 (1H, d, J=8.2 Hz), 7.26 (2H, m), 7.39 (1H, m), 7.61 (1H, t, J=7.9 Hz), 7.71 (2H, d, J=7.6 Hz), 7.88 (2H, t, J=8.2) and 10.34 (1H, s)

Synthesis 80

N-(3,4-Bis(hydroxymethyl)phenyl)-4'-fluorobiphenyl-4-sulfonamide (ABD568)

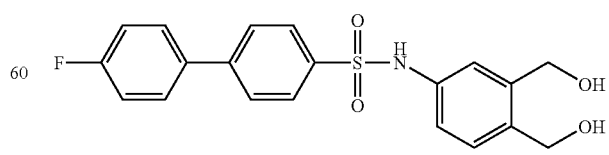

Using a method analogous to Method B, with diethyl 4-(4'-fluororobiphenyl-4-ylsulfonamido)phthalate (ABD566), the title compound was obtained as a white powder. $^{13}$C NMR (DMSO-d$_6$): δ 60.5, 60.6, 116.7 (d, J=21.2 Hz), 118.2, 119.0, 128.0, 128.4, 129.8 (m), 135.4, (m), 137.0, 139.2, 141.5, 143.8 and 163.1 (d, J=244.7).

Synthesis 81

N-(3,4-Bis(hydroxymethyl)phenyl)-4-bromophenyl-4-sulfonamide (ABD569)

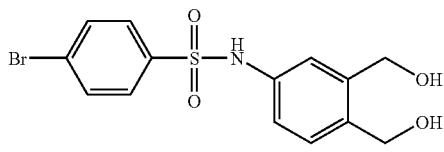 [SMILES: O=S(=O)(Nc1ccc(CO)c(CO)c1)c1ccc(Br)cc1]

Using a method analogous to Method B, with diethyl 4-(4-bromophenyl-4-ylsulfonamido)phthalate (ABD548), the title compound was obtained as a white powder. $^{13}$C NMR (DMSO-d$_6$): δ 59.9, 60.0, 117.7, 118.5, 126.6, 127.7, 129.0, 132.7, 134.8, 136.3, 139.7 and 140.8

Synthesis 82

2', 4'-Difluoro-N-(2-hydroxy-5-(hydroxymethyl) biphenyl)-4-sulfonamide (ABD585)

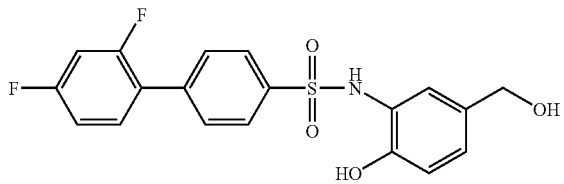 [SMILES: O=S(=O)(Nc1cc(CO)ccc1O)c1ccc(-c2ccc(F)cc2F)cc1]

Using a method analogous to Method B, with ethyl-5-(2', 4'-difluorobiphenyl-4-yl-sulfonamido)-4-hydroxybenzoate (ABD584), the title compound was obtained as a pale brown powder. $^{13}$C NMR (DMSO-d$_6$): δ 62.6, 105.1, 112.4, 115.2, 116.1, 122.6, 123.4, 124.7, 127.3, 127.4, 129.1, 133.2, 138.1, 140.2, 149.1, 159.9 (dd, J=248.5, 12.2 Hz) and 163.0 (dd, J=247.0, 12.2 Hz). $^1$H NMR (DMSO-d$_6$): δ 4.31 (2H, s), 5.07 (1H, s), 6.69 (1H, d, J=7.9 Hz), 6.88 (1H, d, J=7.9 Hz), 7.19 (1H, s), 7.30 (2H, m), 7.66 (2H, d, J=8.5 Hz), 7.80 (1H, m), 7.85 (2H, d, J=8.2 Hz) and 9.41 (2H, br s).

Synthesis 83

4'-Bromo-N-(2-hydroxy-3-(hydroxymethyl)biphenyl)-4-sulfonamide (ABD587)

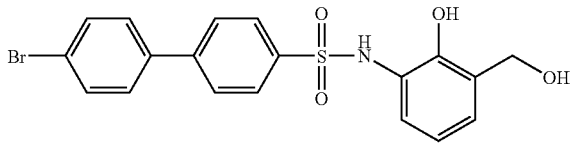 [SMILES: O=S(=O)(Nc1cccc(CO)c1O)c1ccc(-c2ccc(Br)cc2)cc1]

Using a method analogous to Method B, with ethyl-5-(4'-bromobiphenyl-4-yl-sulfonamido)-4-hydroxybenzoate (ABD586), the title compound was obtained as a pale brown powder. $^{13}$C NMR (DMSO-d$_6$): δ 58.8, 119.1, 123.0, 124.0, 124.7, 127.0, 127.3, 127.4, 128.4, 129.1, 129.9, 138.4, 139.0, 144.1 and 147.7. $^1$H NMR (DMSO-d$_6$): δ 4.45 (2H, s), 5.20 (1H, br s), 6.70 (1H, t, J=8.2 Hz), 6.90 (1H, d, J=7.6 Hz), 7.08 (1H, d, J=7.0 Hz), 7.47 (3H, m), 7.72 (2H, d, J=7.0 Hz), 7.83 (4H, m) and 9.10 (2H, br s)

Synthesis 84

4-Bromo-N-(3-(2-hydroxyethyl)phenyl)phenyl-4-sulfonamide (ABD624)

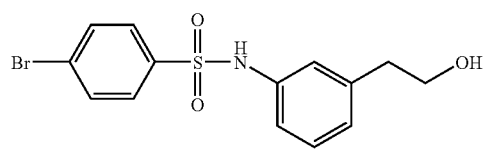 [SMILES: O=S(=O)(Nc1cccc(CCO)c1)c1ccc(Br)cc1]

Using a method analogous to Method B, with ethyl 2-(3-(4-bromophenylsulfonamido) phenyl)acetate (ABD616), the title compound was obtained as a clear oil.

Synthesis 85

2',4'-Dichloro-N-(3-(2-hydroxyethyl)phenyl)biphenyl-4-sulfonamide (ABD625)

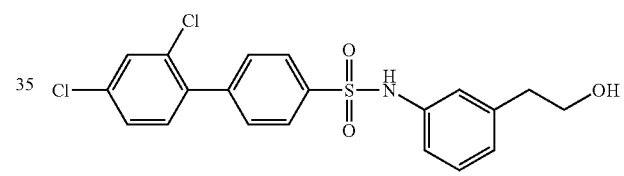

Using a method analogous to Method C, with 4-bromo-N-(3-(2-hydroxyethyl)phenyl)phenyl-4-sulfonamide (ABD624) and 2,4-difluorophenylboronic acid, the title compound was obtained as a clear oil. $^{13}$C NMR (CDCl$_3$): δ 38.8, 63.4, 119.5, 122.2, 126.1, 127.2, 127.5, 129.5, 130.0, 130.2, 131.9, 133.0, 134.8, 136.7, 137.1, 138.4, 140.2 and 142.9. $^1$H NMR (CDCl$_3$): δ 2.73 (2H, t, J=6.4 Hz), 3.73 (2H, m), 6.94 (1H, t, J=7.6 Hz), 6.97 (1H, s), 6.99 (1H, d, J=8.5 Hz), 7.17 (2H, m), 7.27 (1H, d, J=8.2 Hz), 7.42 (2H, d, J=8.2 Hz), 7.43 (1H, s), 7.83 (2H, d, J=8.2 Hz) and 7.93 (1H, s).

Synthesis 86

2',4'-Difluoro-N-(3-(2-hydroxyethyl)phenyl)biphenyl-4-sulfonamide (ABD628)

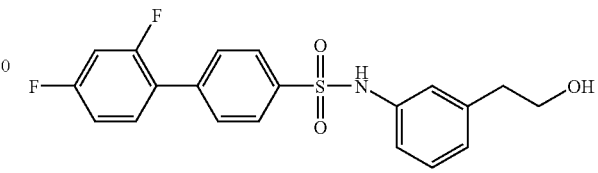

Using a method analogous to Method B, with ethyl 3-(2', 4'-difluorobiphenyl-4-yl sulfonamido)benzoate (ABD626), the title compound was obtained as a clear oil. $^{13}$C NMR (CDCl$_3$): δ 38.8, 63.3, 104.6 (t, J=26.4 Hz), 112.0 (dd, J=20.5, 2.9 Hz), 116.0 (d, J=6.9 Hz), 119.2 (d, J=8.9 Hz), 121.9 (d, J=5.9 Hz), 123.3 (dd, J=13.7, 3.9 Hz), 125.9, 127.5 (d, J=4.9 Hz), 127.9, 129.0 (d, J=7.8 Hz), 129.4, 131.5 (dd, J=9.8, 3.9 Hz), 135.1, 136.8 (d, J=4.9 Hz), 137.6, 138.2, 139.6, 140.2, 144.6, 159.6 (dd, J=252.0, 11.7 Hz) and 163.0 (dd, J=252.0, 11.7 Hz). $^1$H NMR (CDCl$_3$): δ 2.71 (2H, d, J=6.4 Hz), 3.72 (2H, m), 6.88 (2H, m), 7.01 (1H, s), 7.08 (2H, m), 7.28 (1H, m), H, m), 7.47 (2H, d, J=7.9 Hz), 7.83 (2H, d, J=7.0 Hz) and 8.15 (1H, s).

Synthesis 87

4'-Bromo-N-(3-(2-hydroxyethyl)phenyl)biphenyl-4-sulfonamide (ABD630)

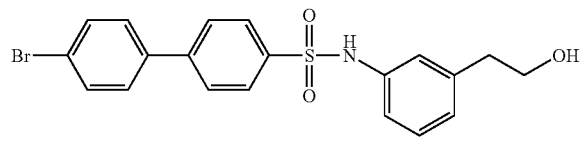 [SMILES: O=S(=O)(Nc1cccc(CCO)c1)c1ccc(-c2ccc(Br)cc2)cc1]

Using a method analogous to Method B, with ethyl 3-(4'-bromobiphenyl-4-yl sulfonamido)benzoate (ABD623), the title compound was obtained as a white solid. $^{13}$C NMR (DMSO-d$_6$): δ 38.7, 62.0, 117.5, 120.4, 122.3, 124.7, 127.3, 127.6, 128.9, 129.3, 132.2, 137.5, 137.5, 138.7, 140.7 and 143.0. $^1$H NMR (DMSO-d$_6$): δ 2.60 (2H, t, J=7.0 Hz), 3.45 (2H, m), 4.66 (1H, s), 6.87 (1H, d, J=7.6 Hz), 6.95 (1H, m), 6.98 (1H, s), 7.11 (1H, t, J=7.6 Hz), 7.64 (4H, m), 7.82 (4H, m) and 10.57 (1H, br s).

Synthesis 88

2',4'-Dichloro-N-(3-(hydroxymethyl)phenyl)-N-methylbiphenyl-4-sulfonamide (ABD600)

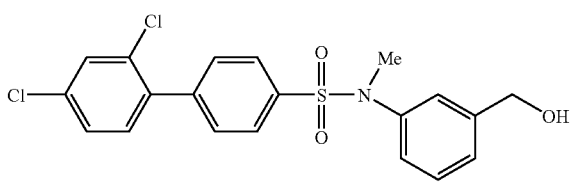

2',4'-Dichlorobiphenyl-4-sulfonic acid-(3-hydroxymethyl-phenyl)-amide (ABD455) (0.4 g) was dissolved in DMF (20 ml). K$_2$CO$_3$ (1 g) was added followed by methyl iodide (1 ml). The mixture was stirred vigorously for 3 hrs, poured into water and extracted with ether. After drying (Na$_2$SO$_4$), the solvent was partially removed under vacuum and petrol added to induce crystallisation and the product collected as white crystals. $^{13}$C NMR (CDCl$_3$): δ 38.4, 64.7, 125.3, 125.7, 126.0, 127.5, 127.7, 129.2, 129.8, 130.1, 131.9, 133.1, 134.9, 135.8, 137.2, 141.6, 142.0 and 142.8. $^1$H NMR (CDCl$_3$): δ 3.22 (3H, s), 4.65 (2H, d, J=5.8 Hz), 7.02 (1H, m), 7.14 (1H, s), 7.28 (1H, s), 7.30 (3H, m), 7.48 (2H, d, J=8.2 Hz), 7.50 (1H, m) and 7.60 (2H, d, J=8.2 Hz).

Biological Methods

Initial screening of candidate compounds was performed using viability assays on cultures of the macrophage cell line J774, which have been used before as a model system for osteoclast survival (see, e.g., Luckman et al., 1998). The assays are based on the survival of the J774 macrophage cell line; macrophages are closely related to osteoclasts.

Alamar Blue Macrophage J774 Viability Assay

J774 cells were plated at $10^4$ cells per well in 100 μL αMEM (α Modified Eagle Medium) in 96-well plates and grown overnight. The next day, test compounds were added to the cultures, and cultures were continued for another 72 hours. At the end of the culture period, cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance is measured at 570 nm (reduced form) and 600 nm (oxidised form) are typically used. A simple calculation is performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 10 μL). The plate was incubated at 37° C. for 3-4 hours and the fluorescence was measured at 590 nm, with a 25 nm bandwidth. A high reading indicated cells with normal viability, and a low reading indicated cells that have been damaged and are no longer proliferating normally. The controls gave a high fluorescence reading, indicating a high number of live, healthy cells. A potent test compound gave a low fluorescence reading. The average results for each test compound (n=5) were expressed as a percent (%) of the average control value.

Addition of Compounds.

All of the compounds studied were made up as 100 mM solutions in DMSO. These stock solutions were then diluted 1000-10000× in culture medium (αMEM). From these 100 μM or 10 μM solutions, convenient quantities (3-33 μL) were added directly to the wells so as to give the desired final compound concentration.

This assay offers numerous advantages over other assays, including MTT assays: it permits a higher throughput; it is more sensitive; it is non-damaging to the cells; it is faster; and it generally gives an identical result to MTT assays.

Cell Culture and Analysis of Cell Signalling

Bone marrow cells were flushed out of the long bones of 3-5 month old mice, and cultured in 10 cm tissue culture dishes for three days in α-MEM supplemented with 10% FCS, antibiotics, and recombinant mouse M-CSF (100 ng/mL). The cells were then harvested by trypsinisation, and re-plated in 6 well-plates (3×10$^5$ cells per well) and cultured in medium as described above for 2 more days. Cells were then serum starved and pre-treated with test compounds for 1 hour, followed by 5 minutes stimulation with TNFα. After stimulation, the cells were washed in PBS and homogenized in lysis buffer containing PBS, 0.1% (w/v) sodium dodecyl sulphate (SDS), 0.5% (w/v) sodium deoxycholate, and 2% (v/v) protease inhibitor cocktail. The cell lysates were centrifuged as 12,000 g for 10 minutes at 4° C., and the supernatant was collected and protein concentration determined using a Bio-Rad protein assay kit. Aliquots of the cell lysate containing 50 μg protein per lane were run on a 10% denaturing acrylamide gel and blotted onto a nylon membrane. The membranes were washed in Tris buffered saline (TBS) and incubated overnight at 4° C. with the relevant primary antibodies (phospho-IκB and phospho-p42/44 Erk, Cell Signalling Technology, 1:1000 dilution). The membranes were washed in TBS, incubated with the appropriate secondary antibodies coupled to HRP, washed in TBS again, and the bands visualised using chemiluminescence substrate (Amersham, UK) on a gel imaging system.

In Vivo Studies

Collagen-Induced Arthritis

Collagen-induced arthritis (CIA) was induced in 8-week old male DBA/1 mice, by intradermal injection of 100 μL of chicken collagen type II (2 mg/mL) suspended in complete Freund's adjuvant supplemented with 2 mg/mL devitalised *M. Tuberculosis* into the base of the tail. This will lead to joint inflammation in >80% of the animals within 4 weeks. Treatment with ABD455 (10 mg/kg/day, delivered in corn oil) was started when joint inflammation became apparent in the first animals (in this experiment 15 days after injection), and the experiment terminated 3 weeks later. The animals were scored for joint inflammation at least 3 times per week using the scoring system shown in the following table. For each animal the scores for all four joints were added (maximal score=12).

TABLE 1

Scoring Criteria

| Score | Criteria |
|---|---|
| 0 | Normal |
| 1 | Mild inflammation, limited to individual digits, regardless of the number of affected digits |
| 2 | Moderate redness and swelling of ankle or wrist |
| 3 | Severe redness and swelling of the entire paw including digits |

Pharmacokinetics Studies

Absorption and metabolic stability were studied using an in vivo pharmacokinetics assay. Drug levels assessed using HPLC/UV.

Following overnight starvation, male Wistar rats (250 g) were given a bolus gavage of 500 μL of a solution of test compound in corn oil (5 mg/mL). Blood samples (1 mL, whole blood) were taken at various time intervals and the serum collected following centrifugation. Samples were frozen until required for analysis.

Ethyl acetate (4 mL) was added to the defrosted serum and the samples mixed for 20 minutes. Following centrifugation, the ethyl acetate layer was collected and evaporated under a stream of nitrogen. The residue was reconstituted in mobile phase and 20 μL injected onto the chromatogram.

Standard calibration curves were prepared for each of the test compounds and were linear in the range of 1 ng/mL to 250 ng/mL.

Chromatographic Conditions:

Column: HIRPB C18 (150×4.6 mm).

Mobile phase: 60% 25 mM ammonium acetate, pH 4; 40% acetonitrile.

Flow rate: 1 mL/minute.

Detection: Peaks detected by UV absorption at $\lambda_{max}$ in the range of 240-275 nm.

Biological Data

Biological Study 1

The biological activity of the BPSAAA compounds can be compared for a range of related derivatives using the assays described previously. For example, $IC_{50}$ values were determined for several BPSAAA compounds using the Alamar Blue macrophage J774 viability assay described above. The results are summarised in the following table.

TABLE 1

Alamar Blue Macrophage J774 Viability Assay Data

| Compound | $(Q^1)_n$ | $(Q^2)_m$ | $(Q^3)_p$ | $IC_{50}$ (μM) |
|---|---|---|---|---|
| ABD446 | 4-Bromo | — | — | 2.5 ± 1 |
| ABD455 | 2,4-Dichloro | — | — | 0.5 ± 0.2 |
| ABD456 | 2,4-Difluoro | — | — | 0.25 ± 0.1 |
| ABD465 | 2,4-Difluoro | 2-Methyl | — | 0.1 ± 0.05 |
| ABD499 | 4-Bromo | — | 2-Methyl | 10 ± 3 |
| ABD500 | 4-Bromo | — | 6-Methyl | 0.20 ± 0.1 |
| ABD512 | 4-Trifluoromethyl | — | — | 2.0 ± 0.5 |
| ABD514 | 2-Nitro | — | — | >4 |
| ABD515 | 4-Bromo-2-fluoro | — | — | 0.2 ± 0.05 |
| ABD520 | 4-Bromo | — | 4-Chloro | 7 ± 3 |
| ABD523 | 4-Fluoro | 3-Trifluoromethoxy | — | 1.5 ± 0.5 |
| ABD525 | 4-Fluoro | — | — | 4.5 ± 1 |
| ABD527 | 2,4-Difluoro | — | 6-Methyl | 0.1 ± 0.05 |
| ABD528 | 4-Bromo | — | 6-Chloro | 6 ± 3 |
| ABD529 | 4-Bromo | — | 2-Methoxy | 1.5 ± 0.5 |
| ABD530 | 4-Bromo | — | 2-Chloro | 3 ± 1.5 |
| ABD545 | 2,4-Dichloro | — | 3-Hydroxymethyl | 2.5 ± 0.5 |
| ABD547 | 4-Bromo | — | 4-Hydroxy | 2.5 ± 0.5 |
| ABD550 | 2,4-Dichloro | — | 4-Hydroxymethyl | 1.2 ± 0.5 |
| ABD551 | 4-Fluoro | 3-Chloro | — | 1.2 ± 0.5 |
| ABD554 | 4-Bromo | — | 2-Hydroxy | 1 ± 0.5 |
| ABD559 | 4-Dimethylamino | — | — | >4 |
| ABD565 | 2,4-Difluoro | — | 4-Hydroxymethyl | 0.15 ± 0.1 |
| ABD568 | 4-Fluoro | — | 4-Hydroxymethyl | 1 ± 0.5 |
| ABD575 | 4-Chloro, 2-fluoro | — | — | 0.4 ± 0.25 |
| ABD576 | 4-Acetamido | — | — | >4 |
| ABD577 | 4-Methanesulfonyl | — | — | >4 |
| ABD578 | 4-Fluoro | — | 6-Methyl | 0.7 ± 0.25 |
| ABD579 | — | — | — | >4 |
| ABD585 | 2,4-Difluoro | — | 2-Hydroxy | 0.2 ± 0.1 |
| ABD587 | 4-Bromo | — | 6-Hydroxy | >4 |
| ABD588 | 2-Fluoro | — | — | 1 ± 0.5 |
| ABD589 | 4-Methyl | — | — | 1 ± 0.5 |

These data also demonstrate that it is possible to achieve substantial increases in potency by (a) the addition of hydrophobic, electron withdrawing substituents at 2- or 4-position of Ring A; (b) the addition of certain hydrophobic substituents on Ring B; and/or (c) the addition of certain substituents on Ring C.

Biological Study 2

The biological activity of BPSAAA compounds can be compared wherein the position and chain length of the hydroxyalkyl group has been varied, using the assays described previously. For example, $IC_{50}$ values were determined for several 4-bromo-biphenyl hydroxyalkyl-phenyl sulfonamides using the Alamar Blue macrophage J774 viability assay described above. The results are summarised in the following table.

These data also demonstrate that whilst the 3-hydroxymethanol derivatives show an optimal structure for maximised potency, other derivatives with slightly different structures are also highly potent.

Biological Study 3

The oral absorption of several BPSAAA compounds and a number of other known biphenyl hydroxyalkyl sulfonamides was compared in a rat model as described previously.

Serum levels of the following compounds, following oral dosage (10 mg/kg) over the course of 60 minutes, were investigated in vivo in rats using an HPLC/UV detection system, as described above:

TABLE 3

Compounds Used in Serum Levels Study

| Compound | Symbol | Structure | Name |
|---|---|---|---|
| ABD200 | (□) | (structure) | 4'-fluoro-biphenyl-4-sulfonic acid (4-hydroxybutyl)-amide |
| ABD295 | (○) | (structure) | 2',4'-difluoro-2-methyl-biphenyl-4-sulfonic acid (4-hydroxybutyl)-amide |
| ABD385 | (▲) | (structure) | 2',4'-difluoro-3-ethyl-biphenyl-4-sulfonic acid (4-hydroxybutyl)-amide |
| ABD455 | (Δ) | (structure) | 2',4'-dichloro-biphenyl-4-sulfonic acid (3-hydroxymethyl-phenyl)-amide |
| ABD456 | (■) | (structure) | 2',4'-difluoro-biphenyl-4-sulfonic acid (3-hydroxymethyl-phenyl)-amide |

TABLE 2

Alamar Blue Macrophage J774 Viability Assay Data (structure of Br-biphenyl-SO₂-NH-phenyl-Q with positions 2, 3, 4 marked)

| Compound | Q | $IC_{50}$ (μM) |
|---|---|---|
| ABD445 | 4-CH$_2$OH | 3.5 ± 1 |
| ABD446 | 3-CH$_2$OH | 2.5 ± 1 |
| ABD451 | 4-CH$_2$CH$_2$OH | 4.5 ± 1 |

FIG. 1 is a graph showing blood serum levels (ng/mL) of ABD200 (□), ABD295 (○), ABD385 (▲), ABD455 (Δ) and ABD456 (■) as a function of time (minutes) after oral administration (10 mg/kg).

The data show that ABD455 and ABD456 are well absorbed following oral administration and have a good degree of metabolic stability, and are therefore ideal as orally active drugs. The data also demonstrate that the known biphenyl hydroxyalkyl sulfonamides are not absorbed following oral administration, and therefore the biphenyl 3-hydroxymethyl-phenyl sulfonamides represent a significant advance on previously disclosed compounds.

Biological Study 4

The effect of ABD455 as an anti-inflammatory agent was investigated in the mouse collagen-induced arthritis (CIA) model as described above.

Compound ABD455 (dosage 10 mg/kg, i.p.) was investigated in vivo using the collagen-induced arthritis model, assessed using joint inflammation severity scoring, as described above.

Figure 2:
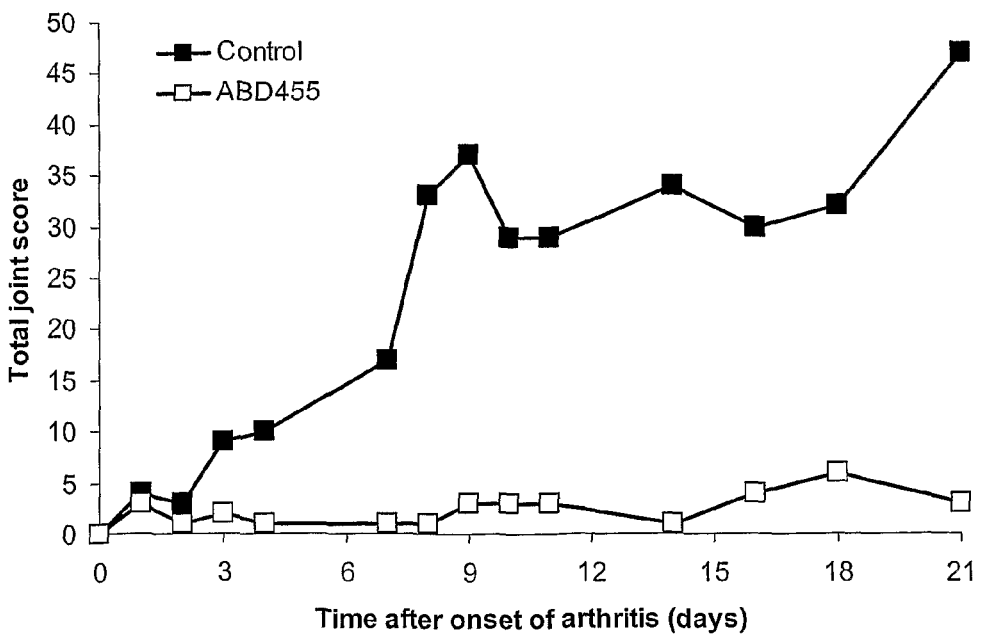
FIG. 2 is a graph showing the sum of the joint inflammation scores for each study group over a 21-day period following the first signs of inflammation in an arthritis model: (■) control group, no drug; (□) ABD455 (10 mg/kg/day, i.p.). The graph shows that the untreated study group has a total joint score of 47, whereas the group treated with ABD455 i.p. has a score of 3.

The collagen-induced arthritis data are illustrated in FIG. 2.

FIG. 2 is a graph showing the sum of the joint inflammation scores for each study group over a 21-day period following the first signs of inflammation: (■) control group, no drug; (□) ABD455 (10 mg/kg/day, i.p.); n=10 animals per group. The graph shows that after 21 days, the untreated study group had a total joint score of 47, whereas the group treated with ABD455 i.p. had a score of 3.

The data show that ABD455 is able to fully reverse the effects of collagen-induced arthritis, and show that ABD455 is very effective at preventing the inflammation seen in this model for arthritis.

Biological Study 5

For comparison purposes, the effect of a known biphenyl hydroxyalkyl sulfonamide (2',4'-difluoro-2-methyl-biphenyl-4-sulfonic acid (4-hydroxybutyl)-amide; ABD295) as an anti-inflammatory agent was investigated in the mouse collagen-induced arthritis model as described above.

Compound ABD295 (dosage 10 mg/kg, i.p.) was investigated in vivo using the collagen-induced arthritis model, assessed using joint inflammation severity scoring, as described above.

Figure 3:
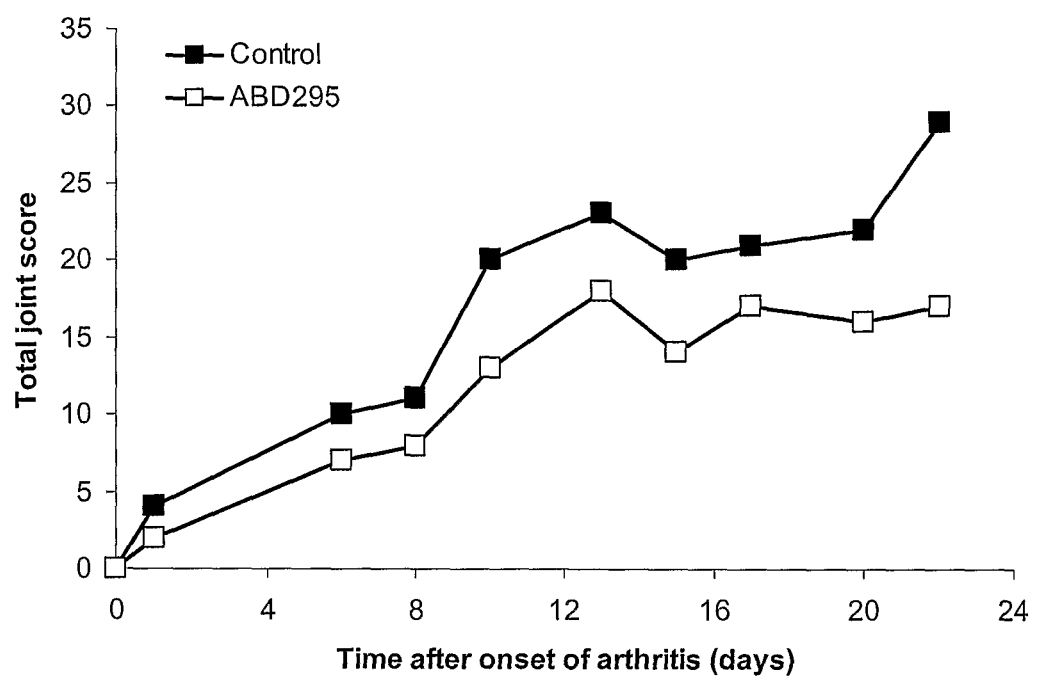
FIG. 3 is a graph showing the sum of the joint inflammation scores for each study group over a 22-day period following the first signs of inflammation in an arthritis model: (■) control group, no drug; (□) ABD295 (10 mg/kg/day, i.p.). The graph shows that the untreated study group has a total joint score of 29, whereas the group treated with ABD295 i.p. has a score of 17.

The collagen-induced arthritis data are illustrated in FIG. 3.

FIG. 3 is a graph showing the sum of the joint inflammation scores for each study group over a 22-day period following the first signs of inflammation: (■) control group, no drug; (□) ABD295 (10 mg/kg/day, i.p.); n=8 animals per group. The graph shows that after 22 days, the untreated study group has a total joint score of 29, whereas the group treated with ABD295 i.p. has a score of 17.

The data show that ABD455 is much more effective in reversing the effects of collagen-induced arthritis than ABD295, and highlight the significant improvement in activity demonstrated by the BPSAAA compounds over the known biphenyl hydroxyalkyl sulfonamides.

Biological Study 6

The effect of ABD455 and ABD456 as inhibitors of TNF-signalling was investigated in cultures of mouse macrophages as described above.

Compounds ABD455 and ABD456 (at both 10 µM and 25 µM) were investigated in vitro using TNFα-stimulated mouse macrophages, assessing TNF-dependent activation of intracellular signalling by visualising phosphorylation of IκB and p42/44 Erk using Western blotting as described above.

Figure 4:
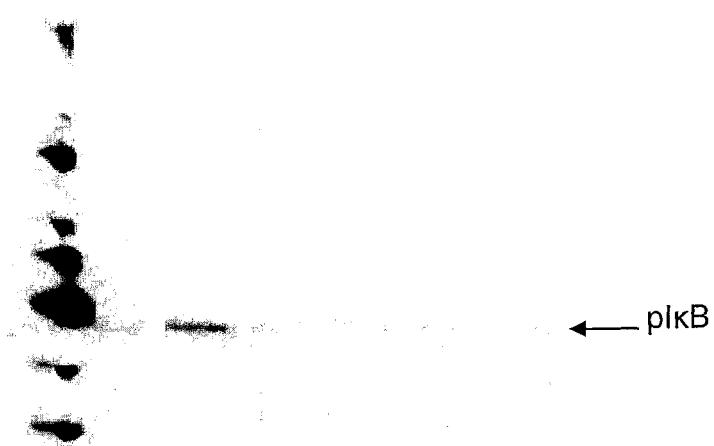
FIG. 4 is a Western blot showing the effects of ABD455 and ABD456 on TNF-stimulated phosphorylation of IκB. The data show that ABD455 and ABD456 completely block TNFα-stimulated phosphorylation of IκB
Figure 5:
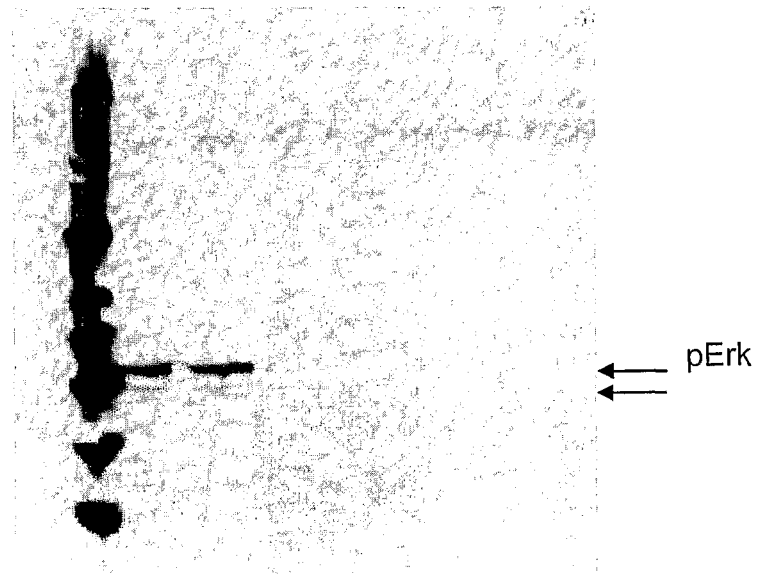
FIG. 5 is a Western blot showing the effects of ABD455 and ABD456 on TNF-stimulated phosphorylation of p42/44 Erk. The data show that ABD455 and ABD456 completely block TNFα-stimulated phosphorylation of p42/44 Erk.

The Western blotting data are illustrated in FIGS. 4 and 5.

FIG. 4 is a Western blot showing the effects of ABD455 and ABD456 on TNF-stimulated phosphorylation of IκB.

FIG. 5 is a Western blot showing the effects of ABD455 and ABD456 on TNF-stimulated phosphorylation of p42/44 Erk.

The data show that ABD455 and ABD456 completely block TNFα-stimulated phosphorylation of IκB and p42/44 Erk.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Baud V, Liu Z G, Bennett B, Suzuki N, Xia Y, Karin M, 1999, "Signaling by proinflammatory cytokines: oligomerization of TRAF2 and TRAF6 is sufficient for JNK and IKK activation and target gene induction via an amino-terminal effector domain", *Genes Dev.*, Vol. 13, pp. 1297-1308.

Brennan F M, Chantry D, Jackson A, Maini R, Feldmann M, 1989, "Inhibitory effect of TNF alpha antibodies on synovial cell interleukin-1 production in rheumatoid arthritis", *Lancet*, Vol. 2, pp. 244-247

Brennan F M, Feldmann M, 1996, "Cytokines in autoimmunity", *Curr. Opin. Immunol.*, Vol. 8, pp. 872-877.

Brennan F M, Gibbons D L, Mitchell T, Cope A P, Maini R N, Feldmann M, 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Elliott M J, Maini R N, Feldmann M, Kalden J R, Antoni C, Smolen J S, Leeb B, Breedveld F C, Macfarlane J D, Bijl H, 1994, "Randomised double-blind comparison of chimeric monoclonal antibody to tumour necrosis factor alpha (cA2) versus placebo in rheumatoid arthritis", *Lancet*, Vol. 344, pp. 1105-1110.

Feldmann M, Brennan F M, Elliott M, Katsikis P, Maini R N, 1994, "TNF alpha as a therapeutic target in rheumatoid arthritis," *Circ. Shock*, Vol. 43, pp. 179-184.

Feldmann M, Brennan F M, Foxwell B M, Maini R N, 2001, "The role of TNF alpha and IL-1 in rheumatoid arthritis," *Curr. Dir. Autoimmun.*, Vol. 3, pp. 188-199.

Feldmann M, Brennan F M, Maini R N, 1996, "Rheumatoid arthritis", *Cell*, Vol. 85, pp. 307-310.

Firestein G S, 1996, "Invasive fibroblast-like synoviocytes in rheumatoid arthritis. Passive responders or transformed aggressors?", *Arthritis Rheum.*, Vol. 39, pp. 1781-1790.

Firestein G S, 2005 "Immunologic mechanisms in the pathogenesis of rheumatoid arthritis", *J. Clin. Rheumatol.*, Vol. 11. pp. S39-S44.

Firestein G S, Manning A M, 1999, "Signal transduction and transcription factors in rheumatic disease", *Arthritis Rheum.*, Vol. 42, pp. 609-621.

Gottlieb A B, 2005, "Psoriasis: Emerging Therapeutic Strategies", *Nat. Rev. Drug Disc.*, Vol. 4, pp. 19-34.

Greig I R, Idris A I, Ralston S H and van't Hof R J 2006: "Development and characterization of biphenylsulfonamides as novel inhibitors of bone resorption". *J. Med. Chem.*, Vol 49: pp 7487-7492

Greig I R, Mohamed A I, Ralston S H and van't Hof R J 2004: "Alkyl aryl sulfonamides as therapeutic agents for the treatment of bone conditions". Published international application publication number WO2005118528

Jimi E, Aoki K, Saito H, D'Acquisto F, May M J, Nakamura I, Sudo T, Kojima T, Okamoto F, Fukushima H, Okabe K, Ohya K, Ghosh S, 2004, "Selective inhibition of NF-kappa B blocks osteoclastogenesis and prevents inflammatory bone destruction in vivo", *Nat. Med.*, Vol. 10, pp. 617-624.

Joosten L A, Nelsen M M, van de Loo F A, van den Berg W B, 1996, "Anticytokine treatment of established type II collagen-induced arthritis in DBA/1 mice. A comparative study using anti-TNF alpha, anti-IL-1 alpha/beta, and IL-1 Ra," *Arthritis Rheum.*, Vol. 39, pp. 797-809.

Klareskog L, Gaubitz M, Rodriguez-Valverde V, Malaise M, Dougados M, Wajdula J, 2006, "A long-term, open-label trial of the safety and efficacy of etanercept (Enbrel) in patients with rheumatoid arthritis not treated with other disease-modifying antirheumatic drugs", *Ann. Rheum. Dis.*, Vol. 65, pp. 1578-1584.

Klareskog L, Padyukov L, Lorentzen J, Alfredsson L, 2006, "Mechanisms of disease: Genetic susceptibility and environmental triggers in the development of rheumatoid arthritis," *Nat. Clin. Pract. Rheumatol.*, Vol. 2, pp. 425-433.

Korzenik J R and Podolsky D K, 2006, "Evolving knowledge and therapy of inflammatory bowel disease," *Nat. Rev. Drug Disc.*, Vol. 5, pp. 197-209.

Liu Z G, 2005, "Molecular mechanism of TNF signaling and beyond," *Cell Res.*, Vol. 15, pp. 24-27.

Luckman S P, Coxon F P, Ebetino F H, Russell R G, Rogers M J, 1998, "Heterocycle-containing bisphosphonates cause apoptosis and inhibit bone resorption by preventing protein prenylation: evidence from structure-activity relationships in J774 macrophages," *J. Bone Miner. Res.*, Vol. 13, pp. 1668-1678.

McInnes I B, Gracie J A, 2005, "Targeting cytokines beyond tumor necrosis factor-alpha and interleukin-1 in rheumatoid arthritis", *Curr. Pain Headache Rep.*, Vol. 9, pp. 405-411.

Mount C and Featherstone J, 2005, "Rheumatoid arthritis market", *Nat. Rev. Drug Disc.*, Vol. 2, pp. 11-12.

Nociari, M N., et al., 1998, "A Novel one-step, highly sensitive fluorimetric assay to evaluate cell-mediated cytotoxicity", *Journal of Immunological Methods*, Vol. 213, pp. 157-167.

O'Brien P M, Ortwine D F, Pavlovsky A G, Picard J A, Sliskovic D R, Roth B D, Dyer R D, Johnson L L, Man C F and Hallak H, 2000: "Structure-activity relationships and pharmacokinetic analysis for a series of potent, systemically available biphenylsulfonamide matrix metalloproteinase inhibitors". *J. Med. Chem.* Vol 43: pp 156-166

Roodman G D, 2006, "Regulation of osteoclast differentiation", *Ann. N.Y. Acad. Sci.*, Vol. 1068, pp. 100-109.

Smolen J S and Steiner G, 2003, "Therapeutic Strategies for Rheumatoid Arthritis", *Nat. Rev. Drug Disc.*, Vol. 2, pp. 473-488.

Tanaka S, Nakamura I, Inoue J, Oda H, Nakamura K, 2003, Signal transduction pathways regulating osteoclast differentiation and function," *J. Bone Miner. Metab.*, Vol. 21, pp. 123-133.

van den Berg W B, 2002, "Is there a rationale for combined TNF and IL-1 blocking in arthritis?", *Clin. Exp. Rheumatol.*, Vol. 20, pp. S21-S25.

van den Berg W B, Bresnihan B, 1999, "Pathogenesis of joint damage in rheumatoid arthritis: evidence of a dominant role for interleukin-I", *Baillieres Best Pract. Res. Clin. Rheumatol.*, Vol. 13, pp. 577-597.

Weissmann G, 2006, "The pathogenesis of rheumatoid arthritis," *Bull. Hosp. Jt. Dis.*, Vol. 64, pp. 12-15.

Ziff M, 1990, "Rheumatoid arthritis—it's present and future", *J. Rheumatol.*, Vol. 17, pp. 127-133.

The invention claimed is:

1. A compound selected from compounds of the following formula and pharmaceutically acceptable salts thereof:

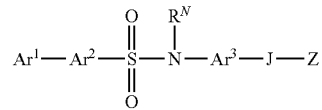

wherein:

$Ar^1$—$Ar^2$— is a group of the following formula:

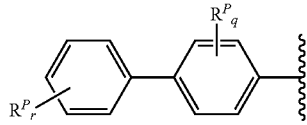

q is independently 0, 1, or 2;
r is independently 0, 1, 2, or 3;
each $R^P$ is independently a ring substituent;
—$R^N$ is independently —H or —$R^{NN}$;
—$R^{NN}$ is $C_{1-6}$alkyl;
—$Ar^3$— is independently 1,3-phenylene or 1,4-phenylene, and is optionally substituted with one or more substituents —$R^{AR3}$, wherein each —$R^{AR3}$ is independently a ring substituent;
—Z is independently —OH or —O—W;
-J- is —$R^{alk}$—;
—$R^{alk}$— is saturated aliphatic $C_{1-5}$alkylene, and is optionally substituted with one or more substituents —$R^{AA}$, wherein each —$R^{AA}$ is independently —F, —Cl, —Br, —I, —OH, —$OR^{A2}$, —$OCF_3$, —$NH_2$, —$NHR^{A2}$, —$NR^{A2}_2$, —C(=O)$NH_2$, —C(=O)$NHR^{A2}$, or —C(=O)$NR^{A2}_2$, wherein each $R^{A2}$ is independently $C_{1-4}$alkyl;
—W is independently —$R^{E1}$, —C(=O)—$R^{E2}$, or —C(=O)—O—$R^{E3}$;
each of $R^{E1}$, $R^{E2}$, and $R^{E3}$ is independently —H, $C_{1-3}$alkyl, phenyl, or —$CH_2$-phenyl; and
each ring substituent is independently —F, —Cl, —Br, —I, —$R^{D9}$, —$CF_3$, —OH, —$OR^{D9}$, —$OCF_3$, —CN, —$NO_2$, —$NH_2$, —$NHR^{D9}$, or —$NR^{D9}_2$, wherein each —$R^{D9}$ is independently saturated aliphatic $C_{1-3}$alkyl.

2. A compound according to claim 1, wherein —Z is —OH.

3. A compound according to claim 2, wherein $Ar^1$—$Ar^2$— is a group of the following formula:

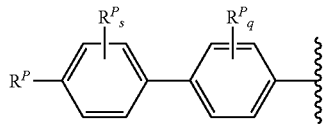

wherein:
q is independently 0, 1, or 2;
s is independently 0, 1, or 2.

4. A compound according to claim 2, wherein $Ar^1$—$Ar^2$— is a group of the following formula:

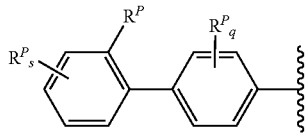

wherein:
q is independently 0, 1, or 2;
s is independently 0, 1, or 2.

5. A compound according to claim 2, wherein $Ar^1$—$Ar^2$— is a group of the following formula:

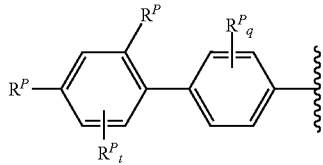

wherein:
q is independently 0, 1, or 2;
t is independently 0 or 1.

6. A compound according to claim 2, wherein $Ar^1$—$Ar^2$— is a group of the following formula:

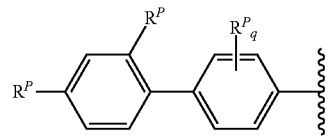

wherein:
q is independently 0, 1, or 2.

7. A compound according to claim 2, wherein $Ar^1$—$Ar^2$— is a group of the following formula:

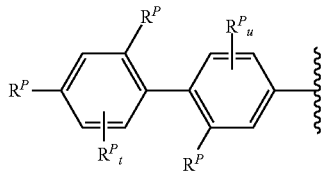

wherein:
t is independently 0 or 1;
u is independently 0 or 1.

8. A compound according to claim 2, wherein $Ar^1$—$Ar^2$— is a group of the following formula:

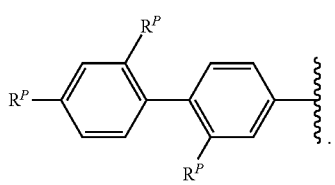

9. A compound according to claim 2, wherein —$Ar^3$— is 1,3-phenylene, and is optionally substituted with one or more substituents —$R^{AR3}$.

10. A compound according to claim 3, wherein —$Ar^3$— is 1,3-phenylene, and is optionally substituted with one or more substituents —$R^{AR3}$.

11. A compound according to claim 4, wherein —$Ar^3$— is 1,3-phenylene, and is optionally substituted with one or more substituents —$R^{AR3}$.

12. A compound according to claim 6, wherein —$Ar^3$— is 1,3-phenylene, and is optionally substituted with one or more substituents —$R^{AR3}$.

13. A compound according to claim 8, wherein —$Ar^3$— is 1,3-phenylene, and is optionally substituted with one or more substituents —$R^{AR3}$.

14. A compound according to claim 3, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

15. A compound according to claim 6, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

16. A compound according to claim 8, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

17. A compound according to claim 10, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

18. A compound according to claim 12, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

19. A compound according to claim 13, wherein —$R^{alk}$— is saturated aliphatic $C_{1-3}$alkylene, and is optionally substituted with one or more substituents —$R^{AA}$, wherein each —$R^{AA}$ is independently —F, —Cl, —Br, —I, —OH, —OMe, —OEt, —$OCF_3$, —$NH_2$, —NHMe, —NHEt, —$NMe_2$, —$NEt_2$, —C(=O)$NH_2$, —C(=O)NHMe, —C(=O)NHEt, —C(=O)$NMe_2$, or —C(=O)$NEt_2$.

20. A compound according to claim 3, wherein —$R^{alk}$— is independently —$CH_2$— or —$(CH_2)_2$—.

21. A compound according to claim 6, wherein —$R^{alk}$— is independently —$CH_2$— or —$(CH_2)_2$—.

22. A compound according to claim 8, wherein —$R^{alk}$— is independently —$CH_2$— or —$(CH_2)_2$—.

23. A compound according to claim 10, wherein —$R^{alk}$— is independently —$CH_2$— or —$(CH_2)_2$—.

24. A compound according to claim 12, wherein —$R^{alk}$— is independently —$CH_2$— or —$(CH_2)_2$—.

25. A compound according to claim 13, wherein —$R^{alk}$— is independently —$CH_2$— or —$(CH_2)_2$—.

26. A compound according to claim 3, wherein each ring substituent is independently —F, —Cl, —Br, —I, -Me, —CF$_3$, or —CN.

27. A compound according to claim 6, wherein each ring substituent is independently —F, —Cl, —Br, —I, -Me, —CF$_3$, or —CN.

28. A compound according to claim 8, wherein each ring substituent is independently —F, —Cl, —Br, —I, -Me, —CF$_3$, or —CN.

29. A compound according to claim 10, wherein each ring substituent is independently —F, —Cl, —Br, —I, -Me, —CF$_3$, or —CN.

30. A compound according to claim 12, wherein each ring substituent is independently —F, —Cl, —Br, —I, -Me, —CF$_3$, or —CN.

31. A compound according to claim 13, wherein each ring substituent is independently —F, —Cl, —Br, —I, -Me, —CF$_3$, or —CN.

32. A compound according to claim 14, wherein each ring substituent is independently —F, —Cl, —Br, —I, -Me, —CF$_3$, or —CN.

33. A compound according to claim 15, wherein each ring substituent is independently —F, —Cl, —Br, —I, -Me, —CF$_3$, or —CN.

34. A compound according to claim 16, wherein each ring substituent is independently —F, —Cl, —Br, —I, -Me, —CF$_3$, or —CN.

35. A compound according to claim 17, wherein each ring substituent is independently —F, —Cl, —Br, —I, -Me, —CF$_3$, or —CN.

36. A compound according to claim 18, wherein each ring substituent is independently —F, —Cl, —Br, —I, -Me, —CF$_3$, or —CN.

37. A compound according to claim 19, wherein each ring substituent is independently —F, —Cl, —Br, —I, -Me, —CF$_3$, or —CN.

38. A compound according to claim 20, wherein each ring substituent is independently —F, —Cl, —Br, —I, -Me, —CF$_3$, or —CN.

39. A compound according to claim 21, wherein each ring substituent is independently —F, —Cl, —Br, —I, -Me, —CF$_3$, or —CN.

40. A compound according to claim 22, wherein each ring substituent is independently —F, —Cl, —Br, —I, -Me, —CF$_3$, or —CN.

41. A compound according to claim 23, wherein each ring substituent is independently —F, —Cl, —Br, —I, -Me, —CF$_3$, or —CN.

42. A compound according to claim 24, wherein each ring substituent is independently —F, —Cl, —Br, —I, -Me, —CF$_3$, or —CN.

43. A compound according to claim 25, wherein each ring substituent is independently —F, —Cl, —Br, —I, -Me, —CF$_3$, or —CN.

44. A compound according to claim 1, selected from compounds of the following formulae and pharmaceutically acceptable salts thereof:

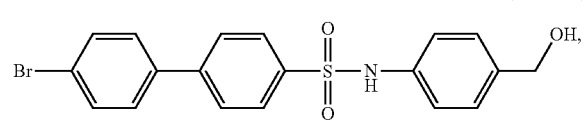
(ABD445)

-continued

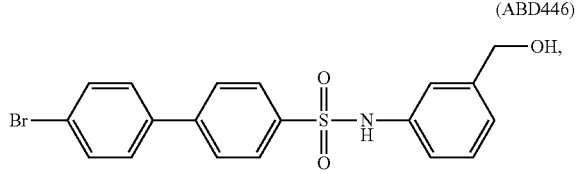
(ABD446)

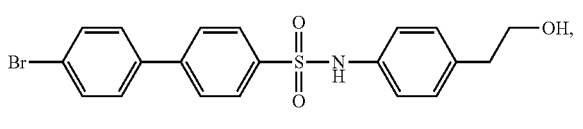
(ABD451)

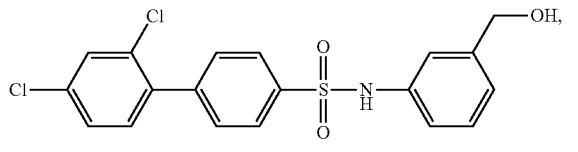
(ABD455)

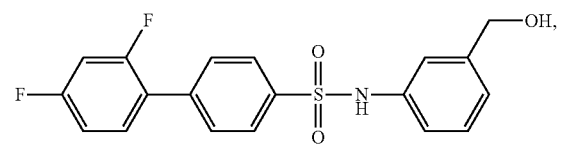
(ABD456)

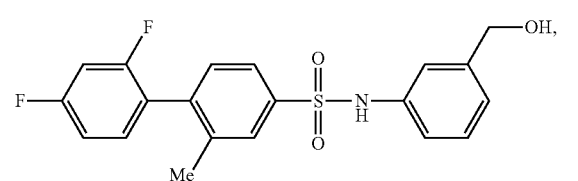
(ABD465)

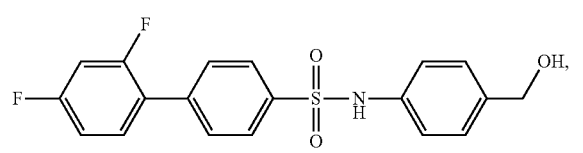
(ABD466)

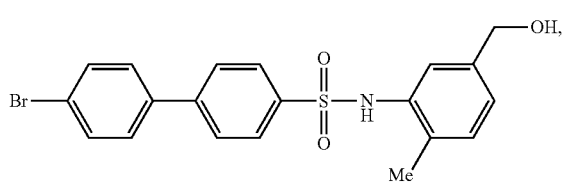
(ABD499)

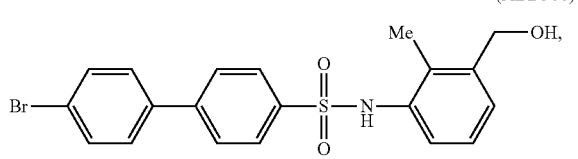
(ABD500)

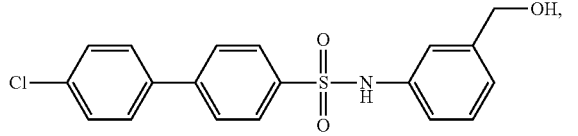
(ABD510)

-continued
(ABD512)
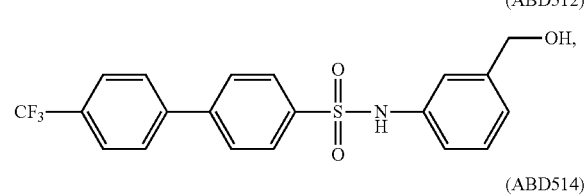
(ABD514)
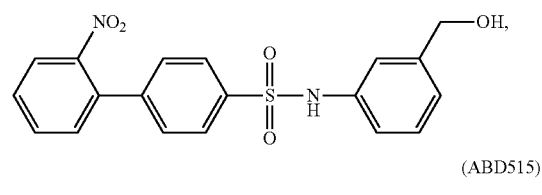
(ABD515)
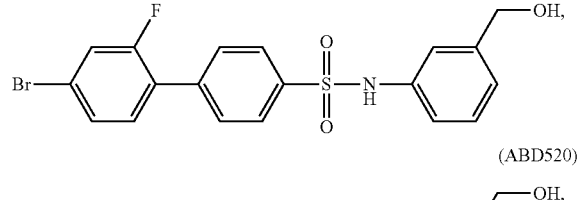
(ABD520)
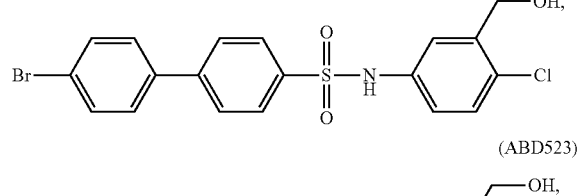
(ABD523)
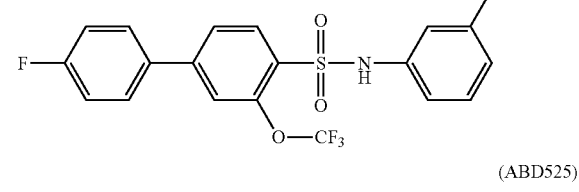
(ABD525)
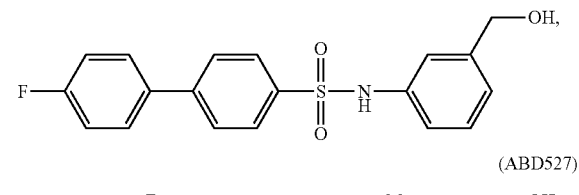
(ABD527)
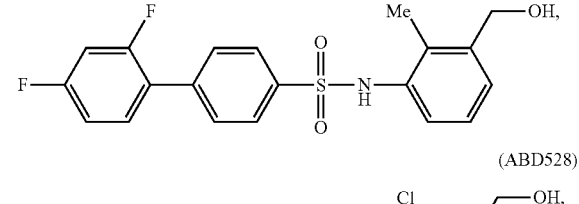
(ABD528)
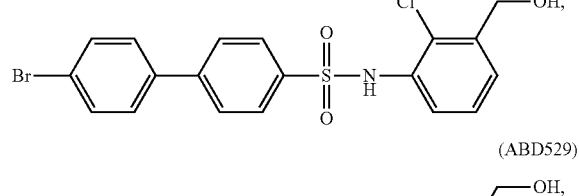
(ABD529)
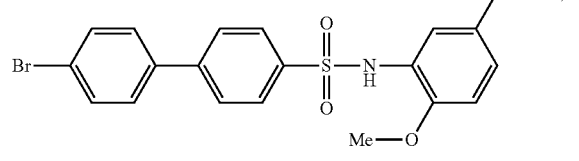
-continued
(ABD530)
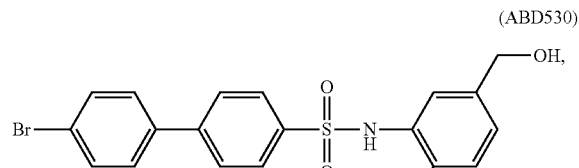
(ABD547)
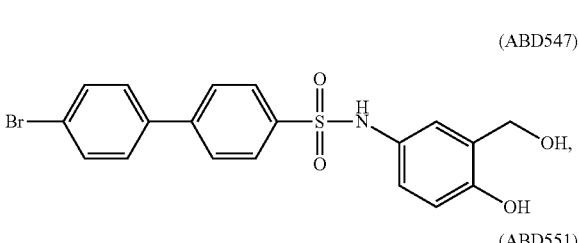
(ABD551)
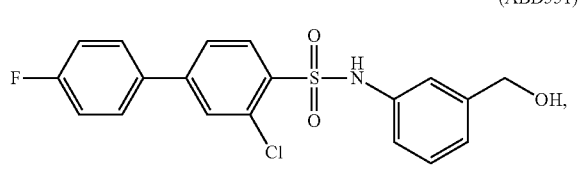
(ABD554)
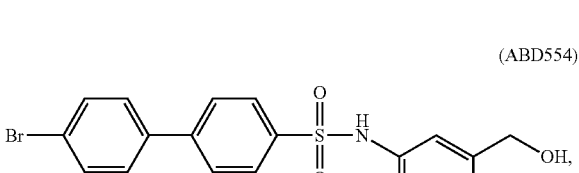
(ABD559)
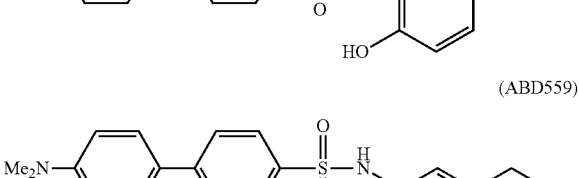
(ABD575)
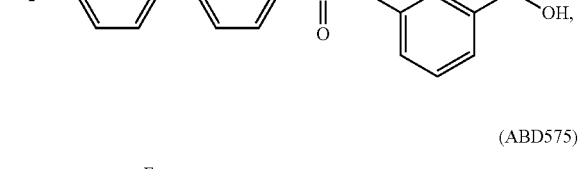
(ABD578)
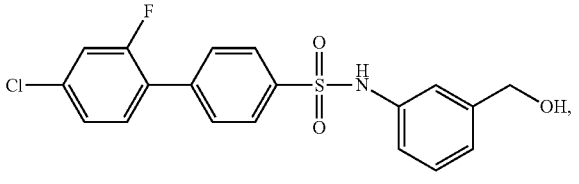
(ABD579)
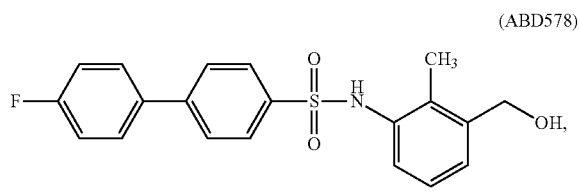

-continued (ABD585)
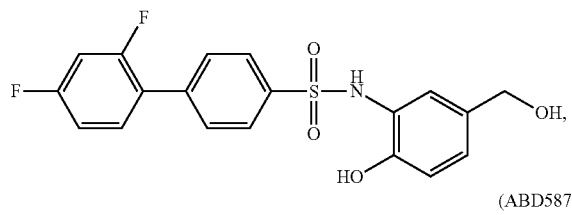

(ABD587)
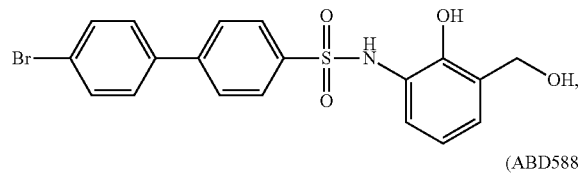

(ABD588)
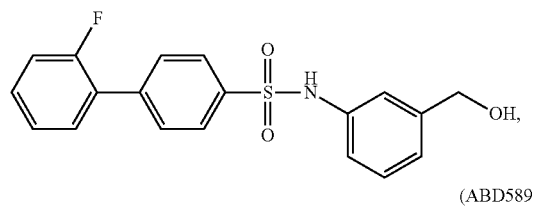

(ABD589)
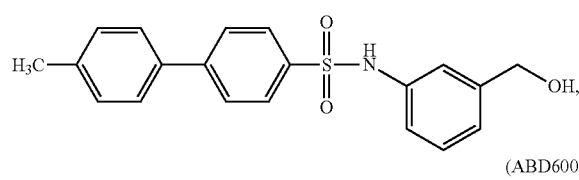

(ABD600)
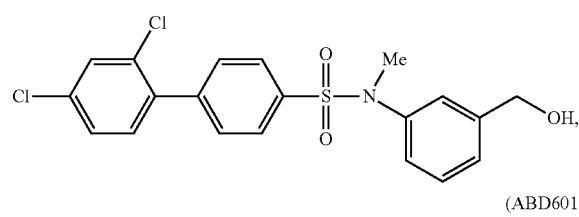

(ABD601)
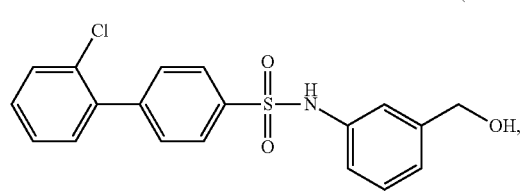

-continued (ABD625)
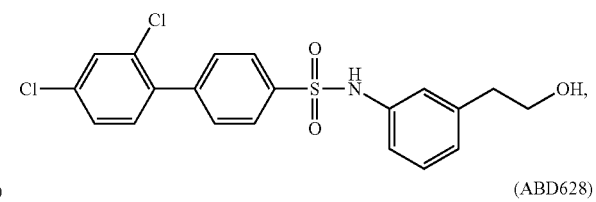

(ABD628)
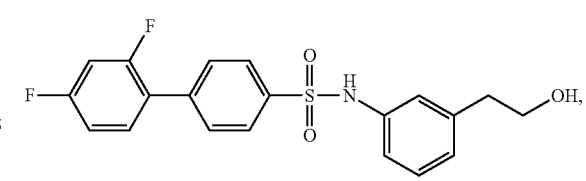

and (ABD630)
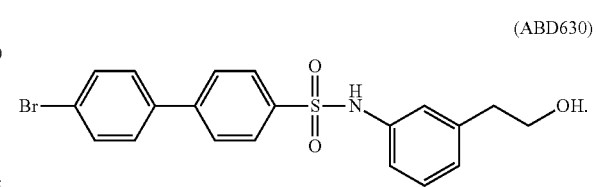

45. A pharmaceutical composition comprising a compound according to claim 1 and a pharmaceutically acceptable carrier or diluent.

46. A pharmaceutical composition comprising a compound according to claim 36 and a pharmaceutically acceptable carrier or diluent.

47. A pharmaceutical composition comprising a compound according to claim 37 and a pharmaceutically acceptable carrier or diluent.

48. A method of treatment and/or prevention of rheumatoid arthritis, comprising administering to a patient in need thereof, a therapeutically effective amount of a compound according to claim 1.

49. A method of treatment and/or prevention of rheumatoid arthritis, comprising administering to a patient in need thereof, a therapeutically effective amount of a compound according to claim 36.

50. A method of treatment and/or prevention of rheumatoid arthritis, comprising administering to a patient in need thereof, a therapeutically effective amount of a compound according to claim 37.

* * * * *

UNITED STATES PATENT AND TRADEMARK OFFICE
CERTIFICATE OF CORRECTION

| | |
|---|---|
| PATENT NO. | : 8,524,778 B2 |
| APPLICATION NO. | : 12/531732 |
| DATED | : September 3, 2013 |
| INVENTOR(S) | : Greig et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 943 days.

Signed and Sealed this
First Day of March, 2016

Michelle K. Lee
*Director of the United States Patent and Trademark Office*